(12) United States Patent
Piwnica-Worms et al.

(10) Patent No.: US 8,652,442 B2
(45) Date of Patent: Feb. 18, 2014

(54) BIOLUMINESCENCE IMAGING OF MYELOPEROXIDASE ACTIVITY IN VIVO, METHODS, COMPOSITIONS AND APPARATUSES THEREFOR

(75) Inventors: David Piwnica-Worms, Ladue, MO (US); Shimon Gross, St. Yavne, IL (US); Vijay Sharma, Wildwood, MO (US); Seth Gammon, St. Louis, MO (US)

(73) Assignee: Washington University, Saint Louis, MO (US)

( * ) Notice: Subject to any disclaimer, the term of this patent is extended or adjusted under 35 U.S.C. 154(b) by 63 days.

(21) Appl. No.: 13/127,448

(22) PCT Filed: Nov. 3, 2009

(86) PCT No.: PCT/US2009/063186
§ 371 (c)(1),
(2), (4) Date: Jun. 22, 2011

(87) PCT Pub. No.: WO2010/062787
PCT Pub. Date: Jun. 3, 2010

(65) Prior Publication Data
US 2011/0250145 A1    Oct. 13, 2011

Related U.S. Application Data

(60) Provisional application No. 61/110,727, filed on Nov. 3, 2008.

(51) Int. Cl.
*A61B 5/00* (2006.01)
*C07D 237/30* (2006.01)

(52) U.S. Cl.
USPC .......................................... 424/9.6; 544/237

(58) Field of Classification Search
None
See application file for complete search history.

(56) References Cited

U.S. PATENT DOCUMENTS

| | | | | |
|---|---|---|---|---|
| 4,363,759 | A | * | 12/1982 | Boguslaski et al. .......... 530/303 |
| 5,420,275 | A | | 5/1995 | Masuya et al. |
| 5,556,758 | A | | 9/1996 | Allen |
| 5,650,135 | A | | 7/1997 | Contag et al. |
| 5,922,558 | A | | 7/1999 | Akhavan-Tafti |
| 6,022,699 | A | | 2/2000 | Graff et al. |
| 6,495,355 | B1 | | 12/2002 | Contag et al. |
| 6,615,063 | B1 | | 9/2003 | Ntziachristos et al. |
| 6,638,752 | B2 | | 10/2003 | Contag et al. |
| 6,858,773 | B2 | | 2/2005 | Zhang et al. |
| 7,091,051 | B2 | | 8/2006 | Kitaoka et al. |
| 7,198,774 | B2 | | 4/2007 | Contag et al. |
| 7,255,851 | B2 | | 8/2007 | Contag et al. |
| 7,256,292 | B2 | | 8/2007 | Graham et al. |
| 7,425,560 | B2 | | 9/2008 | Tiden |

| | | | |
|---|---|---|---|
| 2003/0232368 | A1 | 12/2003 | Billon et al. |
| 2005/0054587 | A1 | 3/2005 | Culic et al. |
| 2006/0024232 | A1 | 2/2006 | Schnitzer et al. |

OTHER PUBLICATIONS

Dahlgren et al. Respiratory burst in human neutrophils. 1999 J. Immunol. Methods 232: 3-14.*
Nikokavouras et al. Chemiluminescence of a luminol-fluoresceine amide. 1976 Chimika Chronika 5: 223-229.*
Ruedas-Rama et al. A quantum dot-lucigenin probe for Cl-. 2008 Analyst 133: 1556-1566. Published online Aug. 1, 2008.*
Myhre et al. Evaluation of the probes 2',7'-dichlorofluorescin diacetate, luminol, and lucigenin as indicators of reactive species formation. 2003 Biochem. Pharmacol. 65: 1575-1582.*
Bender, J. G., et al., "Analysis of the bimodal chemiluminescence pattern stimulated in human neutrophils by chemotactic factors," Infect Immun 41, 1062-1070, 1983.
Brestel, E. P., "Co-oxidation of luminol by hypochlorite and hydrogen peroxide implications for neutrophil chemiluminescence," Biochem Biophys Res Commun 126, 482-8, 1985.
Carulli, G., et al., "Luminol-enhanced, whole blood chemiluminescence of human neutrophils evaluated by means of an automated, computer-assisted, and high-sensitivity luminescence analyzer," Int. J. Clin. Lab. Res. 25, 216-221, 1995.
Cohen, M. S., et al., "Further evaluation of luminol-enhanced luminescence in the diagnosis of disorders of leukocyte oxidative metabolism: role of myeloperoxidase," Clin. Chem. 29, 513-515, 1983.
Dahlgren, C., et al., "Respiratory burst in human neutrophils," J Immunol Methods 232, 3-14, 1999.
Daiber, A., et al., "Measurement of NAD(P)H oxidase-derived superoxide with the luminol analogue L-012," Free Radic. Biol. Med. 36: 101-111, 2004.
Eiserich, J.P., et al., "Myeloperoxidase, a leukocyte-derived vascular NO oxidase," Science 296, 2391-2394, 2002.
Gerber, C. E., et al., "Phagocytic activity and oxidative burst of granulocytes in persons with myeloperoxidase deficiency," Eur. J. Clin. Chem. Clin. Biochem. 34, 901-908, 1996.
Hallett, M. B., et al., "Detection and visualization of oxidase activity in phagocytes," Methods Mol. Biol. 225, 61-67, 2003.
Jancinova, V, et al., "The combined luminol/isoluminol chemiluminescence method for differentiating between extracellular and intracellular oxidant production by neutrophils," Redox Rep 11, 110-116, 2006.

(Continued)

*Primary Examiner* — Michael G Hartley
*Assistant Examiner* — Jennifer Lamberski
(74) *Attorney, Agent, or Firm* — Saul L. Zackson; Zackson Law LLC

(57) ABSTRACT

Methods of imaging distribution of myeloperoxidase activity in a subject are disclosed. These methods include the use of bioluminescent substrates, including luminol and wavelength-shifted analogues of luminol. Bioluminescent myeloperoxidase substrates that emit light at longer wavelengths compared to luminol are shown to be useful for imaging myeloperoxidase activity in vivo. The disclosed methods can be used for imaging sites of inflammation and other pathological conditions associated with abnormal levels of MPO activity in vivo. Methods of synthesis of luminol analogues are also disclosed.

6 Claims, 24 Drawing Sheets

(56) References Cited

OTHER PUBLICATIONS

Lundqvist, H., et al., "Isoluminol-enhanced chemiluminescence: a sensitive method to study the release of superoxide anion from human neutrophils," Free Radic. Biol. Med. 20, 785-792, 1996.

Pavelkova, M., et al., "Luminol-, isoluminol- and lucigenin-enhanced chemiluminescence of rat blood phagocytes stimulated with different activators," Luminescence 19, 37-42, 2004.

Shepherd et al. "Afluorescent probe for the detection of myeloperoxidase activity in atherosclerosis-associated macrophages" Chemistry & Biology 14:1221-1231, 2007.

Klebanoff, S.J., "Myeloperoxidase: friend and foe" J. Leukoc. Biol. 77, 598-625, 2005.

Hirche, T.O., et al., "Myeloperoxidase plays critical roles in killing *Klebsiella pneumoniae* and inactivating neutrophil elastase: effects on host defense" J Immunol 174, 1557-1565, 2005.

Henderson, J. P., et al., "Phagocytes produce 5-chlorouracil and 5-bromouracil, two mutagenic products of myeloperoxidase, in human inflammatory tissue" J. Biol. Chem. 278, 23522-23528, 2003.

Brennan, M. L., et al., "Prognostic value of myeloperoxidase in patients with chest pain" N. Engl. J. Med. 349, 1595-1604, 2003.

Chen, J. W., et al., "Imaging of myeloperoxidase in mice by using novel amplifiable paramagnetic substrates" Radiology 240, 473-481, 2006.

Kettle, A.J., et al., "Inhibition of myeloperoxidase by benzoic acid hydrazides" Biochem J 308 ( Pt 2), 559-563, 1995.

Kettle, A.J., et al., "Mechanism of inactivation of myeloperoxidase by 4-aminobenzoic acid hydrazide" Biochem J 321 ( Pt 2), 503-508, 1997.

Brennan, M.L. et al. "Increased atherosclerosis in myeloperoxidase-deficient mice" J Clin Invest 107, 419-430, 2001.

Bednar, M. et al., "Peroxynitrite augments fMLP-stimulated chemiluminescence by neutrophils in human whole blood" J Leukoc Biol 60, 619-624, 1996.

Slungaard, A., et al., "Thiocyanate is the major substrate for eosinophil peroxidase in physiologic fluids. Implications for cytotoxicity" J. Biol. Chem. 266, 4903-4910, 1991.

Gammon, S. T., et al., "Spectral unmixing of multicolored bioluminescence emitted from heterogeneous biological sources" Anal. Chem. 78, 1520-1527, 2006.

\* cited by examiner

FIG. 1 A-C
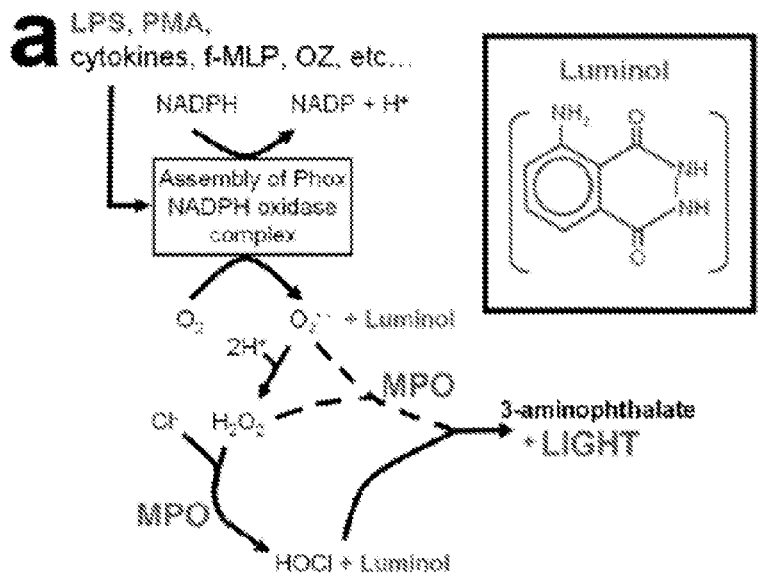
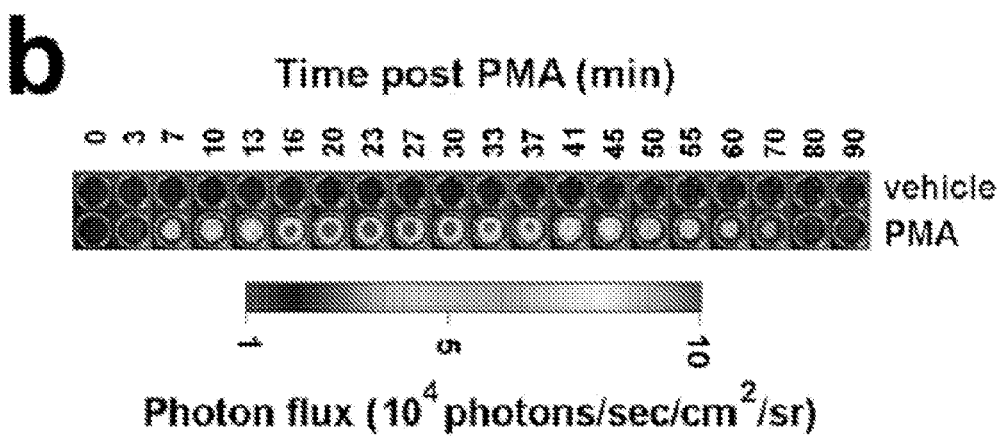
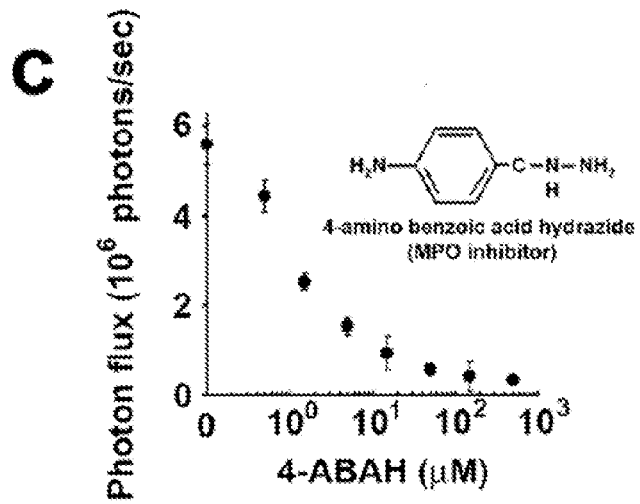

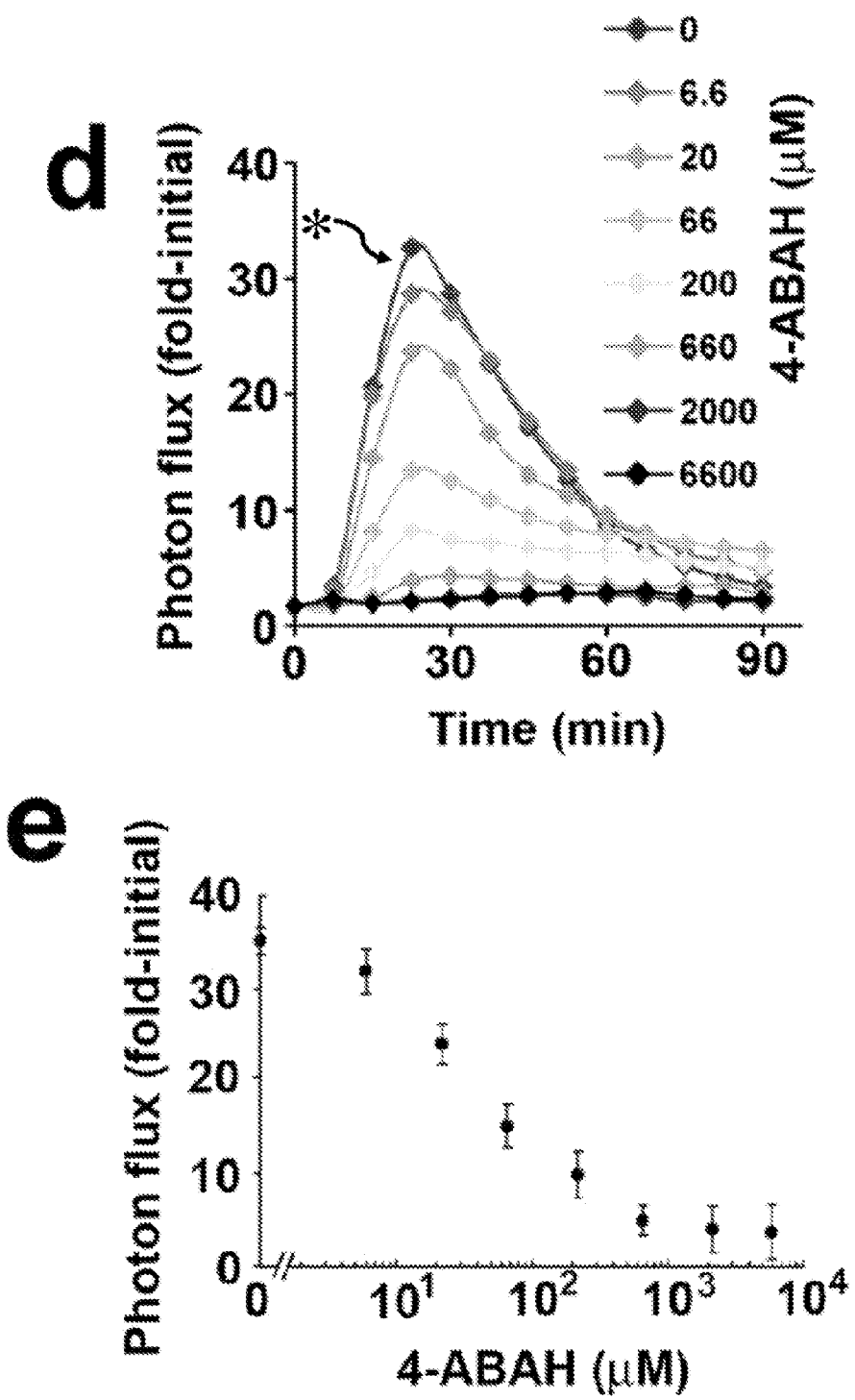
FIG. 1 D-E

FIG. 1 F-G
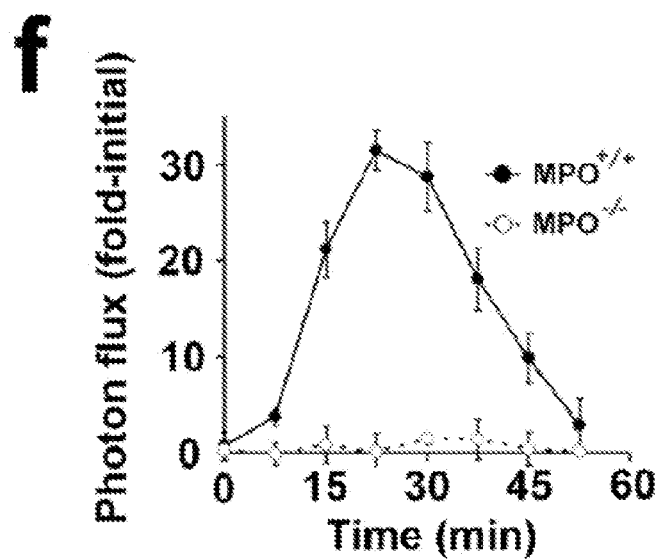
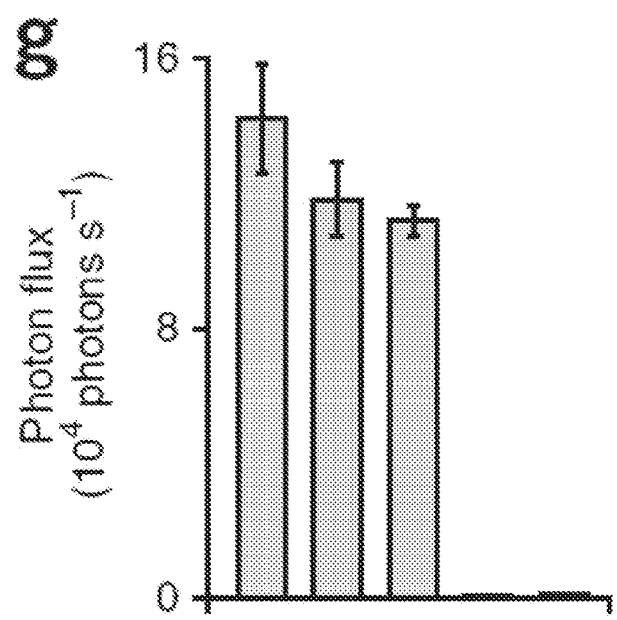

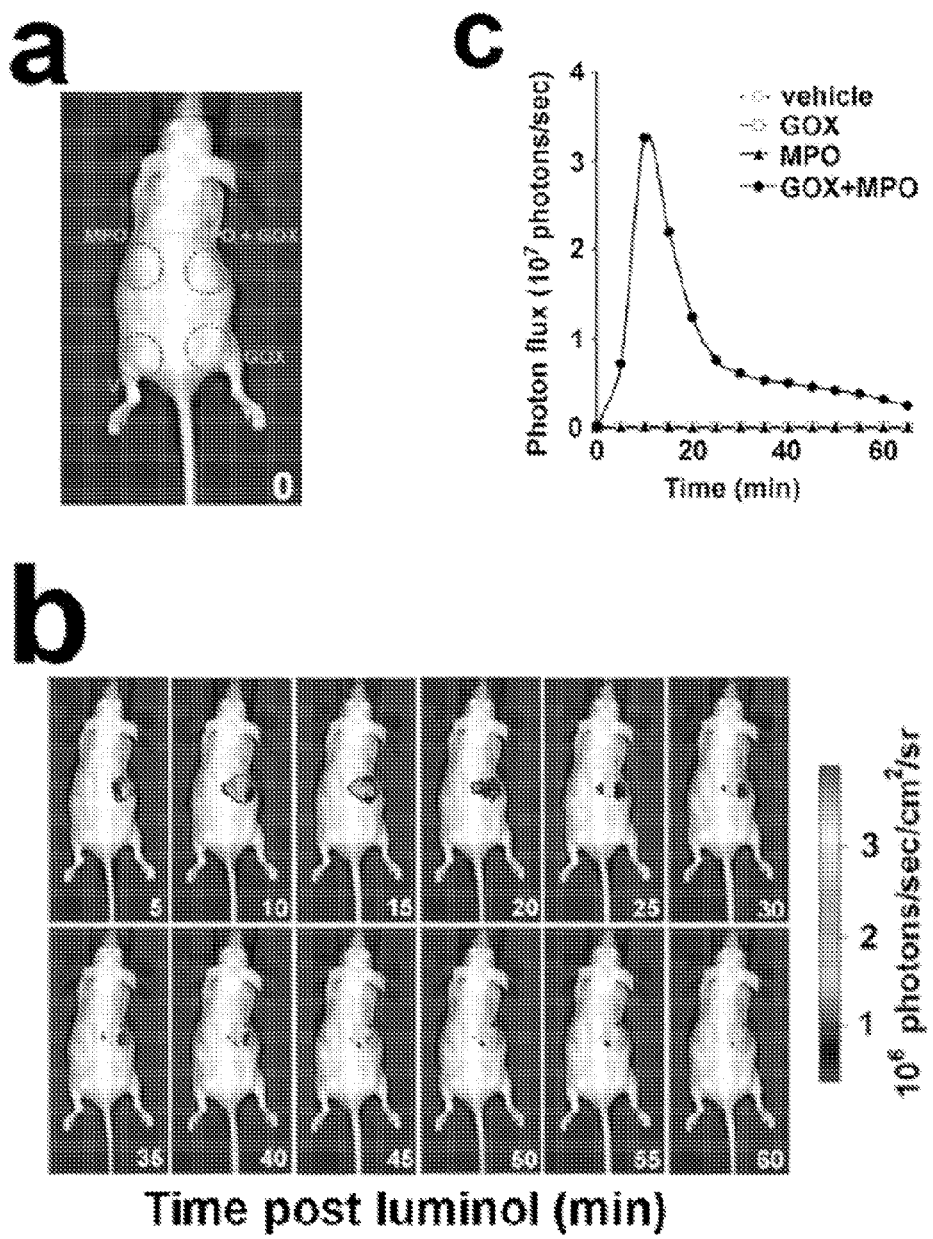

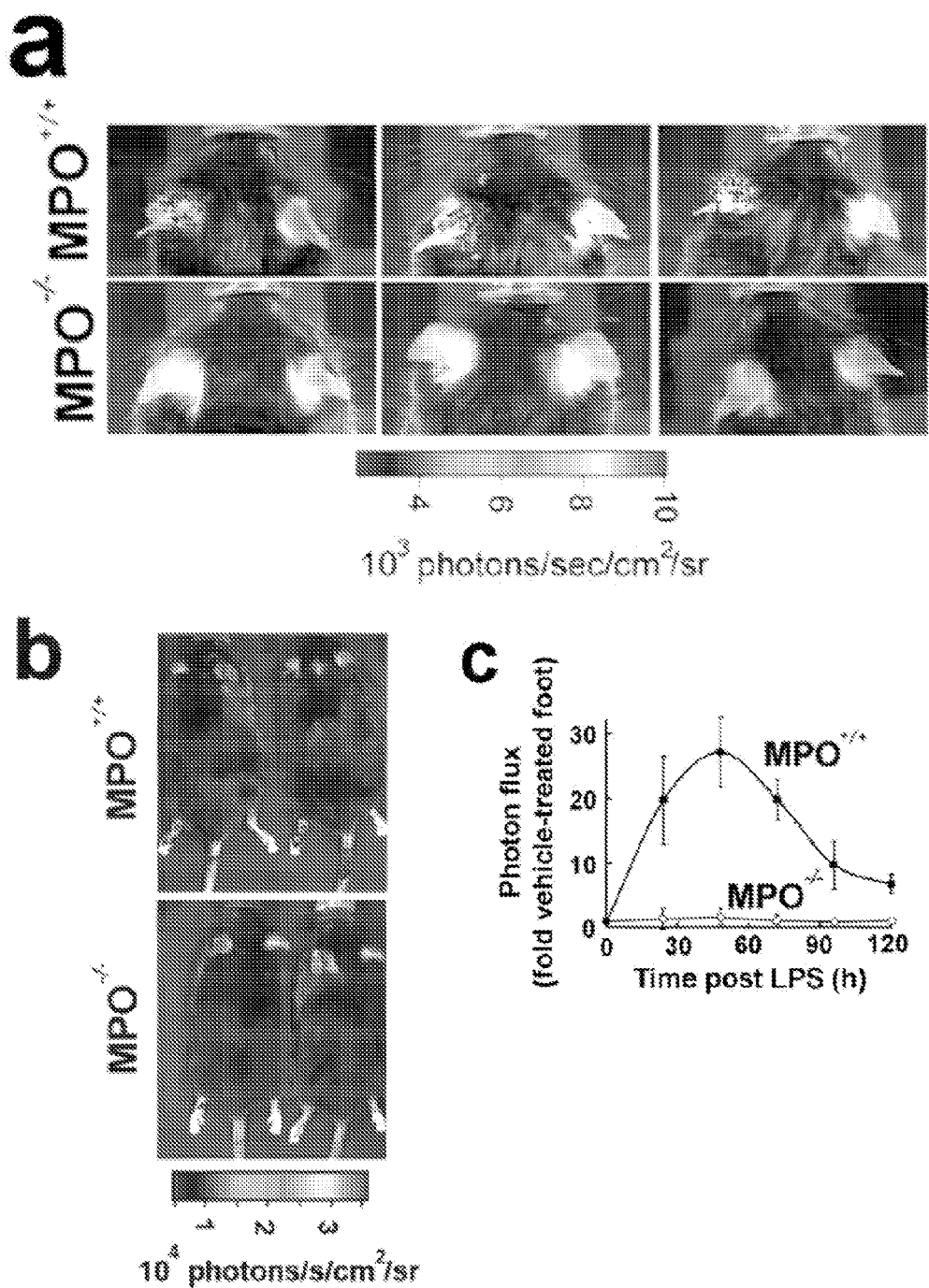
FIG. 3 A-C

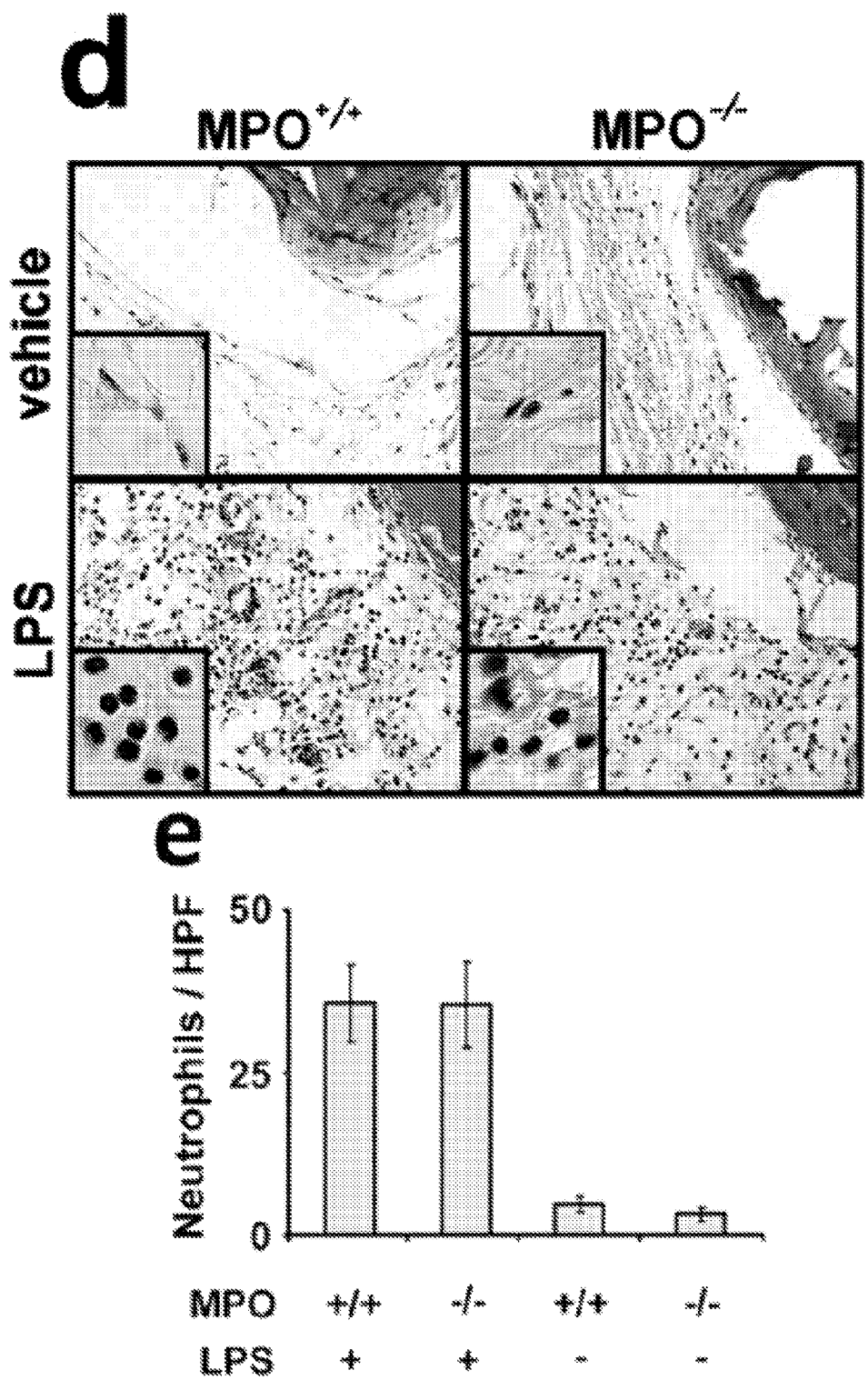
FIG. 3 D-E

FIG. 4 A-B
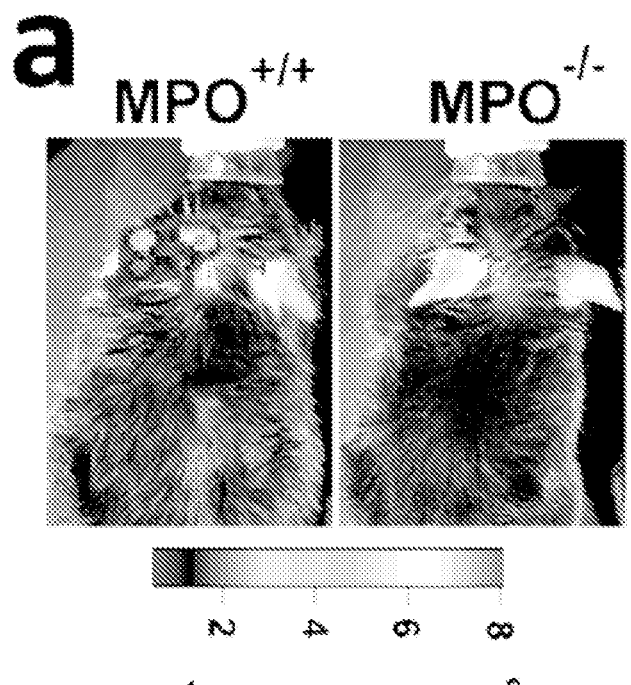
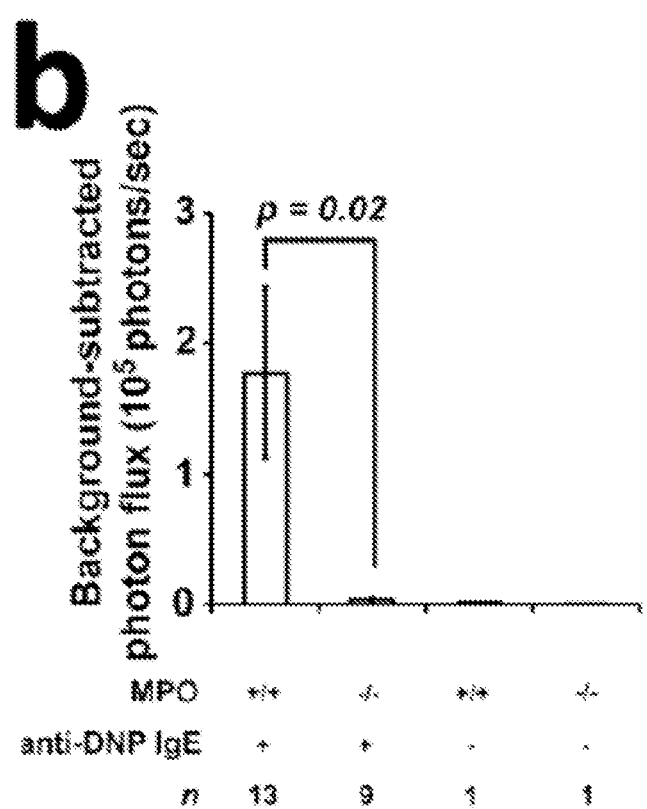

FIG. 4 C-D
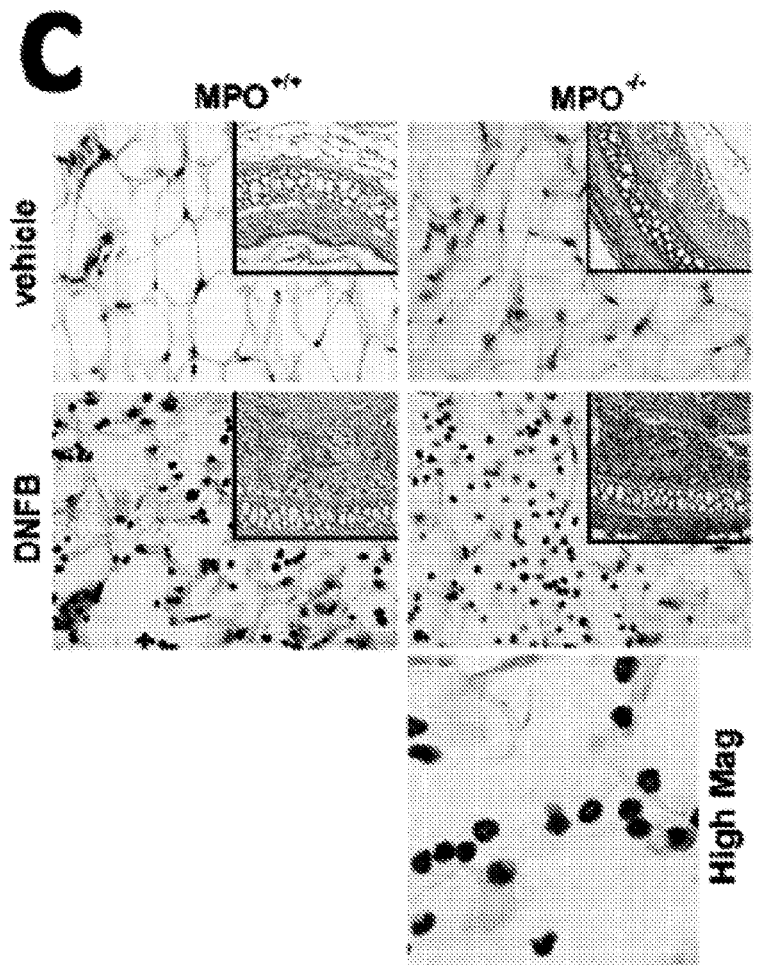
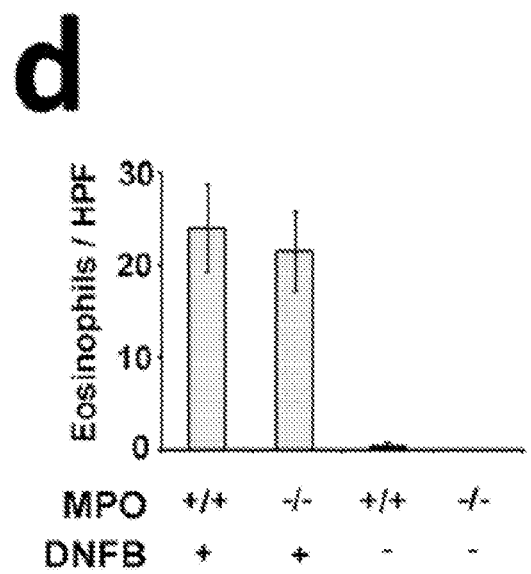

FIG. 16
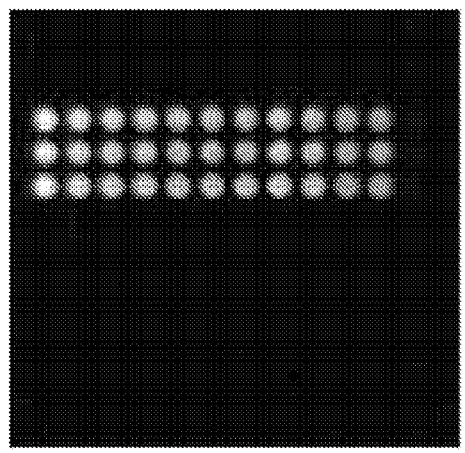
OPEN
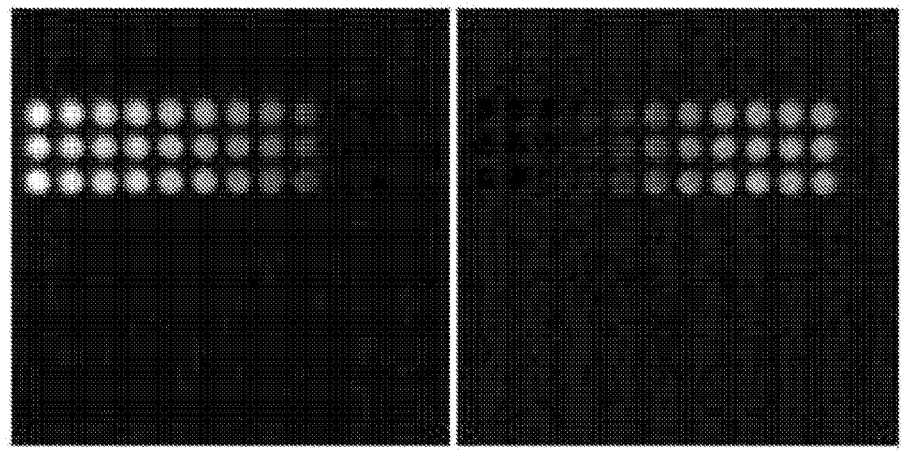
AP/CDP-Star    HRP/ILTR

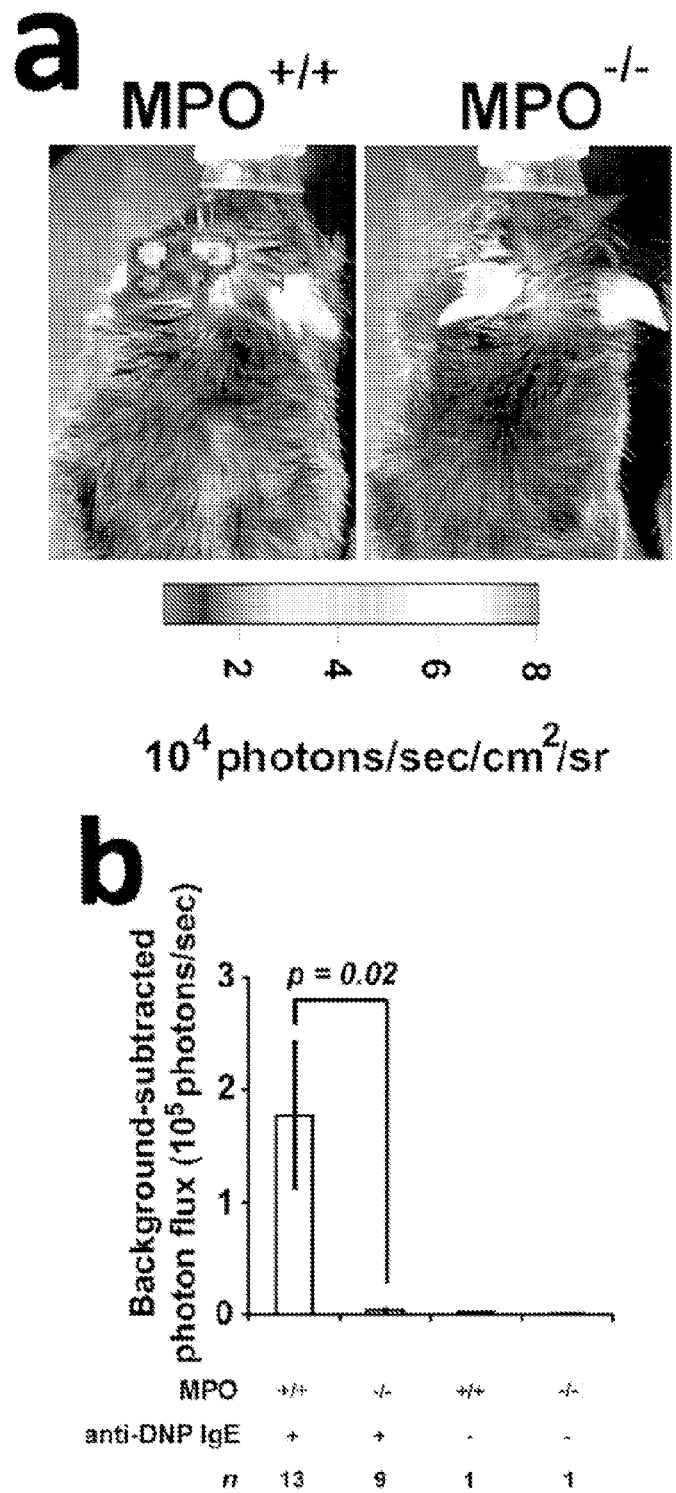
FIG. 21 A-B

FIG. 21 C-D
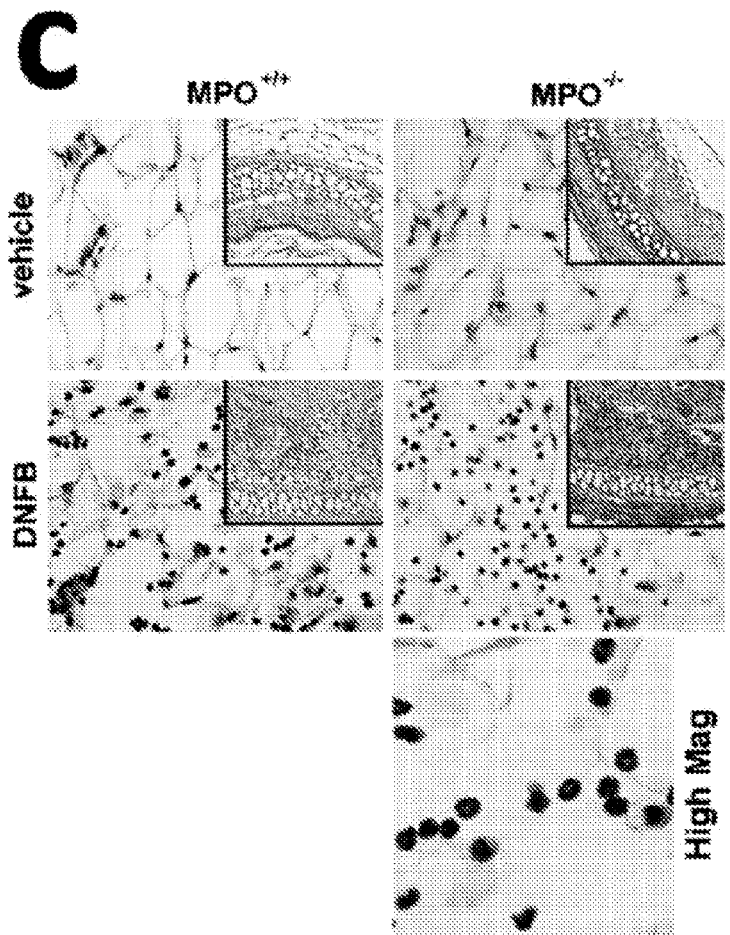
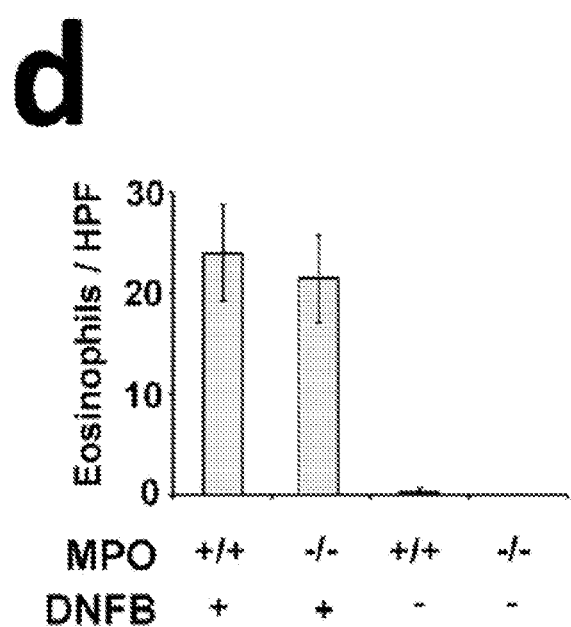

BIOLUMINESCENCE IMAGING OF MYELOPEROXIDASE ACTIVITY IN VIVO, METHODS, COMPOSITIONS AND APPARATUSES THEREFOR

CROSS-REFERENCE TO RELATED APPLICATIONS

This application claims priority from U.S. Provisional Application Ser. No. 61/110,727 filed on Nov. 3, 2008, which is incorporated herein by reference in its entirety.

STATEMENT OF GOVERNMENT SUPPORT

This invention was made with the support of government grants P50 CA94056, CA105218, CA10073, CA63417 and PO1 HL030086 from the National Institutes of Health. The government of the United States of America has certain rights in this invention.

INTRODUCTION

A need exists for diagnostic tests to aid in the characterization of subjects at risk for developing diseases characterized at least in part by high levels of MPO-mediated oxidation products and damage, in particular, cardiovascular disease. Furthermore, there is a need to establish whether a specific therapy is having the appropriate effect in individuals suffering from such conditions. Thus, prognostic indicators or biomarkers to monitor the effects of such therapy are also needed.

The heme-containing enzyme myeloperoxidase (MPO) is a key component of the cytotoxic armamentarium of phagocytic white blood cells (Heinecke, J. W., J. Lab. Clin. Med. 133, 321-325, 1999; Klebanoff, S. J., J. Leukoc. Biol. 77, 598-625, 2005; Nathan, C., Nat Rev Immunol 6, 173-182, 2006). MPO is by far the most abundant protein product in azurophilic granules of neutrophils (5%)(21), constitutes approximately 1% of monocyte protein (Bos, A., et al., Biochim Biophys Acta 525, 37-44, 1978), and can be found in the lysosomes of other polymorphonuclear leukocytes and macrophages.

Phagosomal oxidative burst is initiated by a stimulus-dependent assembly of the phagocytic NADPH oxidase (Phox), a multimeric protein complex located on the phagosomal membrane. Phox then reduces molecular oxygen to produce superoxide anion (O2.-) which further dismutates to yield the relatively unreactive hydrogen peroxide ($H_2O_2$) (Klebanoff, S. J., J. Leukoc. Biol. 77, 598-625, 2005). Upon phagocytic activation, large quantities of active MPO are secreted into phagosomes, catalyzing the production of highly bactericidal hypochlorous acid (HOCl) using H2O2 and chloride ions (Cl—) as substrates (Klebanoff, S. J., J. Leukoc. Biol. 77, 598-625, 2005) (Eq. 1 and FIG. 1 panel 1a).

$$H_2O_2 + Cl^- + H^+ \rightarrow HOCl + H_2O \quad \text{Eq. 1.}$$

Besides HOCl, MPO catalyzes the formation of other reactive molecular species such as tyrosyl radicals, aldehydes, and perhaps hydroxyl radicals (OH.) (Heinecke, J. W., J Lab Clin Med 133, 321-325, 1999; Klebanoff, S. J., J. Leukoc. Biol. 77, 598-625, 2005) and oxidizes nitric oxide (NO.) to produce nitrite (Eiserich, J. P., et al., Science 296, 2391-2394, 2002). Each of these products can directly or indirectly activate cellular signaling cascades or further react to induce cellular injury of both the invading species and host tissue. It is therefore not surprising that MPO plays an important role in the microbicidal and fungicidal activities of phagocytes (Klebanoff, S. J., J. Leukoc. Biol. 77, 598-625, 2005; Nathan, C., Nat Rev Immunol 6, 173-182, 2006; Hirche, T. O., et al., J Immunol 174, 1557-1565, 2005) and is implicated in tissue injury contributing to the pathogenesis of a variety of disorders such as rheumatoid arthritis (Bender, J. G., et al., Inflammation 10, 443-453, 1986), artherosclerosis (Bergt, C., et al., Proc. Nat'l. Acad. Sci. USA 101, 13032-13037, 2004; Shao, B., et al., Curr. Opin. Cardiol. 21, 322-328, 2006; Brennan, M. L., et al., N. Engl. J. Med. 349, 1595-1604, 2003; Zhang, R., et al., JAMA 286, 2136-2142, 2001; Heinecke, J. W. Am. J. Cardiol. 91, 12A-16A, 2003; Hazell, L. J., et al., J Clin Invest 97, 1535-1544, 1996; Heinecke, J. W. J Lab Clin Med 133, 321-325, 1999; Baldus, S., et al., Circulation 108, 1440-1445, 2003), renal glomerular injury (Malle, E., et al., Kidney hit. 64, 1956-1967, 2003), pulmonary fibrosis (Johnson, K. J., et al., J. Clin. Invest. 67, 983-993, 1981, Cantin, A. M., et al., J Clin Invest 79, 1665-1673, 1987), Alzheimer's disease (Reynolds, W. F., et al., Exp. Neurol. 155, 31-41, 19993, Green, P. S., et al., J. Neurochem. 90, 724-233, 2004), Parkinson disease (Pennathur, S., et al., J. Biol. Chem. 274, 34621-34628, 19995) and selected cancers (Reynolds, W. F., et al., Blood 90, 2730-2737, 1997; Henderson, J. P., et al., J. Biol. Chem. 278, 23522-23528, 2003; Brockmoller, J., et al., Pharmacology 61, 212-227, 2000).

Luminol (5-amino-2,3-dihydro-1,4-phthalazine-dione) is a redox-sensitive compound that emits blue luminescence (max=425 nm) when exposed to an appropriate oxidizing agent. High stability, low cost and a relatively simple synthesis has rendered luminol useful over the last century in a variety of disciplines ranging from metallurgy, analytical chemistry, biochemistry, clinical diagnostics and forensic sciences for detecting reactive intermediates. Luminol-enhanced luminescence can detect extraordinarily low concentrations of oxidizing species in complex biological systems and indeed, luminescence of isolated phagocytes and whole blood was introduced 25-30 years ago (Allen, R. C., et al., Biochem. Biophys. Res. Commun. 69, 245-252, 1976; Stevens, P., et al., Infect. Immun. 22, 41-51, 1978; Prendergast, E., et al., J. Clin. Microbiol. 13, 390-392, 1981). Luminol-enhanced luminescence provides detection methods that approach the sensitivity of radioactivity-based methods (Wampler, J. E. (1985) Chemi- and Bio-luminescence, Burr, J. G. (ed.), Marcel Dekker, New York, p. 1). Luminol-enhanced luminescence enables analyses ex vivo of the phagocytic oxidative burst upon stimulation with a myriad of soluble activators (e.g., phorbol 12-myristate 13-acetate (PMA), lipopolysaccharide (LPS), $Ca^{2+}$ ionophores or formylated bacterial peptides), opsonized particles (e.g., opsonized zymosan A (OZ)) or intact microorganisms (Hallett, M. B., et al., Methods Mol. Biol. 225, 61-67, 2003; Pavelkova, M., et al., Luminescence 19, 37-42, 2004; DeChatelet, L. R., et al., J Immunol 129, 1589-1593, 1982). Luminol-enhanced luminescence also is used clinically to screen neutrophils ex vivo for defects in oxidative metabolism such as chronic granulomatous disease (CGD)(29, 32) and MPO deficiency (Cohen, M. S., et al., Clin. Chem. 29, 513-515, 1983; Gerber, C. E., et al., Eur. J. Clin. Chem. Clin. Biochem. 34, 901-908, 1996; Carulli, G., et al., Int. J. Clin. Lab. Res. 25, 216-221, 1995).

Although luminol can react with many types of reactive oxygen species (ROS) produced during the phagocytic oxidative burst, previous studies with isolated phagocytes from normal volunteers or patients with MPO deficiency indicated that the luminol reaction is totally dependent upon MPO activity (DeChatelet, L. R., et al., J Immunol 129, 1589-1593, 1982; Bender, J. G., et al., Infect Immun 41, 1062-1070, 1983; Lundqvist, H., et al., Free Radic. Biol. Med. 20, 785-

792, 1996). However, the identity of the actual oxidizing agent and the localization of luminol oxidation (i.e., intra- or extra-cellular compartment) remain a matter of continuous debate (FIG. 1a) (DeChatelet, L. R., et al., J Immunol 129, 1589-1593, 1982; Bender, J. G., et al., Infect Immun 41, 1062-1070, 1983; Lundqvist, H., et al., Free. Radic. Biol. Med. 20, 785-792, 199631, 35-40, 1996; Brestel, E. P., Biochem Biophys Res Commun 126, 482-8, 1985; Misra, H. P., et al, Arch Biochem Biophys 215, 59-65, 1982; Dahlgren, C., et al., J Immunol Methods 232, 3-14, 1999; Jancinova, V, et al., Redox Rep 11, 110-116, 2006). FIG. 1a shows a schematic representation of the biochemical basis of luminol-BL. For example, activated neutrophils produce $H_2O_2$ via Phox-generated O2.- and MPO catalyzes the formation of HOCl from $H_2O_2$ and Cl$^-$. HOCl can directly or indirectly oxidize luminol to produce tight. Alternatively, MPO can also use superoxide anion (Misra, H. P. et al., Arch Biochem Biophys 215, 59-65, 1982; Kettle, A. J., et al., J. Biol. Chem. 269, 17146-17151, 1994) (dashed line) or other ROS (e.g., NO.) (Eiserich, J. P. et al., Science 296, 2391-2394, 2002) as substrates for peroxidase-catalyzed oxidation of luminol. Depending on the stimulus, these reactions predominately occur in the phagosome.

While enzyme-catalyzed luminescence (i.e., bioluminescence, BL) of luminol in isolated cell systems has proven useful, extrapolation to a specific readout of MPO activity in vivo is not been investigated previously since numerous competing redox reactions and compartments concurrently exist (e.g., heme mediated oxidation, eosinophil peroxidase (EPO) catalyzed generation of ROS, etc.).

The central role of MPO in acute and chronic inflammation (Klebanoff, S. J., J Leukoc Biol 77, 598-625, 2005; Nathan, C., Nat Rev Immunol 6, 173-82, 2006), as well as its pathophysiological (Shao, B., et al., Curr Opin Cardiol 21, 322-328, 2006; Heinecke, J. W. Am J Cardiol 91, 12A-16A, 2003; Heinecke, J. W. J Lab Clin Med 133, 321-325, 1999) and prognostic value (Brennan, M. L., et al., N. Engl. J. Med. 349, 1595-1604, 2003; Zhang, R., et al., JAMA 286, 2136-2142, 2001) in atherosclerosis and oncogenesis have peaked interest in imaging MPO in vivo. To date, several attempts have been made to image MPO activity using amplifiable probes by means of MRI (Jancinova, V, et al., Redox Rep 11, 110-116, 2006; Chen, J. W., et al., Man. Reason. Med. 52, 1021-1028, 2004; Quarrel, M., et al., Org. Biome. Chem. 4, 1887-1895, 2006) and single photon emission computed tomography (SPECT) (Chen, J. W., et al., Radiology 240, 473-481, 2006; Querol, S. M., et al., Mol Imaging Biol 7, 403-410, 2005). While showing some promise, these studies were limited to phantoms in vitro, MPO+GOX implants or LPS muscle injections in vivo, and the relevance of these approaches to pathophysiology remains to be established.

SUMMARY

The present inventors disclose herein methods of imaging one or more sites of a biological activity in a subject. The present disclosure sets forth methods, compounds and instruments for assessing a pathological condition associated in part with abnormal levels of MPO activity and its related oxidation products. In some aspects, the present teachings provide a methods for determining whether a subject is at risk for developing diseases associated with high levels of MPO activity, such as abscess, appendicitis, or cardiovascular disease or for assessing a subject's risk of having progressive disease, such as cardiovascular disease as may be manifested, for instance by clinical sequelae, including myocardial infarction, stroke, and peripheral vascular disease, renal disease, or renal failure. In addition, the teachings provide methods for evaluating the effectiveness of therapy with an agent useful in preventing or treating diseases such as infection or cardiovascular disease, and for establishing a prognosis in a patient suffering from a condition involving excess MPO activity, during or after treatment with agents effective in treating such conditions. In various aspects, a subject can be a mammal, such as a mouse or a human. In various aspects, imaging can comprise forming an image from photons generated from an exposed surface or beneath, up to about 1 cm, up to about 2 cm, up to about 3 cm, up to about 4 cm, or up to about 5 cm beneath an exposed surface of the subject.

The present teachings exploits the discovery that patients having coronary artery disease have significantly greater levels of MPO activity than patients without coronary artery disease. In some embodiments, the disclosed methods provide for mapping in vivo such MPO activity by non-invasive imaging, which can be used diagnostically, e.g., for localizing and assessing a pathological condition or state of inflammation. Non-limiting examples of inflammatory states which can be investigated using the disclosed methods include rheumatoid arthritis (Bender, J. G., et al., Inflammation 10, 443-453, 1986), certain ophthalmic diseases, renal glomerular injury (Malle; E., et al., Kidney Int. 64, 1956-1967, 2003), abscess, infected graft or prosthesis; or active plaque in atherosclerosis (Bergt, C., et al., Proc. Nat'l. Acad. Sci. USA 101, 13032-13037, 2004; Shao, B., et al., Curr Opin Cardiol 21, 322-328, 2006; Brennan, M. L., et al., N. Engl. J. Med. 349, 1595-604, 2003; Zhang, R., et al., JAMA 286, 2136-2142, 2001; Heinecke, J. W., Am. J. Cardiol. 91, 12A-16A, 2003; Hazell, L. J., et al., J. Clin. Invest. 97, 1535-1544, 1996; Heinecke, J. W., J Lab Clin Med 133, 321-325, 1999; Baldus, S., et al., Circulation 108, 1440-1445, 2003) or other cardiovascular diseases, or pulmonary fibrosis (Johnson, K. J., et al., J. Clin. Invest. 67, 983-993, 1981; Cantin, A. M. et al., J. Clin. Invest. 79, 1665-1673), or inflammation associated with neurological diseases such as Alzheimer's disease (Reynolds, W. F., et al., Exp Neurol 155, 31-41, 1999; Green, P. S., et al., J Neurochem 90, 724-733, 2004), Parkinson disease (Pennathur, S., et al., J. Biol. Chem. 274, 34621-34628, 1999), as well as selected cancers (Reynolds, W. F., et al., Blood 90, 2730-2737, 1997; Henderson, J. P., et al., J. Biol. Chem. 278, 23522-23528, 2003; Brockmoller, J., et al., Pharmacology 61, 212-217, 2000).

In various configurations, methods of the present teachings include administering to a subject an effective amount of a composition comprising a compound that emits light upon contact with an oxidizing agent; and imaging spatial distribution of the emitted light in the subject. In various embodiments, the methods include methods of imaging inflammation sites in a subject, methods of imaging distribution of myeloperoxidase activity in a subject, methods of imaging distribution of phagosomal oxidative activity in a subject, and methods of imaging distribution of neutrophils in a subject. In these methods, the emitted light comprises photons released as a result of a bioluminescent reaction. In some embodiments, the phagosomal oxidative activity can comprise myeloperoxidase activity. In some embodiments, the phagosomal oxidative activity can be comprised by one or more inflammatory loci. In some embodiments, the phagosomal oxidative activity can be comprised by one or more sites of neutrophil infiltration. In some embodiments, the phagosomal oxidative activity can be comprised by one or more sites of tumorigenesis. In some embodiments, the phagosomal oxidative activity can be comprised by one or more sites of inflammation. In some embodiments, the phagosomal oxidative activity can be comprised by one or more sites of skin inflammation. In some embodiments, the phagosomal oxidative activity can be comprised by one or more sites of allergic dermatitis. In some embodiments, the phagosomal oxidative activity can be comprised by one or more sites of allergic contact hypersensitivity. In some embodiments, the phagosomal oxidative activity can be comprised by one or more sites of arthritic inflammation.

In various aspects, the oxidizing agent can be a reaction product of a myeloperoxidase-catalyzed reaction, and the oxidizing agent can be HOCl. In various configurations of these methods the emitted light can have an emission intensity maximum at a wavelength ($\lambda_{max}$) of from about 380 nm to about 10 microns; from about 380 nm to about 1 microns; from about 380 nm to about 850 nm; from about 380 nm to about 750 nm; from about 400 nm to about 750 nm, about 650 nm or greater, or from about 650 nm to about 750 nm.

In various configurations, the compound can be a luminogenic-optical probe. In some configurations, the emitted light can have a $\lambda_{max}$ of about 425 nm and the compound can be 5-amino-2,3-dihydro-1,4-phthalazine-dione (luminol). In some configurations, the compound can be 6-amino-2,3-dihydro-1,4-phthalazine-dione (isoluminol). In some configurations, the emitted light can have a $\lambda_{max}$ of about 524 nm, and the compound can be Isoluminol-Oregon Green (ILOG). In some configurations, the emitted light can have $\lambda_{max}$ of about 545 nm or from about 550 nm to about 570 nm. In some configurations, the compound can be Isoluminol-Cascade Yellow (ILCY). In some configurations, the emitted light can have a $\lambda_{max}$ of about 702 nm. In some configurations, the compound can be Isoluminol-Alexa-Fluor680 (ILAF680). In some configurations, the emitted light can have a $\lambda_{max}$ of about 670 nm. In some configurations, the compound can be Isoluminol-Cy5 (ILCY5). In some configurations, the emitted light can have a $\lambda_{max}$ of about 615 nm. In some configurations, the compound can be Luminol-Glycine-Texas Red (LGTR).

In various configurations, a luminogenic-optical probe can comprise a fluorophore such as, without limitation, a fluorescein, a squaraine, a rotaxane (Johnson, J. R., et al., Angew. Chem. Int. Ed. 46, 5528-5531, 2007) a rhodamine, a Texas Red, an Oregon Green, a Cascade Yellow, a Lucifer Yellow, an AlexaFluor, a CY5, a CY3, or a quantum dot.

In various configurations, a luminogenic-optical probe can comprise a bioluminescent moiety, such as, without limitation, luminol or L-012 (8-amino-5-chloro-7-phenylpyridol[3,4-d]pyridazine-1,4-(2H,3H)dione; Daiber, A., et al., Free Radic. Biol. Med. 36: 101-111, 2004).

In various configurations of the present teachings, images can be obtained using a charge-coupled device (CCD) imaging system, which can include a cooled. CCD camera.

In various aspects, the present inventors disclose methods for spectrally unmixing chemiluminescence/bioluminescence signals emitted from a multiple luminescent substrates, such as, for example, distinguishing a signal from a substrate of horseradish peroxidase (HRP) from the chemiluminescence output of a substrate of alkaline phosphatase (AP) in in vitro assays. This approach can apply to analysis of a variety of plate assays, protein-on-chip formats, lysates and biochemical techniques such as simultaneous multiplex imaging of two proteins labeled with HRP and AP, for example, by Western blot or ELISA assays.

In various aspects of the present teachings, the inventors disclose compounds. In various configurations, these compounds can emit light when contacted by an oxidizing agent, such as in a bioluminescent reaction.

In some configurations, a compound or salt thereof can comprise a structure

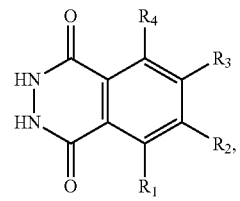

wherein at least one of $R_1$, $R_2$, $R_3$, and $R_4$ is

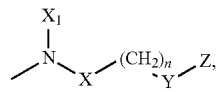

wherein $X_1$ is selected from the group consisting of H, $C_1$-$C_{20}$ alkyl, $C_1$-$C_{20}$ alkenyl, $C_1$-$C_{20}$ alkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, a nitro, a nitrile, a sulfate, a sulfide, a sulfonamide, a phosphate, a borate, and a halogen; X can be selected from the group consisting of an amino acid, a sulfonamide, $C_1$-$C_{20}$ alkyl, $C_1$-$C_{20}$ alkenyl, $C_1$-$C_{20}$ alkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an acetyl, a ketone, an aliphatic moiety comprising at least one heteroatom selected from S, P, B, N, Si, a halogen and O, and aromatic moiety comprising at least one heteroatom selected from S, P, B, N, Si, and O; X can be a linker such as an amino acid, aliphatic, or aromatic moiety; Y can be a functional group such as an amide, a sulfonamide, an acetyl, a ketone, an ester, or an ether; n can be an integer from 0 to about 20 or from 0 to about 10.

In some configurations, a compound or salt thereof can comprise a structure

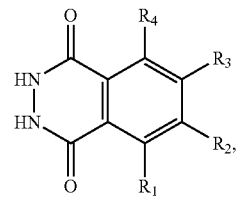

wherein $R_2$ and $R_3$ can each be selected from the group consisting of H, $C_1$-$C_{20}$ alkyl, $C_1$-$C_{20}$ alkenyl, $C_1$-$C_{20}$ alkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, a nitro, a nitrile, a sulfate, a sulfide, a sulfonamide, a phosphate, a borate, and a halogen; at least one of $R_1$ and $R_4$ can be

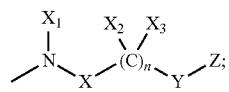

wherein $X_1$ can be selected from the group consisting of H, $C_1$-$C_{20}$ alkyl, $C_1$-$C_{20}$ alkenyl, $C_1$-$C_{20}$ alkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, a nitro, a nitrite, a sulfate, a sulfide, a sulfonamide, a phosphate, a borate, and a halogen; X can be selected from the group consisting of an amino acid, a sulfonamide, $C_1$-$C_{20}$ alkyl, $C_1$-$C_{20}$ alkenyl, $C_1$-$C_{20}$ alkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an acetyl, a ketone, an aliphatic moiety comprising at least one heteroatom selected from S, P, B, N, Si, a halogen and O, and aromatic moiety comprising at least one heteroatom selected from S, P, B, N, Si, and O; Y can be selected from the group consisting of an amide, a sulfonamide, an acetyl, a ketone, an ester, and an ether; n is an integer from 0 to about 20; each $X_2$ and $X_3$ can be selected from the group consisting of H, $C_1$-$C_{20}$ alkyl, $C_1$-$C_{20}$ alkenyl, $C_1$-$C_{20}$ alkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, a nitro, a nitrile, a sulfate, a sulfide, a sulfonamide, a phosphate, a borate and a halogen. In some configurations, an $X_2$ and an $X_3$ can together comprise an aliphatic or aromatic cyclic moiety. In some configurations, $R_2$ and $R_3$ can together comprise an aliphatic or aromatic cyclic moiety. In some configurations, one or both of $R_1$ and $R_4$ can be H.

In some configurations, a compound or salt thereof can comprise a structure.

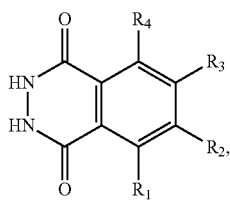

wherein $R_1$ and $R_4$ can each be selected from the group consisting of H, $C_1$-$C_{20}$ alkyl, $C_1$-$C_{20}$ alkenyl, $C_1$-$C_{20}$ alkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, a nitro, a nitrite, a sulfate, a sulfide, a sulfonamide, a phosphate, a borate, and a halogen; at least one of $R_2$ and $R_3$ can be

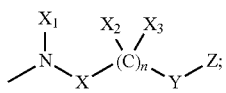

wherein $X_1$ can be selected from the group consisting of H, $C_1$-$C_{20}$ alkyl, $C_1$-$C_{20}$ alkenyl, $C_1$-$C_{20}$ alkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, a nitro, a nitrile, a sulfate, a sulfide, a sulfonamide, a phosphate, a borate, and a halogen; X can be selected from the group consisting of a $C_1$-$C_{20}$ alkyl, a $C_1$-$C_{20}$ heteroalkyl, a $C_1$-$C_{20}$ alkenyl, a $C_1$-$C_{20}$ heteroalkenyl, a $C_1$-$C_{20}$ alkynyl, a $C_1$-$C_{20}$ heteroalkynyl, a $C_1$-$C_{20}$ aryl, a $C_1$-$C_{20}$ heteroaryl, a $C_1$-$C_{20}$ carboxyl, a $C_1$-$C_{20}$ carbonyl, an ester, an ether, an amine, an amide, and a sulfonamide; Y can be selected from the group consisting of an amide, a sulfonamide, an acetyl, a ketone, an ester, and an ether; n is an integer from 0 to about 20; each $X_2$ and $X_3$ can be selected from the group consisting of H, $C_1$-$C_{20}$ alkyl, $C_1$-$C_{20}$ alkenyl, $C_1$-$C_{20}$ alkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, a nitro, a nitrile, a sulfate, a sulfide, a sulfonamide, a phosphate, a borate and a halogen. In some configurations, an $X_2$ and an $X_3$ can together comprise an aliphatic or aromatic cyclic moiety. In some configurations, $R_2$ and $R_3$ can together comprise an aliphatic or aromatic cyclic moiety. In some configurations, one or both of $R_1$ and $R_4$ can be H. In some configurations, one of $R_2$ and $R_3$ can be H.

In some configurations, a compound or a salt thereof can comprise a moiety of structure

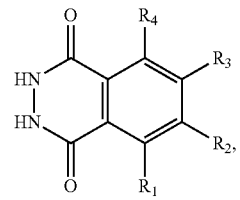

wherein at least one of $R_1$, $R_2$, $R_3$, and $R_4$ can be

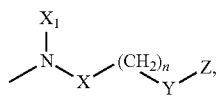

wherein $X_1$ can be H or alkyl such as $C_1$-$C_{10}$ alkyl; X can be a linker such as an amino acid, aliphatic, or aromatic moiety; Y can be a functional group such as an amide, a sulfonamide, an acetyl, a ketone, an ester, or an ether; n can be an integer from 0 to about 20 or from 0 to about 10.

In some configurations, a compound or a salt thereof can comprise a moiety of structure

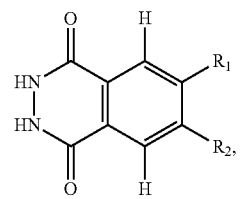

wherein at least one of $R_1$ and $R_2$ is

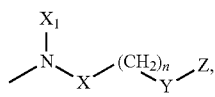

wherein $X_1$ can be H or alkyl such as $C_1$-$C_{10}$ alkyl; X can be a linker such as an amino acid, aliphatic, or aromatic moiety; Y can be a functional group such as an amide, a sulfonamide, an acetyl, a ketone, an ester, or an ether; n can be an integer from 0 to about 20 or from 0 to about 10.

In some configurations, a compound or a salt thereof can comprise a moiety of structure

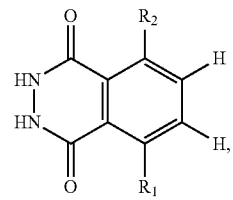

wherein at least one of $R_1$ and $R_2$ is

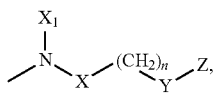

wherein $X_1$ can be H or alkyl such as $C_1$-$C_{10}$ alkyl; X can be a linker such as an amino acid, aliphatic, or aromatic moiety; Y can be a functional group such as an amide, a sulfonamide, an acetyl, a ketone, an ester, or an ether; n can be an integer from 0 to about 20 or form 0 to about 10.

In some configurations, a compound or a salt thereof can comprise a moiety of structure

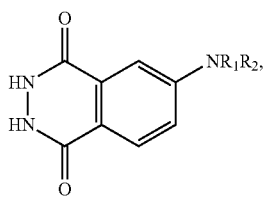

wherein each of $R_1$ and $R_2$ can be independently selected from the group consisting of H, $C_1$-$C_{10}$ alkyl and $C_1$-$C_{10}$ alkylamide, and wherein the compound emits light at a $\lambda_{max}$ longer than that of 5-Amino-2,3-dihydro-1,4-phthalazinedione (luminol) upon contact with an oxidizing agent. In various configurations, $R_2$ can be ethyl or $R_2$ can be a butylamide. In some configurations, the moiety can comprise the structure

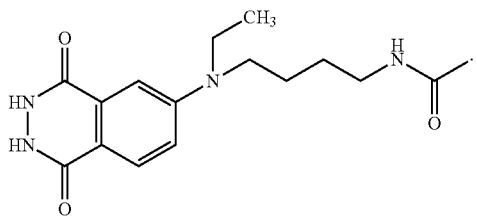

In some configurations, a compound or a salt thereof can comprise a structure

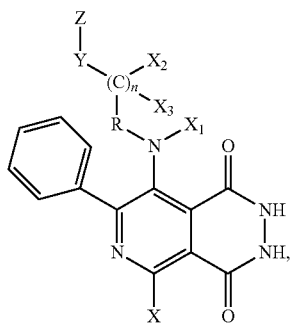

wherein X can be a halogen selected from F, Cl, Br and I; R can be selected from the group consisting of an amino acid, a sulfonamide, a $C_1$-$C_{20}$ alkyl, a $C_1$-$C_{20}$ alkenyl, a $C_1$-$C_{20}$ alkynyl, a $C_1$-$C_{20}$ aryl, a $C_1$-$C_{20}$ heteroaryl, a $C_1$-$C_{20}$ carboxyl, a $C_1$-$C_{20}$ carbonyl, an ester, an ether, an amine, an acetyl, a ketone, an aliphatic moiety comprising at least one heteroatom selected from S, P, B, N, Si, a halogen and O, an aromatic moiety comprising at least one heteroatom selected from S, P, B, N, Si, and O; Y can be selected from the group consisting of an amide, a sulfonamide, an, acetyl, a ketone, an ester, and an ether; n can be an integer from 0 to about 20; $X_2$ and $X_3$ can each be selected from the group consisting of H, a $C_1$-$C_{20}$ alkyl, a $C_1$-$C_{20}$ alkenyl, a $C_1$-$C_{20}$ alkynyl, a $C_1$-$C_{20}$ aryl, a $C_1$-$C_{20}$ heteroaryl, a $C_1$-$C_{20}$ carboxyl, a $C_1$-$C_{20}$ carbonyl, an ester, an ether, an amine, an amide, a nitro, a nitrile, a sulfate, a sulfide, a sulfonamide, a phosphate, a borate and a halogen, and wherein. Z is a fluorescent moiety. In various configurations, $X_2$ and $X_3$ can each be selected from the group consisting of an H, a $C_1$-$C_{20}$ alkyl, a $C_1$-$C_{20}$ alkenyl, a $C_1$-$C_{20}$ alkynyl, a $C_1$-$C_{20}$ aryl, a $C_1$-$C_{20}$ heteroaryl, a $C_1$-$C_{20}$ carboxyl, a $C_1$-$C_{20}$ carbonyl, an ester, an ether, an amine, an amide, a nitro, a nitrile, a sulfate, a sulfide, a sulfonamide, a phosphate, a borate and a halogen, and wherein Z is a fluorescent moiety.

In some configurations, a compound or a salt thereof can comprise a moiety of structure

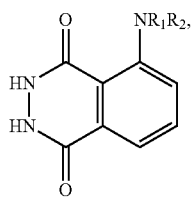

wherein each of $R_1$ and $R_2$ can be independently selected from the group consisting of H, $C_1$-$C_{10}$ alkyl and $C_1$-$C_{10}$ alkylamide, and wherein the compound emits light at a $\lambda_{max}$ longer than that of 5-Amino-2,3-dihydro-1,4-phthalazinedione (luminol) upon contact with an oxidizing agent. In various configurations, $R_2$ can be ethyl or $R_2$ can be a butylamide. In some configurations, the moiety can comprise the structure

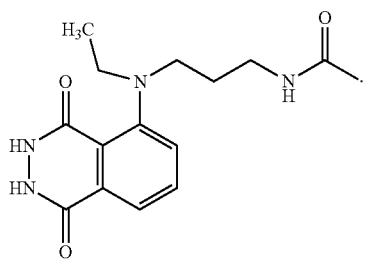

In some configurations, a compound or salt thereof can have a structure

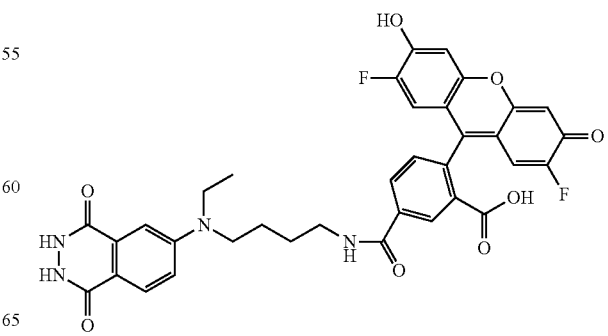

(Isoluminol-Oregon Green, ILOG).

In some configurations, a compound or salt thereof can have a structure

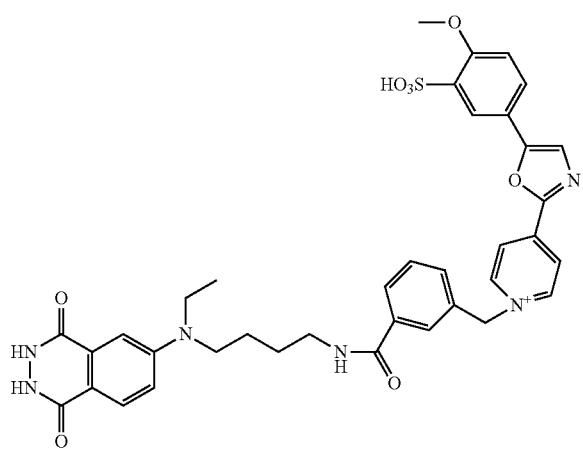 [SMILES: CCN(CCCCNC(=O)c1cccc(C[n+]2ccc(-c3ncc(-c4ccc(OC)c(S(=O)(=O)O)c4)o3)cc2)c1)c1ccc2c(=O)[nH][nH]c(=O)c2c1]

(Isoluminol-Cascade Yellow, ILCY).

In some configurations, a compound or salt thereof can have a structure

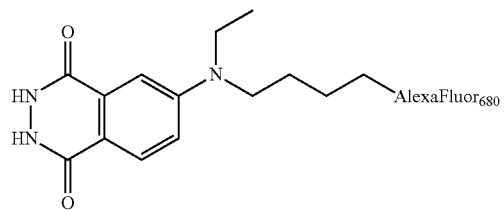

(Isoluminol-Alexa Fluor 680, ILAF680).

In some configurations, a compound or salt thereof can have a structure

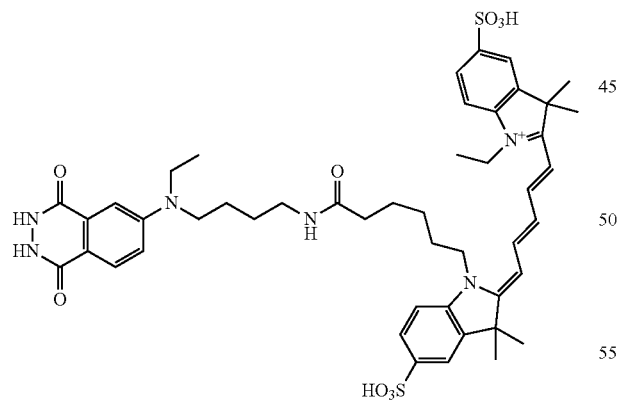

(Isoluminol-CY5, ILCY5).

The present inventors disclose herein methods of synthesizing ILOG. In various aspects, these methods can comprise mixing a first solution comprising 6-(N-(4-aminobutyl)-N-ethylamino)-2,3-dihydrophthalazine-1,4-dione and a solvent with a second solution comprising a succinimidylester of Oregon Green and an organic base. In some configurations, the solvent can be dimethylsulfoxide, and the organic base can be triethylamine.

The present inventors disclose herein methods of synthesizing ILCY. In various aspects, these methods can comprise mixing a first solution comprising 6-(N-(4-aminobutyl)-N-ethylamino)-2,3-dihydrophthalazine-1,4-dione and a solvent with a second solution comprising a succinimidylester of Cascade Yellow and an organic base. In some configurations, the solvent can be dimethylsulfoxide, and the organic base can be triethylamine.

The present inventors disclose herein methods of synthesizing ILAF680. In various aspects, these methods can comprise mixing a first solution comprising 6-(N-(4-aminobutyl)-N-ethylamino)-2,3-dihydrophthalazine-1,4-dione and a solvent with a second solution comprising a succinimidylester of AlexaFluor 680 and an organic base. In some configurations, the solvent can be dimethylsulfoxide, and the organic base can be triethylamine.

The present inventors disclose herein methods of synthesizing ILCY5. In various aspects, these methods can comprise mixing a first solution comprising 6-(N-(4-aminobutyl)-N-ethylamino)-2,3-dihydrophthalazine-1,4-dione and a solvent with a second solution comprising a succinimidylester of Cascade Yellow and an organic base. In some configurations, the solvent can be dimethylsulfoxide, and the organic base can be triethylamine.

In some configurations, a compound or salt thereof can be Luminol-Glycine-Texas Red Conjugate or a salt thereof, of structure

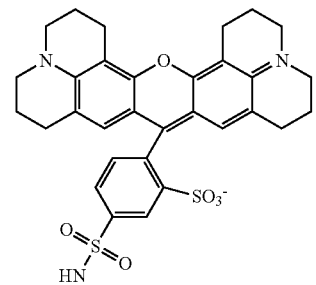
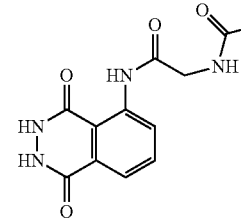

In some embodiments, synthesis of Luminol-Glycine-Texas Red Conjugate can comprise mixing a first solution comprising 2-Amino-N-(1,4-dioxo-1,2,3,4-tetrahydrophthalazine-5-yl)acetamide

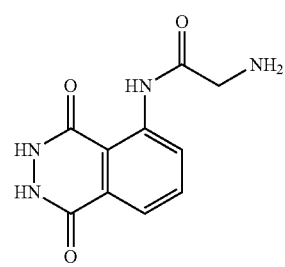 [SMILES: NCC(=O)Nc1cccc2c(=O)[nH][nH]c(=O)c12]

and a first solvent with a second solution comprising a succinimidylester of Texas Red and a second solvent. In various aspects, the first solvent can be dimethylsulfoxide, and the second solvent can be dimethylsulfoxide.

The present inventors also disclose methods of synthesizing 2-Amino-N-(1,4-dioxo-1,2,3,4-tetrahydrophthalazine-5-yl)acetamide. In various configurations, these methods can comprise forming a mixture comprising 2-Chloro-N-(1,4-dioxo-1,2,3,4-tetrahydrophthalazine-5-yl)acetamide

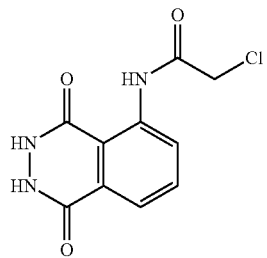 [SMILES: O=C(CCl)Nc1cccc2c(=O)[nH][nH]c(=O)c12]

and ammonium hydroxide. In some configurations, these methods can further comprise adding water to the mixture.

The present inventors also disclose methods of synthesizing 2-Chloro-N-(1,4-dioxo-1,2,3,4-tetrahydrophthalazine-5-yl)acetamide. In various configurations, these methods can comprise forming a reaction mixture comprising luminol and 2-chloro-acetylchloride. In some configurations, the reaction mixture can further comprise pyridine and acetic acid.

The present inventors also disclose methods of synthesizing a Luminol-Glycine-Texas Red Conjugate. In various configurations, these methods can comprise forming a first reaction mixture comprising 2-Chloro-N-(1,4-dioxo-1,2,3,4-tetrahydrophthalazine-5-yl)acetamide and ammonium hydroxide to yield 2-Amino-N-(1,4-dioxo-1,2,3,4-tetrahydrophthalazine-5-yl)acetamide and forming a second reaction mixture comprising the 2-Amino-N-(1,4-dioxo-1,2,3,4-tetrahydrophthalazine-5-yl)acetamide and a succinimidylester of Texas Red.

The present inventors also disclose methods of synthesizing a Luminol-Glycine-Texas Red Conjugate. In various configurations, these methods can comprise forming a first reaction mixture comprising luminol and 2-chloro-acetylchloride to yield 2-Chloro-N-(1,4-dioxo-1,2,3,4-tetrahydrophthalazine-5-yl)acetamide, forming a second reaction mixture comprising the 2-Chloro-N-(1,4-dioxo-1,2,3,4-tetrahydrophthalazine-5-yl)acetamide and ammonium hydroxide to yield 2-Amino-N-(1,4-dioxo-1,2,3,4-tetrahydrophthalazine-5-yl)acetamide, and forming a third reaction mixture comprising the 2-Amino-N-(1,4-dioxo-1,2,3,4-tetrahydrophthalazine-5-yl)acetamide and a succinimidylester of Texas Red.

The present inventors disclose herein methods of imaging one or more sites of a biological activity in a subject. In various configurations, these methods can comprise administering to the subject a composition comprising a bioluminescent compound that emits light in the near infra-red range upon contact with an enzyme having an activity at the one or more sites, or upon contact with a product of a reaction catalyzed by the enzyme at the one or more sites and obtaining an image of the emitted light. As used herein, "near-infrared bioluminescence imaging" can be defined as the detection of photons emitted from bioluminescence reactions in vivo with wavelengths greater than about 650 nm. Near-infrared can include wavelengths between about 650 nm and about 950 nm, and in some embodiments, between about 680 nm and about 850 nm.

In some aspects, the present teachings include using detectors of near infrared such as "night vision goggle" and CCD cameras. In this connection, we have used an ITT Night Vision Camera (model NQPVS14-11), we demonstrated that we could image click beetle red (CBR) bioluminescence in the liver of a mouse following somatic gene transfer and D-luciferin administration as detected by two independent observers. In vivo transfection of mouse hepatocytes was performed using the hydrodynamic method as described previously (Liu, F., et al., Gene Ther. 6, 1258-1266, 1999; Pichler, A., et al., Clin Cancer Res 11, 4487-4494, 2005). Briefly, the plasmid pCBR (1 μg) was diluted in phosphate buffered saline in a volume of 1 ml/10 g body weight and injected rapidly (5-7 sec) into tail veins of mice (BALB/C, 6 week-old males) using a 3-ml syringe fitted with a 27 g needle. Eighteen hours later, while freely ambulating after i.p. injection of D-luciferin (150 μg/g body weight), living mice were imaged for liver expression of CBR using the eyepiece of the ITT Night Vision camera. While the peak emission of CBR is 615 nm, a small fraction of the spectrum extends beyond 650 nm, i.e., into the NIR range of the spectrum. NIR bioluminescence could be readily detected emitting from the region over the liver of the live mouse in real-time with the Night Vision goggles. These experiments provide proof-of-principle that real-time bioluminescence imaging in vivo can be achieved with portable instruments.

In some aspects, the present teachings include a recording device, computer screen or video display monitor electronically coupled to the electronic output port of a Night Vision camera to display and record in real-time the NIR bioluminescence images of a subject. When the subject is a human such as a human patient, this device can be used to acquire diagnostic information in an emergency room, an operating suite or other patient care facility. For example, a detection system can be optimized for detection of red-shifted (far-red or near-infrared) spectral outputs from luminol-based bioluminescence signals.

Some embodiments of the present teachings include helmets that incorporate night vision goggles that can be worn by a caregiver such as a nurse or physician for "hands-off" visualization in patient examination rooms, such as an emergency room or operating room. In some configurations, a subject can be injected with an infrared-emitting bioluminescent compound, and bioluminescence can be detected in areas of MPO-mediated inflammation, such as an abscess or an active plaque in the carotid artery. In some configurations, real-time interaction with the subject, moving and observing the lesion can help diagnose and characterize the extent, intensity and location of the lesion.

Thus, in various aspects, BLI with luminol and luminol-conjugates provides a new tool for in vivo MPO research, high content screens, direct and indirect quantification of drug action, chemical genetic analysis and noninvasive characterization of mechanisms of disease in living organisms, animals and patients. Importantly, the safe pharmacological profile of luminol in rodents and humans (Sanders, J. M., et al., Xenobiotica 30, 263-272, 2000; Irie, S., Ther. Res. Clin. Exp. 2, 107-110, 1960) indicates that luminol and our red-shifted luminol analogues can be used as MPO-specific probes in the clinic. Novel diagnostic applications, such as noninvasive optical imaging of MPO-mediated pathology in relatively superficial structures, i.e., atherosclerotic plaques located within carotid arteries, invasive psoriatic lesions, or inflammatory eye diseases, as well as minimally invasive endoscopic evaluations can also be achieved in some embodiments of the present teachings.

In various aspects of these methods, an enzyme activity that is imaged can be a peroxidase, such as myeloperoxidase. In addition, in various configurations, the one or more sites of a biological activity can be one or more sites of inflammation, can comprise an atherosclerotic plaque, such as an acute atherosclerotic plaque. In addition, in some configurations, the one or more sites of a biological activity can comprise a carotid artery, a coronary artery, and/or peripheral vasculature. In some configurations, the one or more sites of a biological activity can comprise at least one site of vascular inflammation, such as at least one site of vascular inflammation of the eye. In some configurations, the one or more sites of a biological activity can comprise at least one site of neutrophil infiltration. In some configurations, the one or more sites of a biological activity can comprise at least one site of vascular inflammation of the brain. In some configurations, the one or more sites of a biological activity can comprise at least one tumor.

In some aspects, the methods can include obtaining at least one first image of emitted light from one or more sites of a biological activity in a subject that has received a bioluminescent compound described herein; obtaining at least one second image of the one or more sites of a biological activity by at least one second modality, and superimposing the at least one first image and the at least one second image. In some configurations, the at least one second modality can be an ultrasound image, an x-ray, a CT scan, an MRI scan, or a PET scan.

In some aspects, the present teachings include an apparatus for obtaining a near-infrared image. In various configurations, the apparatus can comprise a supercooled CCD camera which detects near infrared light, housed in a helmet.

The present teachings include disclosure of an apparatus for obtaining a near-infrared image. In various configurations, such an apparatus can comprise a supercooled CCD camera which detects near infrared light, housed in a helmet. The apparatus can be used, for example, by medical personnel such as a physician or other health care provider to observe the distribution of bioluminescence is a subject who has been administered luminol or other bioluminescent compound that emits light in the presence of a diagnostic marker such as MPO.

In various aspects, the compounds and apparatuses disclosed herein can provide tools for in vivo MPO research, high content screens, direct and indirect quantification of drug action, chemical genetic analysis and noninvasive characterization of mechanisms of disease in living organisms. In some aspects, luminol and bioluminescent molecules such as red-shifted analogues of luminol can be used clinically as MPO-specific diagnostic probes. In some configurations, luminol and luminol conjugates, in particular, luminol-glycine-fluorophore conjugates, can be used for near-infrared (NIR) imaging of MPO activity in vivo. In various configurations, such bioluminescent compounds can be used safely and non-invasively for such purposes. The present teachings thus include diagnostic applications, including noninvasive optical imaging of MPO-mediated pathology in relatively superficial structures, such as, without limitation, atherosclerotic plaques located within carotid arteries, invasive psoriatic lesions, inflammatory eye diseases, as well as minimally invasive endoscopic evaluations. Furthermore, the present teachings also include, without limitation, methods for detecting MPO activity in neutrophils and macrophages in vivo, methods for detecting PMN infiltration in tissue samples (inflammation and innate host defense mechanisms) non-invasively in vivo and ex vivo with luminol-BLI, methods for detecting acute and chronic inflammatory disorders associated with oxidative tissue damage in vivo, and methods of detecting MPO activity in acute and chronic manifestations of cardiovascular disease in vivo.

In some aspects, the present teachings disclose methods that include real-time imaging of MPO activity in living patients. In combination with "night-vision" goggles, this system can be used in real time to diagnose or aid in the diagnosis of inflammatory processes, such as, for example, appendicitis, abscess formation, inflammatory bowel disease, vasculitis, and inflammatory cancer lesions non-invasively. In some aspects, the inventors disclose using luminol and other bioluminescent molecules as therapeutic agents which can target cancers, such as cancers that are infiltrated with neutrophils or other MPO-rich cell types.

In various aspects disclosed by the inventors, a luminol-fluorophore conjugate, such as a luminol-glycine-fluorophore with red-shifted, near-infrared (NIR) emission spectrum can be used for in vivo imaging of MPO activity numerous applications. Compared to non-red-shifted bioluminescent compounds, the red-shifted spectral outputs exhibit enhanced tissue penetration and in vivo optical properties for imaging applications. In some configurations, cell assays and in vitro assays can also benefit from the red-shifted spectral properties. The various colors that can be created with the family of conjugates also permit multi-spectral analysis of multiple reactions simultaneously through spectral deconvolution analysis.

The present disclosure also includes the use of CCD cameras to detect and quantify the conversion of luminol and luminol conjugates by MPO in vivo, for example as demonstrated by the IVIS 100 system (Caliper Life Sciences, Hopkinton, Mass. USA).

The present disclosure also describes the use of standard night vision goggles to image NIR bioluminescence in vivo. In some configurations, this use can be demonstrated by the imaging of click beetle red bioluminescence in the liver of a mouse following somatic gene transfer and D-luciferin administration.

In some embodiments of the present teachings, the inventors disclose that the fluorophore Texas Red can be used as a fluorophore moiety in luminol conjugates. Furthermore, the inventors disclose that Texas Red can be resistant to degradation by MPO activity.

In some embodiments of the present teachings, the inventors disclose the use of purified MPO in, chloride-based media, bromine-based media, or other media. In various configurations, the inventors disclose using purified MPO to determine which fluorophores/nanoparticles are resistant to degradation by peroxidases, including but not limited to myeloperoxidase, eosinophil peroxidase, horseradish peroxidase, lactoperoxidases, as well as their DNA sequences, amino acid sequences, and structural homologues.

In some embodiments of the present teachings, the inventors disclose the utility of luminol and luminol conjugates for diagnosing MPO hyper- and hypo-activities in patients and pre-clinical animal models.

In some embodiments of the present teachings, the inventors disclose the utility of luminol and luminol conjugates for studying small molecule, RNA, DNA, peptide, and protein modulators of MPO activity in patients and pre-clinical animal models.

In some embodiments of the present teachings, the inventors disclose methods of synthesizing various conjugates comprising a bioluminescent moiety such as luminol and a fluorophore, such as, for example, luminol-glycine-Texas Red, luminol-glycineindocyanine green, and luminol-glycine-Quantum dot conjugates.

In some embodiments of the present teachings, the inventors disclose methods of administering bioluminescent-fluorophore conjugates, such as, without limitation, luminol-glycine-Texas Red, luminol-glycineindocyanine green, L-012-glycine-Texas Red, and luminol-glycine-Quantum dot, and L-012-glycine-Quantum dot conjugates.

In some embodiments of the present teachings, the inventors disclose the use, of the bioluminescent conjugates for spectral deconvolution of peroxidase-generated luminescent signals from alkaline phosphatase generated signals, particularly in the presence of stabilizing agents such as cyclodextrins.

In some embodiments of the present teachings, the inventors disclose the use of luminol and luminol conjugates for spectral deconvolution of peroxidase signals from green or blue luminescent signals.

The present disclosure includes the following aspects:

1. A method of imaging distribution of myeloperoxidase activity in a subject, comprising:
administering to a subject an effective amount of a composition comprising a compound that emits light upon contact with an oxidizing agent; and
imaging spatial distribution of the emitted light in the subject.

2. A method of imaging distribution of phagosomal oxidative activity in a subject, comprising:
administering to a subject an effective amount of a composition comprising a compound that emits light upon contact with an oxidizing agent; and
imaging spatial distribution of the emitted light in the subject.

3. A method of imaging inflammation sites in a subject, comprising:
administering to a subject an effective amount of a composition comprising a compound that emits light upon contact with an oxidizing agent; and
imaging spatial distribution of the emitted light in the subject.

4. A method of imaging distribution of neutrophils in a subject, comprising:
administering to a subject an effective amount of a composition comprising a compound that emits light upon contact with an oxidizing agent; and
imaging spatial distribution of the emitted light in the subject.

5. A method in accordance with aspect 1, aspect 2, aspect 3, or aspect 4 wherein the emitted light has a $\lambda_{max}$ of from about 380 nm to about 10 microns.

6. A method in accordance with aspect 1, aspect 2, aspect 3, or aspect 4 wherein the emitted light has a $\lambda_{max}$ of from about 380 nm to about 1 microns.

7. A method in accordance with aspect 1, aspect 2, aspect 3, or aspect 4 wherein the emitted light has a $\lambda_{max}$ of from about 380 nm to about 850 nm.

8. A method in accordance with aspect 1, aspect 2, aspect 3, or aspect 4 wherein the emitted light has a $\lambda_{max}$ of from about 380 nm to about 750 nm.

9. A method in accordance with aspect 1, aspect 2, aspect 3, or aspect 4 wherein the emitted light has a $\lambda_{max}$ of from about 400 nm to about 750 nm.

10. A method in accordance with aspect 1, aspect 2, aspect 3, or aspect 4 wherein the compound is a luminogenic-optical probe.

11. A method in accordance with aspect 1, aspect 2, aspect 3, or aspect 4 wherein the emitted light has a $\lambda_{max}$ of about 425 nm.

12. A method in accordance with aspect 1, aspect 2, aspect 3, or aspect 4 wherein the compound is luminol (5-amino-2,3-dihydro-1,4-phthalazine-dione).

13. A method in accordance with aspect 1, aspect 2, aspect 3, or aspect 4 wherein the emitted light has a $\lambda_{max}$ of about 650 nm or greater.

14. A method in accordance with aspect 1, aspect 2, aspect 3, or aspect 4 wherein the emitted light has a $\lambda_{max}$ of about 524 nm.

15. A method in accordance with aspect 1, aspect 2, aspect 3, or aspect 4 wherein the compound is Isoluminol-Oregon Green (ILOG).

16. A method in accordance with aspect 1, aspect 2, aspect 3, or aspect 4 wherein the emitted light has a $\lambda_{max}$ of about 550-570 nm 17. A method in accordance with aspect 1, aspect 2, aspect 3, or aspect 4 wherein the compound is Isoluminol-Cascade Yellow (ILCY).

18. A method in accordance with aspect 1, aspect 2, aspect 3, or aspect 4 wherein the emitted light has a $\lambda_{max}$ of about 702 nm.

19. A method in accordance with aspect 1, aspect 2, aspect 3, or aspect 4 wherein the compound is Isoluminol-AlexaFluor680 (ILAF680).

20. A method in accordance with aspect 1, aspect 2, aspect 3, or aspect 4 wherein the emitted light has a $\lambda_{max}$ of about 670 nm.

21. A method in accordance with aspect I, aspect 2, aspect 3, or aspect 4 wherein the compound is Isoluminol-Cy5 (ILCY5).

22. A method in accordance with aspect 1, aspect 2, aspect 3, or aspect 4 wherein the emitted light has a $\lambda_{max}$ of about 615 nm.

23. A method in accordance with aspect 1, aspect 2, aspect 3, or aspect 4 wherein the compound is Luminol-Glycine-Texas Red (LGTR).

24. A method in accordance with aspect 1, aspect 2, aspect 3, or aspect 4 wherein the oxidizing agent is a reaction product of a myeloperoxidase-catalyzed reaction.

25. A method in accordance with aspect 1, aspect 2, aspect 3, or aspect 4, wherein the oxidizing agent is HOCl.

26. A method in accordance with aspect 1, aspect 2, aspect 3, or aspect 4, wherein the imaging in the subject comprises imaging with a charge-coupled device (CCD) imaging system.

27. A method in accordance with aspect 2, wherein the phagosomal oxidative activity comprises myeloperoxidase activity.

28. A method in accordance with aspect 2, wherein the phagosomal oxidative activity is comprised by one or more inflammatory loci.

29. A method in accordance with aspect 2 wherein the phagosomal oxidative activity is comprised by one or more sites of neutrophil infiltration.

30. A method in accordance with aspect 2, wherein the phagosomal oxidative activity is comprised by one or more sites of tumorigenesis.

31. A method in accordance with aspect 2, wherein the phagosomal oxidative activity is comprised by one or more sites inflammation.

32. A method in accordance with aspect 2, wherein the phagosomal oxidative activity is comprised by one or more sites of skin inflammation.

33. A method in accordance with aspect 2, wherein the phagosomal oxidative activity is comprised by one or more sites of allergic dermatitis.

34. A method in accordance with aspect 2, wherein the phagosomal oxidative activity is comprised by one or more sites of allergic contact hypersensitivity.

35. A method in accordance with aspect 2, wherein, the phagosomal oxidative activity is comprised by one or more sites of arthritic inflammation.

36. A compound or salt thereof of structure

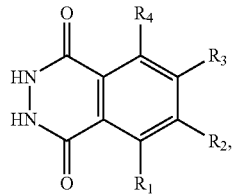

wherein $R_2$ and $R_3$ are each selected from the group consisting of H, $C_1$-$C_{20}$ alkyl, $C_1$-$C_{20}$ alkenyl, $C_1$-$C_{20}$ alkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, a nitro, a nitrile, a sulfate, a sulfide, a sulfonamide, a phosphate, a borate, and a halogen; at least one of $R_1$ and $R_4$ is

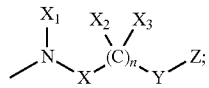

wherein $X_1$ is selected from the group consisting of H, $C_1$-$C_{20}$ alkyl, $C_1$-$C_{20}$ alkenyl, $C_1$-$C_{20}$ alkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, a nitro, a nitrile, a sulfate, a sulfide, a sulfonamide, a phosphate, a borate, and a halogen; X is selected from the group consisting of a $C_1$-$C_{20}$ alkyl, $C_1$-$C_{20}$ heteroalkyl, $C_1$-$C_{20}$ alkenyl, $C_1$-$C_{20}$ heteroalkenyl, $C_1$-$C_{20}$ alkynyl, $C_1$-$C_{20}$ heteroalkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, and a sulfonamide; Y is selected from the group consisting of an amide, a sulfonamide, an acetyl, a ketone, an ester, and an ether; n is an integer from 0 to about 20; $X_2$ and $X_3$ are each selected from the group consisting of H, $C_1$-$C_{20}$ alkyl, $C_1$-$C_{20}$ alkenyl, $C_1$-$C_{20}$ alkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, a nitro, a nitrile, a sulfate, a sulfide, a sulfonamide, a phosphate, a borate and a halogen, and wherein Z is a light-emitting moiety.

37. A compound or salt thereof in accordance with aspect 36, wherein an $X_2$ and an $X_3$ together comprise an aliphatic or aromatic cyclic moiety.

38. A compound or salt thereof in accordance with aspect 36, wherein $R_2$ and $R_3$ together comprise an aliphatic or aromatic cyclic moiety.

39. A compound or salt thereof in accordance with aspect 36, wherein Z is a fluorescent moiety.

40. A compound or salt thereof in accordance with aspect 39, wherein the fluorescent moiety is selected from the group consisting of a fluorescein; a squarane, a rotaxane, a rhodamine, a Texas Red, an Oregon. Green, a Cascade Yellow, a Lucifer Yellow, an AlexaFluor, a CY5, a CY3, and a quantum dot.

41. A compound or salt thereof of structure

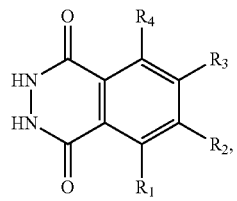

wherein $R_1$ and $R_4$ are each selected from the group consisting of H, $C_1$-$C_{20}$ alkyl, $C_1$-$C_{20}$ alkenyl, $C_1$-$C_{20}$ alkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, a nitro, a nitrile, a sulfate, a sulfide, a sulfonamide, a phosphate, a borate, and a halogen; at least one of $R_2$ and $R_3$ is

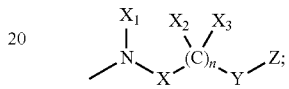

wherein $X_1$ is selected from the group consisting of H, $C_1$-$C_{20}$ alkyl, $C_1$-$C_{20}$ alkenyl, $C_1$-$C_{20}$ alkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, a nitro, a nitrile, a sulfate, a sulfide, a sulfonamide, a phosphate, a borate, and a halogen; X is selected from the group consisting of a $C_1$-$C_{20}$ alkyl, $C_1$-$C_{20}$ heteroalkyl, $C_1$-$C_{20}$ alkenyl, $C_1$-$C_{20}$ heteroalkenyl, $C_1$-$C_{20}$ alkynyl, $C_1$-$C_{20}$ heteroalkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, and a sulfonamide; Y is selected from the group consisting of an amide, a sulfonamide, an acetyl, a ketone, an ester, and an ether; n is an integer from 0 to about 20; $X_2$ and $X_3$ are each selected from the group consisting of H, $C_1$-$C_{20}$ alkyl, $C_1$-$C_{20}$ alkenyl, $C_1$-$C_{20}$ alkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, a nitro, a nitrile, a sulfate, a sulfide, a sulfonamide, a phosphate, a borate and a halogen, and wherein Z is a light-emitting moiety.

42. A compound or salt thereof in accordance with aspect 41, wherein an $X_2$ and an $X_3$ together comprise an aliphatic or aromatic cyclic moiety.

43. A compound or salt thereof in accordance with aspect 41, wherein $R_2$ and $R_3$ together comprise an aliphatic or aromatic cyclic moiety.

44. A compound or salt thereof in accordance with aspect 41, wherein Z is a fluorescent moiety.

45. A compound or salt thereof in accordance with aspect 44, wherein the fluorescent moiety is selected from the group consisting of a fluorescein, a squarane, a rotaxane, a rhodamine, a Texas Red, an Oregon Green, a Cascade Yellow, a Lucifer Yellow, an AlexaFluor, a CY5, a CY3, and a quantum dot.

46. A compound or salt thereof of structure

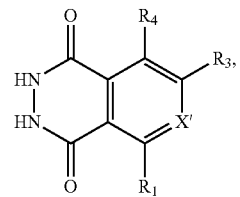

X' is a heteroatom selected from the group consisting of N, S, O, P, B, and Si; $R_1$ and $R_3$ are each independently selected from the group consisting of H, $C_1$-$C_{20}$ alkyl, $C_1$-$C_{20}$ alkenyl, $C_1$-$C_{20}$ alkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, a nitro, a nitrile, a sulfate, a sulfide, a sulfonamide, a phosphate, a borate, and a halogen; $R_4$ is

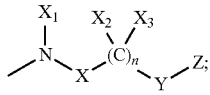

wherein $X_1$ is selected from the group consisting of H, alkyl, $C_1$-$C_{20}$ alkenyl, $C_1$-$C_{20}$ alkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, a nitro, a nitrile, a sulfate, a sulfide, a sulfonamide, a phosphate, a borate, and a halogen; X is selected from the group consisting of a $C_1$-$C_{20}$ alkyl, $C_1$-$C_{20}$ heteroalkyl, $C_1$-$C_{20}$ alkenyl, $C_1$-$C_{20}$ heteroalkenyl, $C_1$-$C_{20}$ alkynyl, $C_1$-$C_{20}$ heteroalkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, and a sulfonamide; Y is selected from the group consisting of an amide, a sulfonamide, an acetyl, a ketone, an ester, and an ether; n is an integer from 0 to about 20; $X_2$ and $X_3$ are each selected from the group consisting of H, $C_1$-$C_{20}$ alkyl, $C_1$-$C_{20}$ alkenyl, $C_1$-$C_{20}$ alkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, a nitro, a nitrile, a sulfate, a sulfide, a sulfonamide, a phosphate, a borate and a halogen, and wherein Z is a light-emitting moiety.

47. A compound or salt thereof in accordance with aspect 46, wherein an $X_2$ and an $X_3$ together comprise an aliphatic or aromatic cyclic moiety.

48. A compound or salt thereof in accordance with aspect 46, wherein $R_3$ and $R_4$ together comprise an aliphatic or aromatic cyclic moiety.

49. A compound or salt thereof in accordance with aspect 46, wherein Z is a fluorescent moiety.

50. A compound or salt thereof in accordance with aspect 49, wherein the fluorescent moiety is selected from the group consisting of a fluorescein, a squarane, a rotaxane, a rhodamine, a Texas Red, an Oregon Green, a Cascade Yellow, a Lucifer Yellow, an AlexaFluor, a CY5, a CY3, and a quantum dot.

51. A compound or salt thereof of structure

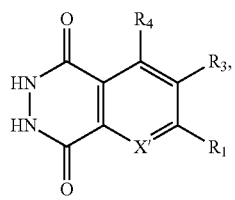

X' is a heteroatom selected from the group consisting of N, S, O, P, B, and Si; $R_1$ and $R_3$ are each independently selected from the group consisting of H, $C_1$-$C_{20}$ alkyl, $C_1$-$C_{20}$ alkenyl, $C_1$-$C_{20}$ alkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, a nitro, a nitrile, a sulfate, a sulfide, a sulfonamide; a phosphate, a borate, and a halogen; $R_4$ is

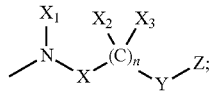

wherein $X_1$ is selected from the group consisting of H, $C_1$-$C_{20}$ alkyl, $C_1$-$C_{20}$ alkenyl, $C_1$-$C_{20}$ alkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, a nitro, a nitrile, a sulfate, a sulfide, a sulfonamide, a phosphate, a borate, and a halogen; X is selected from the group consisting of a $C_1$-$C_{20}$ alkyl, $C_1$-$C_{20}$ heteroalkyl, $C_1$-$C_{20}$ alkenyl, $C_1$-$C_{20}$ heteroalkenyl, $C_1$-$C_{20}$ alkynyl, $C_1$-$C_{20}$ heteroalkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, and a sulfonamide; Y is selected from the group consisting of an amide, a sulfonamide, an acetyl, a ketone, an ester, and an ether; n is an integer from 0 to about 20; $X_2$ and $X_3$ are each selected from the group consisting of H, $C_1$-$C_{20}$ alkyl, $C_1$-$C_{20}$ alkenyl, $C_1$-$C_{20}$ alkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, a nitro, a nitrile, a sulfate, a sulfide, a sulfonamide, a phosphate, a borate and a halogen, and wherein Z is a light-emitting moiety.

52. A compound or salt thereof in accordance with aspect 51, wherein an $X_2$ and an $X_3$ together comprise an aliphatic or aromatic cyclic moiety.

53. A compound or salt thereof in accordance with aspect 51, wherein $R_3$ and $R_4$ together comprise an aliphatic or aromatic cyclic moiety.

54. A compound or salt thereof in accordance with aspect 51, wherein $R_3$ and $R_1$ together comprise an aliphatic or aromatic cyclic moiety.

55. A compound or salt thereof in accordance with aspect 51, wherein Z is a fluorescent moiety.

56. A compound or salt thereof in accordance with aspect 55, wherein the fluorescent moiety is selected from the group consisting of a fluorescein, a squarane, a rotaxane, a rhodamine, a Texas Red, an Oregon Green, a Cascade Yellow, a Lucifer Yellow, an AlexaFluor, a CY5, a CY3, and a quantum dot.

57. A compound or salt thereof of structure

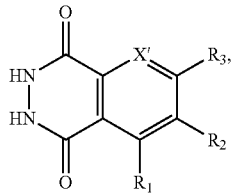

X' is a heteroatom selected from the group consisting of N, S, O, P, B, and Si; $R_1$ and $R_3$ are each independently selected from the group consisting of H, $C_1$-$C_{20}$ alkyl, $C_1$-$C_{20}$ alkenyl, $C_1$-$C_{20}$ alkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, a nitro, a nitrile, a sulfate, a sulfide, a sulfonamide, a phosphate, a borate, and a halogen; $R_2$ is

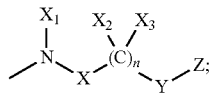

wherein $X_1$ is selected from the group consisting of H, $C_1$-$C_{20}$ alkyl, $C_1$-$C_{20}$ alkenyl, $C_1$-$C_{20}$ alkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, a nitro, a nitrile, a sulfate, a sulfide, a sulfonamide, a phosphate, a borate, and a halogen; X can be selected from the group consisting of a $C_1$-$C_{20}$ alkyl, a $C_1$-$C_{20}$ heteroalkyl, a $C_1$-$C_{20}$ alkenyl, a $C_1$-$C_{20}$ heteroalkenyl, a $C_1$-$C_{20}$ alkynyl, a $C_1$-$C_{20}$ heteroalkynyl, a $C_1$-$C_{20}$ aryl, a $C_1$-$C_{20}$ heteroaryl, a $C_1$-$C_{20}$ carboxyl, a $C_1$-$C_{20}$ carbonyl, an ester, an ether, an amine, an amide, and a sulfonamide; Y is selected from the group consisting of an amide, a sulfonamide, an acetyl, a ketone, an ester, and an ether; n is an integer from 0 to about 20; $X_2$ and $X_3$ are each selected from the group consisting of H, $C_1$-$C_{20}$ alkyl, $C_1$-$C_{20}$ alkenyl, $C_1$-$C_{20}$ alkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, a nitro, a nitrite, a sulfate, a sulfide, a sulfonamide, a phosphate, a borate and a halogen, and Wherein Z is a light-emitting moiety.

58. A compound or salt thereof in accordance with aspect 57, wherein an $X_2$ and an $X_3$ together comprise an aliphatic or aromatic cyclic moiety.

59. A compound or salt thereof in accordance with aspect 57, wherein $R_2$ and $R_3$ together comprise an aliphatic or aromatic cyclic moiety.

60. A compound or salt thereof in accordance with aspect 57, wherein $R_1$ and $R_2$ together comprise an aliphatic or aromatic cyclic moiety.

61. A compound or salt thereof in accordance with aspect 57, wherein Z is a fluorescent moiety.

62. A compound or salt thereof in accordance with aspect 61, wherein the fluorescent moiety is selected from the group consisting of a fluorescein, a squarane, a rotaxane, a rhodamine, a Texas Red, an Oregon Green, a Cascade Yellow, a Lucifer Yellow, an AlexaFluor, a CY5, a CY3, and a quantum dot.

63. A compound or salt thereof of structure

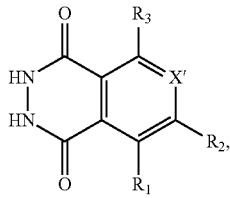

X' is a heteroatom selected from the group consisting of N, S, O, P, B, and Si; $R_2$ and $R_3$ are each independently selected from the group consisting of H, $C_1$-$C_{20}$ alkyl, $C_1$-$C_{20}$ alkenyl, $C_1$-$C_{20}$ alkynyl, $C_1$-$C_{20}$ aryl, $C_1$-$C_{10}$ heteroaryl, $C_1$-$C_{20}$ carboxyl, $C_1$-$C_{20}$ carbonyl, an ester, an ether, an amine, an amide, a nitro, a nitrile, a sulfate, a sulfide, a sulfonamide, a phosphate, a borate, and a halogen; $R_1$ is

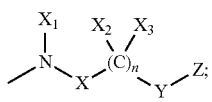

wherein $X_1$ is selected from the group consisting of H, $C_1$-$C_{20}$ alkyl, $C_1$-$C_{20}$ alkenyl, $C_1$-$C_{20}$ alkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, a nitro, a nitrile, a sulfate, a sulfide, a sulfonamide, a phosphate, a borate, and a halogen; X is selected from the group consisting of a $C_1$-$C_{20}$ alkyl, $C_1$-$C_{10}$ heteroalkyl, $C_1$-$C_{20}$ alkenyl, heteroalkenyl, $C_1$-$C_{20}$ alkynyl, $C_1$-$C_{20}$ heteroalkynyl, $C_1$-$C_{10}$ aryl, $C_1$-$C_{20}$ heteroaryl, $C_1$-$C_{20}$ carboxyl, $C_1$-$C_{20}$ carbonyl, an ester, an ether, an amine, an amide, and a sulfonamide; Y is selected from the group consisting of an amide, a sulfonamide, an acetyl, a ketone, an ester, and an ether; n is an integer from 0 to about 20; $X_2$ and $X_3$ are each selected from the group consisting of H, $C_1$-$C_{20}$ alkyl, $C_1$-$C_{20}$ alkenyl, $C_1$-$C_{20}$ alkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, a nitro, a nitrile, a sulfate, a sulfide, a sulfonamide, a phosphate, a borate and a halogen, and wherein Z is a light-emitting moiety.

64. A compound or salt thereof in accordance with aspect 63, wherein an $X_2$ and an $X_3$ together comprise an aliphatic or aromatic cyclic moiety.

65. A compound or salt thereof in accordance with aspect 63, wherein $R_1$ and $R_2$ together comprise an aliphatic or aromatic cyclic moiety.

66. A compound or salt thereof in accordance with aspect 63, wherein Z is a fluorescent moiety.

67. A compound or salt thereof in accordance with aspect 66, wherein the fluorescent moiety is selected from the group consisting of a fluorescein, a squarane, a rotaxane, a rhodamine, a Texas Red, an Oregon Green, a Cascade Yellow, a Lucifer Yellow, an AlexaFluor, a CY5, a CY3, and a quantum dot.

68. A compound or salt thereof of structure

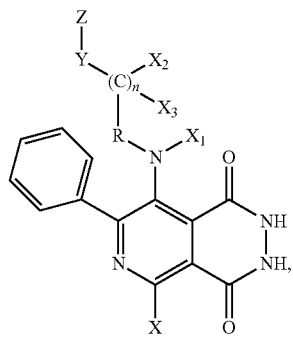

wherein X is a halogen, R is selected from the group consisting of a $C_1$-$C_{20}$ alkyl, $C_1$-$C_{20}$ heteroalkyl, $C_1$-$C_{20}$ alkenyl, $C_1$-$C_{20}$ heteroalkenyl, $C_1$-$C_{20}$ alkynyl, $C_1$-$C_{20}$ heteroalkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, and a sulfonamide; Y is selected from the group consisting of an amide, a sulfonamide, an acetyl, a ketone, an ester, and an ether; n is an integer from 0 to about 20; $X_2$ and $X_3$ are each selected from the group consisting of H, $C_1$-$C_{20}$ alkyl, $C_1$-$C_{20}$ alkenyl, $C_1$-$C_{20}$ alkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, a nitro, a nitrile, a sulfate, a sulfide, a sulfonamide, a phosphate, a borate and a halogen, and wherein Z is a light-emitting moiety.

69. A compound or salt thereof in accordance with aspect 68, wherein an $X_2$ and an $X_3$ together comprise an aliphatic or aromatic cyclic moiety.

70. A compound or salt thereof in accordance with aspect 68, wherein Z is a fluorescent moiety.

71. A compound or salt thereof in accordance with aspect 70, wherein the fluorescent moiety is selected from the group consisting of a fluorescein, a squarane, a rotaxane, a rhodamine, a Texas Red, an Oregon Green, a Cascade Yellow, a Lucifer Yellow, an AlexaFluor, a CY5, a CY3, and a quantum dot.

72. A compound comprising a moiety of structure

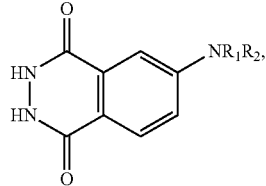

wherein each of $R_1$ and $R_2$ is independently selected from the group consisting of H, $C_1$-$C_{10}$ alkyl and $C_1$-$C_{10}$ alkylamide, and wherein the compound emits light at a $\lambda_{max}$ longer than that of 5-Amino-2,3-dihydro-1,4-phthalazinedione (luminol) upon contact with an oxidizing agent.

73. A compound in accordance with aspect 72, wherein $R_2$ is ethyl.

74. A compound in accordance with aspect 72, wherein $R_2$ is a butylamide.

75. A compound in accordance with aspect 72, wherein the moiety comprises the structure

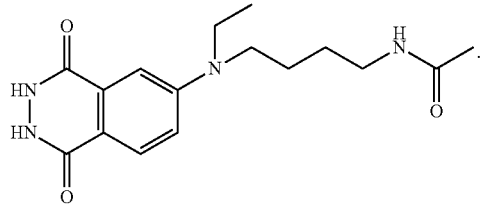 [SMILES: CCN(CCCCNC(C)=O)c1ccc2c(=O)[nH][nH]c(=O)c2c1]

76. A compound comprising a moiety of structure

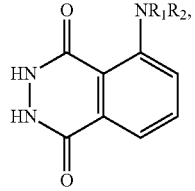

wherein each of $R_1$ and $R_2$ is independently selected from the group consisting of H, $C_1$-$C_{10}$ alkyl and $C_1$-$C_{10}$ alkylamide, and wherein the compound emits light at a $\lambda_{max}$ longer than that of 5-Amino-2,3-dihydro-1,4-phthalazinedione (luminol) upon contact with an oxidizing agent.

77. A compound in accordance with aspect 76, wherein $R_2$ is ethyl.

78. A compound in accordance with aspect 76, wherein $R_2$ is a butylamide.

79. A compound in accordance with aspect 76, wherein the moiety comprises the structure

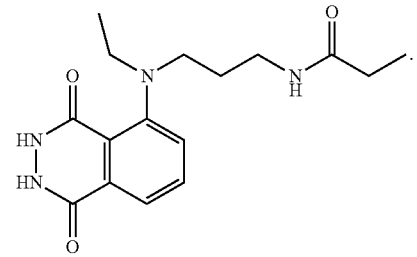 [SMILES: CCC(=O)NCCCN(CC)c1cccc2c(=O)[nH][nH]c(=O)c12]

80. A compound in accordance with aspect 72, of structure

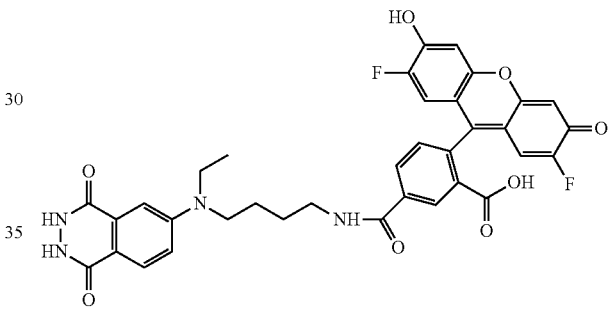

(ILOG).

81. A compound in accordance with aspect 72, of structure

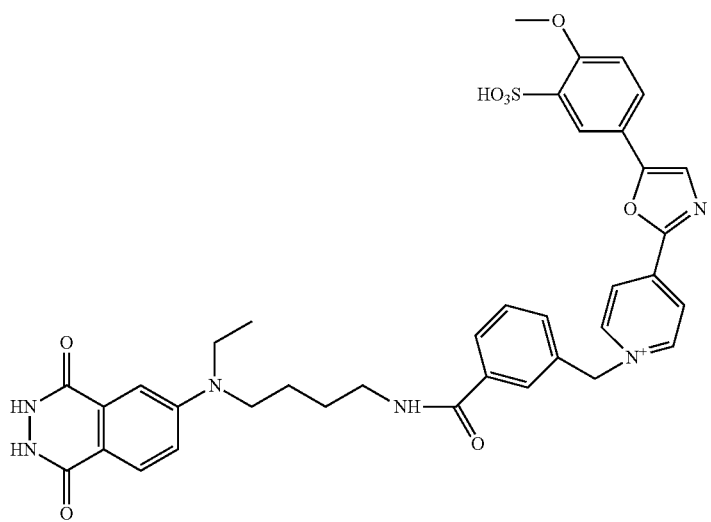 [SMILES: CCN(CCCCNC(=O)c1cccc(C[n+]2ccc(-c3ncc(-c4ccc(OC)c(S(=O)(=O)O)c4)o3)cc2)c1)c1ccc2c(=O)[nH][nH]c(=O)c2c1]

(ILCY).
82. A compound in accordance with aspect 72, of structure

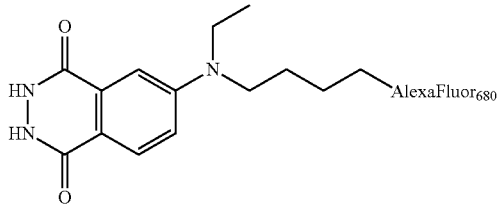

(ILAF680).
83. A compound in accordance with aspect 72, of structure

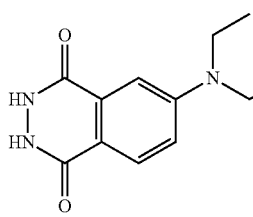

84. A method of synthesizing ILOG, comprising mixing a first solution comprising 6-(N-(4-aminobutyl)-N-ethylamino)-2,3-dihydrophthalazine-1,4-dione and a solvent with a second solution comprising a succinimidylester of Oregon Green and an organic base.

85. A method of synthesizing ILOG in accordance with aspect 84, wherein the solvent is dimethylsulfoxide.

86. A method of synthesizing ILOG in accordance with aspect 84, wherein the organic base is triethylamine.

87. A method of synthesizing ILCY, comprising mixing a first solution comprising 6-(N-(4-aminobutyl)-N-ethylamino)-2,3-dihydrophthalazine-1,4-dione and a solvent with a second solution comprising a succinimidylester of Cascade Yellow and an organic base.

88. A method of synthesizing ILCY in accordance with aspect 87, wherein the solvent is dimethylsulfoxide.

89. A method of synthesizing ILCY in accordance with aspect 87, wherein the organic base is triethylamine.

90. A method of synthesizing ILAF680, comprising mixing a first solution comprising 6-(N-(4-aminobutyl)-N-ethylamino)-2,3-dihydrophthalazine-1,4-dione and a solvent with a second solution comprising a succinimidylester of AlexaFluor 680 and an organic base.

91. A method of synthesizing ILOG in accordance with aspect 90, wherein the solvent is dimethylsulfoxide.

92. A method of synthesizing ILOG in accordance with aspect 90, wherein the organic base is triethylamine.

93. A method of synthesizing ILCY5, comprising mixing a first solution comprising 6-(N-(4-aminobutyl)-N-ethylamino)-2,3-dihydrophthalazine-1,4-dione and a solvent with a second solution comprising a succinimidylester of Cascade Yellow and an organic base.

94. A method of synthesizing ILCY5 in accordance with aspect 93, wherein the solvent is dimethylsulfoxide.

95. A method of synthesizing ILCY5 in accordance with aspect 93, wherein the organic base is triethylamine.

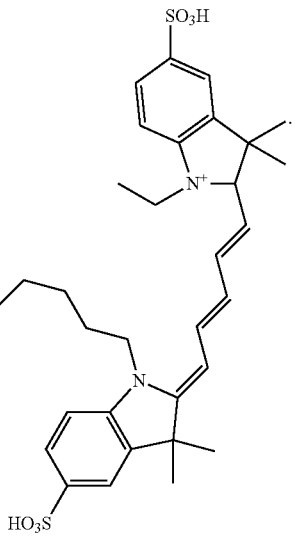

(ILCY5)

96. Luminol-Glycine-Texas Red Conjugate or a salt thereof of structure

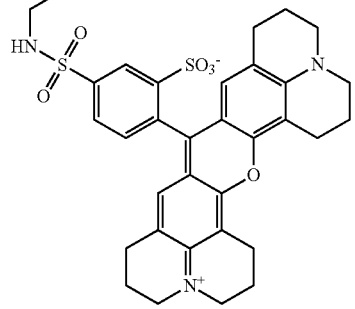

97. A method of synthesizing Luminol-Glycine-Texas Red Conjugate, comprising mixing a first solution comprising 2-Amino-N-(1,4-dioxo-1,2,3,4-tetrahydrophthalazine-5-yl) acetamide and a first solvent with a second solution comprising a succinimidylester of Texas Red and a second solvent.

98. A method of synthesizing Luminol-Glycine-Texas Red Conjugate in accordance with aspect 97, wherein the first solvent is dimethylsulfoxide.

99. A method of synthesizing Luminol-Glycine-Texas Red Conjugate in accordance with aspect 98, wherein the second solvent is dimethylsulfoxide.

100. A method of synthesizing 2-Amino-N-(1,4-dioxo-1,2,3,4-tetrahydrophthalazine-5-yl)acetamide, comprising: forming a mixture comprising 2-Chloro-N-(1,4-dioxo-1,2,3,4-tetrahydrophthalazine-5-yl)acetamide and ammonium hydroxide.

101. A method of synthesizing 2-Amino-N-(1,4-dioxo-1,2,3,4-tetrahydrophthalazine-5-yl)acetamide in accordance with aspect 100, further comprising adding water to the mixture.

102. A method of synthesizing 2-Chloro-N-(1,4-dioxo-1,2,3,4-tetrahydrophthalazine-5-yl)acetamide, comprising forming a reaction mixture comprising luminol and 2-chloro-acetylchloride.

103. A method of synthesizing 2-Chloro-N-(1,4-dioxo-1,2,3,4-tetrahydrophthalazine-5-yl)acetamide in accordance with aspect 102, wherein the reaction mixture further comprises pyridine and acetic acid.

104. A method of synthesizing a Luminol-Glycine-Texas Red Conjugate, comprising:
 forming a first reaction mixture comprising 2-Chloro-N-(1,4-dioxo-1,2,3,4-tetrahydrophthalazine-5-yl)acetamide and ammonium hydroxide to yield 2-Amino-N-(1,4-dioxo-1,2,3,4-tetrahydrophthalazine-5-yl)acetamide; and
 forming a second reaction mixture comprising the 2-Amino-N-(1,4-dioxo-1,2,3,4-tetrahydrophthalazine-5-yl) acetamide and a succinimidylester of Texas Red.

105. A method of synthesizing a Luminol-Glycine-Texas Red Conjugate, comprising:
 forming a first reaction mixture comprising luminol and 2-chloro-acetylchloride to yield 2-Chloro-N-(1,4-dioxo-1,2,3,4-tetrahydrophthalazine-5-yl)acetamide;
 forming a second reaction mixture comprising the 2-Chloro-N-(1,4-dioxo-1,2,3,4-tetrahydrophthalazine-5-yl) acetamide and ammonium hydroxide, to yield 2-Amino-N-(1,4-dioxo-1,2,3,4-tetrahydrophthalazine-5-yl)acetamide; and
 forming a third reaction mixture comprising the 2-Amino-N-(1,4-dioxo-1,2,3,4-tetrahydrophthalazine-5-yl)acetamide and a succinimidylester of Texas Red.

106. A method of imaging one or more sites of a biological activity in a subject, the method comprising:
 administering to the subject a composition comprising a bioluminescent compound that emits light in the near infrared range upon contact with an enzyme having an activity at the locus or with a product of a reaction catalyzed by the enzyme; and
 obtaining an image of the emitted light.

107. A method of imaging one or more sites of a biological activity in accordance with aspect 106, wherein the enzyme is a peroxidase.

108. A method of imaging one or more sites of a biological activity in accordance with aspect 106, wherein the enzyme is myeloperoxidase.

109. A method of imaging one or more sites of a biological activity in accordance with aspect 106, wherein the one or more sites of a biological activity is a site of inflammation.

110. A method of imaging one or more sites of a biological activity in accordance with aspect 106, wherein the one or more sites of a biological activity comprises one or more sites of inflammation.

111. A method of imaging one or more sites of a biological activity in accordance with aspect 106, wherein the one or more sites of a biological activity comprise an atherosclerotic plaque.

112. A method of imaging one or more sites of a biological activity in accordance with aspect 106, wherein the one or more sites of a biological activity comprise an acute atherosclerotic plaque.

113. A method of imaging one or more sites of a biological activity in accordance with aspect 106, wherein the one or more sites of a biological activity comprise a carotid artery.

114. A method of imaging one or more sites of a biological activity in accordance with aspect 106, wherein one or more sites of a biological activity comprise a coronary artery.

115. A method of imaging one or more sites of a biological activity in accordance with aspect 106, wherein one or more sites of a biological activity comprise peripheral vasculature.

116. A method of imaging one or more sites of a biological activity in accordance with aspect 106, wherein one or more sites of a biological activity comprise at least one site of vascular inflammation.

117. A method of imaging one or more sites of a biological activity in accordance with aspect 106, wherein the one or more sites of a biological activity comprise at least one site of vascular inflammation of the eye.

118. A method of imaging one or more sites of a biological activity in accordance with aspect 106, wherein the one or more sites of a biological activity comprise at least one site of neutrophil infiltration.

119. A method of imaging one or more sites of a biological activity in accordance with aspect 106, wherein the one or more sites of a biological activity comprise at least one site of vascular inflammation of the brain.

120. A method of imaging one or more sites of a biological activity in accordance with aspect 106, wherein the one or more sites of a biological activity comprise at least one tumor.

121. A method of imaging one or more sites of a biological activity, comprising:
 obtaining a first image of the one or more sites of a biological activity by the method of aspect 106;
 obtaining at least one second image of the one or more sites of a biological activity by at least one second modality; and
 superimposing the first image and the at least one second image.

122. A method in accordance with aspect 121, wherein the at least one second modality is selected from the group consisting of an ultrasound image, an x-ray, a CT scan, an MRI scan, and a PET scan.

123. An apparatus for obtaining a near-infrared image, comprising a supercooled CCD camera which detects near infrared light, housed in a helmet.

124. Luminol-bioluminescence imaging (luminol-BLI, including red-shifted analogues) provides new tools for in vivo MPO research, high content screens, direct and indirect quantification of drug action, chemical genetic analysis and noninvasive characterization of mechanisms of disease in living organisms.

125. Luminol and related red-shifted analogues can be used safely in the clinic as MPO-specific diagnostic probes.

126. Novel diagnostic applications of the present teachings include noninvasive optical imaging of MPO-mediated pathology in relatively superficial structures, i.e., atherosclerotic plaques located within carotid arteries, invasive psoriatic lesions, or inflammatory eye diseases, as well as minimally invasive endoscopic evaluations.

127. MPO activity in neutrophils and macrophages can be detected in vivo.

128. PMN infiltration in tissue samples (inflammation and innate host defense mechanisms) non-invasively in vivo and ex vivo can be detected using luminol-BLI.

129. Acute and chronic inflammatory disorders associated with oxidative tissue damage in vivo can be detected using bioluminescence imaging.

130. MPO activity in acute and chronic manifestations of cardiovascular disease in vivo can be detected using the bioluminescence imaging methods disclosed herein.

131. In combination with "night-vision" goggles, real-time imaging of MPO activity in living patients is described. This system can be used in real time to diagnose or aid in the diagnosis of inflammatory processes, such as appendicitis, abscess formation, inflammatory bowel disease, vasculitis, and inflammatory cancer lesions non-invasively.

132. Luminol (and red-shifted analogues) can also have therapeutic utility as a therapeutic agent targeting cancers highly infiltrated with neutrophils and other MPO-rich cell types.

133. Our novel luminol-glycine-fluorophore conjugates with red-shifted, near-infrared (NIR) emission spectra can be used for advanced in vivo imaging of MPO activity in all the applications stated above. The red-shifted spectral outputs have enhanced tissue penetration and in vivo optical properties for imaging applications. Cell assays and in vitro assays can also benefit from the red-shifted spectral properties. The various colors that can be created with the family of conjugates also permit multi-spectral analysis of multiple reactions simultaneously through spectral deconvolution analysis.

134. Luminol and luminol conjugates, in particular, luminol-glycine-fluorophore conjugates, can be used for near-infrared (NIR) imaging of MPO activity in vivo.

135. CCD cameras can be used to detect and quantify the conversion of luminol and luminol conjugates by MPO in vivo as demonstrated by the IVIS 100 (Caliper Life Sciences, Hopkinton, Mass. USA).

136. The use of standard night vision goggles to image NIR bioluminescence in vivo is demonstrated by the imaging of click beetle red bioluminescence in the liver of a mouse following somatic gene transfer and D-luciferin administration as detected by two independent observers.

137. The use of Texas Red as a fluorophore moiety in luminol conjugates and the resistance of Texas Red to degradation by MPO activity are demonstrated.

138. The use of purified MPO in chloride-based media, bromine-based media, or other media to determine which fluorophores/nanoparticles are resistant to degradation by peroxidases, including but not limited to myeloperoxidase, eosinophil peroxidase, horseradish peroxidase, lactoperoxidases, as well as their DNA sequences, amino acid sequences, and structural homologues is disclosed.

139. The utility of luminol and luminol conjugates for diagnosing MPO hyper- and hypo-activities in patients and pre-clinical animal models.

140. The use of luminol and luminol conjugates for studying small molecule, RNA, DNA, peptide, and protein modulators of MPO activity in patients and pre-clinical animal models is disclosed.

141. Methods of synthesizing any luminol-glycine-fluorophore conjugates, in particular luminol-glycine-Texas Red, luminol-glycineindocyanine green, luminol-glycine-Quantum dot conjugates, in particular, are disclosed.

142. Methods of administering any luminol-glycine-fluorophore conjugates, in, particular luminol-glycine-Texas Red, luminol-glycineindocyanine green, luminol-glycine-Quantum dot conjugates, are disclosed.

143. Use of luminol and luminol conjugates for spectral deconvolution of peroxidase-generated luminescent signals from alkaline phosphatase generated signals, particularly in the presence of stabilizing agents such as cyclodextrins, is disclosed.

144. Use of luminol and luminol conjugates for spectral deconvolution of peroxidase signals from green or blue luminescent signals is disclosed.

BRIEF DESCRIPTION OF THE DRAWINGS

FIG. 1 illustrates dependence of Luminol-BL on MPO in vitro and ex vivo

FIG. 2 illustrates Luminol-BLI of MPO/glucose oxidase (GOX) implants in vivo.

FIG. 3 illustrates lack of luminol-BL in vivo in MPO−/− mice during acute inflammatory insults.

FIG. 4 illustrates Luminol-BLI imaging of allergic contact hypersensitivity.

FIG. 16 illustrates bioluminescence and chemiluminescence outputs.

FIG. 21 illustrates induction of substantial luminol-BL bioluminescence correlating with acute contact hypersensitivity in MPO−/− mice.

DETAILED DESCRIPTION

Figure 5:
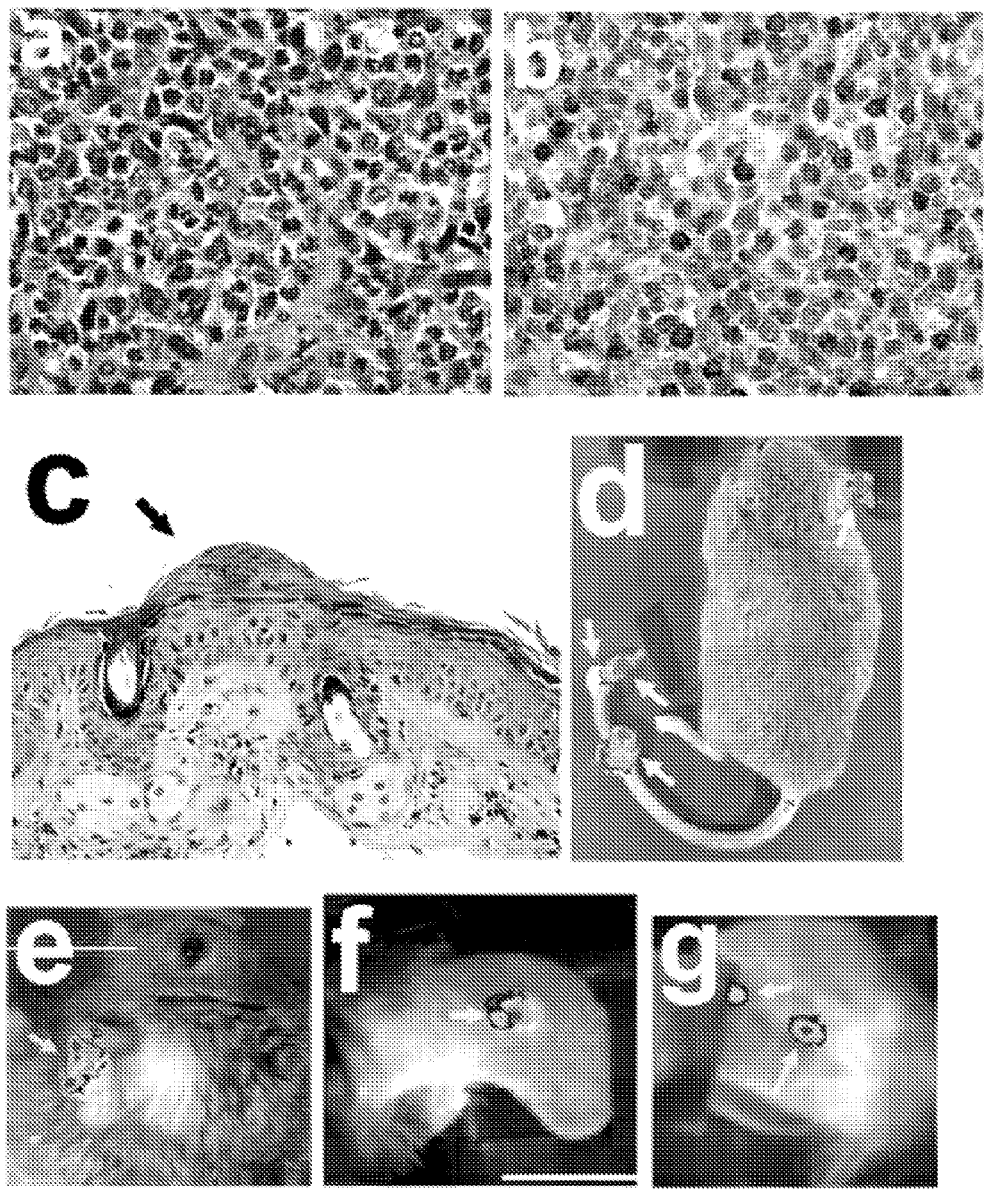
FIG. 5 illustrates Luminol-BLI imaging of spontaneous LGL tumors in GzB→Tax mice.

The present inventors disclose diagnostic methods, compositions and articles for use in the methods, and methods of chemical synthesis. In some embodiments, these diagnostic methods can be used for functionally assessing the presence of a marker of a biological activity, for example an enzymatic activity such as myeloperoxidase (MPO) activity in a living subject. A subject can be an organism such as an animal, including a mammal such as a laboratory animal (e.g., a mouse) or human.

The following Examples are intended to be illustrative of various aspects of the present teachings and are not intended to be limiting of any aspect. While some of examples may include conclusions about the way the invention may function, the inventors do not intend to be bound by those conclusions, but put them forth only as possible explanations. Unless indicated by use of past tense, presentation of an example does not imply that an experiment or procedure was, or was not, conducted, or that results were, or were not, actually obtained.

The methods and compositions described herein utilize laboratory techniques well known to skilled artisans, and can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; Ausubel, F. M., et al., ed., Current Protocols in Molecular Biology, Wiley Interscience, 2003; Nagy, A., et al., Manipulating the Mouse Embryo: A Laboratory Manual (Third Edition), Cold Spring Harbor Laboratory Press, Cold Spring Harbor, N.Y., 2003. As used in the description and the appended claims, the singular forms "a", "an" and "the" are intended to include the plural forms as well, unless the context indicates otherwise. Methods of administration of pharmaceuticals and dosage regimes can be determined according to standard principles of pharmacology well known skilled artisans, using methods provided by standard reference texts such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients, Fourth Edition, Pharmaceutical Press, 2003.

These and all other publications cited in this disclosure are incorporated herein by reference, each in its entirety.

As used in the description and the appended claims, the singular forms "a", "an" and "the" are intended to include the plural forms as well, unless the context indicates otherwise.

While MPO is central to normal host defense mechanisms, dysregulated MPO contributes to the pathogenesis of inflammatory disease states ranging from atherosclerosis to cancer. We show that upon systemic administration, the small molecule luminol and related analogues enable noninvasive, specific and highly sensitive bioluminescence imaging (BLI) of MPO activity in vivo. This can be used to assess the risk of a subject for development of a pathological condition associated with high levels of oxidative stress, in particular, cardiovascular disease. In addition, methods are described for monitoring the effectiveness of therapy in a subject, and for establishing a prognosis in a subject undergoing treatment for a condition such as a cardiac condition, using non-invasive imaging to assess MPO activity in vivo as a specific marker of oxidative stress and as an indicator of disease progression or inhibition thereof.

The myeloperoxidase (MPO) system of activated phagocytes uses hydrogen peroxide and chloride to generate hypochlorous acid, a potent bactericidal oxidant. While MPO is central to normal host defense mechanisms, dysregulated MPO contributes to the pathogenesis of inflammatory disease states ranging from atherosclerosis to cancer. Herein we show that upon systemic administration, the small molecule luminol enables noninvasive, specific and highly sensitive bioluminescence imaging (BLI) of MPO activity in vivo. Luminol-BLI allows quantitative longitudinal monitoring of MPO activity in animal models of acute dermatitis, focal arthritis and spontaneous large granular lymphocytic (LGL) tumors. Bioluminescence co-localized with histological sites of inflammation and was totally abolished in MPO−/− mice, despite massive tissue infiltration of neutrophils. Using an allergic contact hypersensitivity mouse model, we further demonstrate that activated eosinophil peroxidase (EPO) does not contribute to luminol-BLI in vivo. Strikingly, luminol-BLI detected MPO activity in sub-clinical LGL tumors, thus identifying an unexpected role for MPO in early LGL tumorigenesis. Molecular imaging of MPO activity in vivo with luminol provides a noninvasive optical readout of phagocyte activation and provides novel diagnostic applications in a wide range of acute and chronic inflammatory conditions in humans.

Luminol is relatively non-toxic, well absorbed and rapidly excreted upon systemic administration (Sanders, J. M., et al., Xenobiotica 30, 263-272, 2000). Indeed, luminol was used to treat humans suffering from alopecia areata in the 1960's (Irie, S., Curr. Ther. Res. Clin. Exp. 2, 107-110, 1960). We therefore hypothesized that systemic administration of luminol in concert with bioluminescence imaging (BLI) could serve as a sensitive and specific probe of MPO activity in intact animals. As used herein, when chemiluminescence takes place in living organisms, the phenomenon is called bioluminescence. Using, (a) BLI with purified MPO in vitro, stimulated whole blood ex vivo, three different mouse models of focal inflammation and a mouse model of eosinophil-mediated allergic contact hypersensitivity in vivo, (b) pharmacological inhibition of MPO, and (c) a genetic MPO knock-out mouse model, we demonstrate herein that luminol is a surprisingly specific and sensitive probe for MPO in vivo, enabling rapid, robust and repetitive noninvasive analysis of MPO activity in acute and chronic inflammatory states.

We used Luminol-BLI for noninvasive, specific and highly sensitive readout of MPO activity ex vivo and in vivo. By using three models of acute focal inflammation, a model of tumor-specific chronic inflammation, a genetic MPO knock-out model, pharmacological inhibition of MPO activity and an in vivo phantom model of exogenous human MPO activity, we showed that luminol-BL is robust and specific for MPO activity (both murine and human) at physiological levels in vivo. Interestingly, imaging MPO activity in MPO+GOX Matrigel implants in vivo yielded signal-to-background ratios of ~1.7 for MRI and ~2.6 for SPECT (Chen, J. W., et al., Radiology 240, 473-481, 2006; Chen, J. W., et al., Magn. Reson. Med. 52, 1021-1028, 2004; Querol, M., et al., Org. Biomol. Chem. 4, 1887-1895, 2006; Querol, S. M., et al., Mol. Imaging. Biol. 7, 403-410, 2005). In striking contrast, our observations indicate that the signal-to-background ratio exceeded 3000 for luminol-BLI (FIG. 2).

EXAMPLES

In, the Examples described herein, the following materials and methods can be used.

Luminol (sodium salt), phorbol 12-myristate 13-acetate (PMA), LPS (B-055), L-$N^G$-monomethyl arginine citrate (L-NMMA), diphenyleneiodonium (DPI), dinitrofluorobenzene (DNFB), glucose oxidase (GOX, from *Aspergillus Niger*) and murine anti-DNP IgE were purchased from Sigma-Aldrich and were of analytical purity. Luminol powder was dissolved in sterile phosphate-buffered saline (PBS) to a final concentration of 50 mg/ml and stored at −20° C. PMA was dissolved in DMSO or ethanol (1 mM or 100 µM for ex vivo or in vivo experiments, respectively). LPS was stored in sterile PBS (1 mg/ml). Human myeloperoxidase (MPO; EC 1.11.1.7) was from Calbiochem. Hydrogen peroxide ($H_2O_2$, Fisher) was freshly-prepared from a 30% stock solution (stored at 4° C. in the dark). The selective MPO inhibitor 4-aminobenzoic acid hydrazide (4-ABAH, Calbiochem) (Kettle, A. J., et al., Biochem J. 308 (Pt 2), 559-563, 1995; Kettle, A. J., et al., Biochem J 321 (Pt 2), 503-508, 1997) was prepared in DMSO (66 mM). Ewing sarcoma basement membrane matrix gel (Matrigel) was from Becton-Dickinson.

Animals

Animal protocols were approved by the Animal Studies Committee at Washington University School of Medicine. Six-month old NCr nu/nu mice were used for Matrigel-embedding of MPO and/or GOX (see below). Six-month old male $MPO^{-/-}$ mice (Brennan, M. L. et al. J Clin Invest 107, 419-430, 2001) or control ($MPO^{+/+}$) C5 7/B mice were used for BLI of PMA-induced skin inflammation, LPS-induced arthritis, contact hypersensitivity and for collection of blood for ex vivo BLI experiments. Transgenic mice expressing the HTLV-1 Tax oncogene under control of the Granzyme B promoter (GzB→Tax) (Grossman, W. J. et al., Proceedings of the National Academy of Sciences, USA 92, 1057-1062, 1995) spontaneously develop large granular lymphocytic leukemia (LGL) at 200-300 days of age. Primary tumors typically developed on earlobes, tails and limbs, presenting massive infiltration of neutrophils (Gao, L. et al., Blood 106, 4294-4302, 2005).

Bioluminescence Imaging (BLI)

For all BLI experiments (in vitro, ex vivo and in vivo), the IVIS 100 bioluminescence imaging system (Caliper) was used (f/stop, 1; no optical filter) (Gross, S. & Piwnica-Worms, D., Methods Enzymol. 399, 512-530, 2005). Exposure time, binning and field of view (FOV) are indicated for each experimental setup.

BLI Assays In Vitro

Assays were performed in colorless MEBSS buffer (mM: 4.0 HEPES, 5.4 KCl, 144 NaCl, 0.8 Na2HPO4, 1.2 CaCl2, 0.8 MgSO4, and 5.6 D-glucose, pH 7.4) in black-coated 96-well plates. To analyze the effect of 4-ABAH on luminol-BL in vitro, 10 µM of luminol were mixed with MPO (5 mU) and vehicle (MEBSS) or 4-ABAH (0-500 µM). $H_2O_2$ was then added to a final concentration of 50 µM, and ten seconds later, the plate was imaged (exposure time, 10 sec; binning, 2; FOV, 10 cm). Photon flux values±s.e.m. were plotted as a function of 4-ABAFT concentration (µM).

BLI of Whole Blood Ex Vivo

Blood was freshly drawn (100-300 µL, by jugular puncture) from $MPO^{-/-}$ or control $MPO^{+/+}$ mice. Blood was stored for up to 6 h in heparinized tubes at room temperature. Ex vivo BLI experiments using whole blood were performed in black-coated 96-well plates. Briefly, 1 µL of blood was diluted in 200 µL of MEBSS supplemented with luminol (100 µM), in the absence or presence of increasing concentrations of 4-ABAFT (0-6.6 mM), L-NMMA (1 mM) or DPI (10 µM). Samples were imaged (exposure time, 60 sec; binning, 4; FOV, 10 cm; open filter) before (t=0) and at the indicated time points after stimulation with PMA (5 µM) or vehicle (DMSO, 1 µL). Photon fluxes±s.e.m. were plotted as a function of time post PMA (min) or concentration of inhibitor.

BLI of MPO/GOX Embedded in Matrigel Implants In Vivo

Matrigel was used to immobilize human MPO and/or GOX (that produces $H_2O_2$) in vivo (Chen, J. W., et al., Radiology 240, 473-481, 2006). Briefly, GOX (30 U), MPO (20 U), vehicle (PBS) or GOX+MPO (30 and 20 U, respectively) were added to Matrigel (200 µL) at 4° C. The four different mixtures were injected subcutaneously into different locations on the back of NCr nu/nu mice. Thirty minutes later, mice were anesthetized (isoflurane inhalation), administered luminol (200 mg/kg BW, i.p.) and imaged sequentially (exposure time, 60 sec; binning, 4; FOV, 7.5 cm) every 5 minutes up to one hour. Regions of interest (ROI) were manually selected over the four implants and total photon emissions from each implant were plotted as a function of time.

BLI of PMA-Induced Dermatitis

To induce acute skin inflammation (Fretland, D. J. et al. Inflammation 19, 333-346, 1995), PMA (100 µM, 20 µL) or vehicle (ethanol) were applied topically (left and right ear, respectively) on the inner and outer surface of the earlobe of $MPO^{-/-}$ (n=5) or control (n=5) mice. Twenty-four and 48 hours later, luminol was administered (200 mg/kg BW, i.p.) and 10 min later mice were imaged (exposure time, 180 see; binning, 4; FOV, 7.5 cm) under anesthesia (isoflurane inhalation). ROI's were manually selected over the left and right ear lobes (PMA-treated and untreated, respectively) and over the central part of the skull (background). Data were expressed as (PMA—background)/(vehicle—background)± s.e.m.

BLI of LPS-Induced Acute Arthritis

Acute focal arthritis was induced by intra-articular injection of LPS (Chen, W. T., et al., Mol Imaging 3, 159-162, 2004; Esser, R. E. et al., Am. J. Pathol. 122, 323-334 1986). $MPO^{-/-}$ (n=5) or control $MPO^{+/+}$ (n=5) mice were briefly anaesthetized (isoflurane inhalation) and LPS (20 µg in 20 µL PBS) or vehicle (PBS, 20 µL) were injected into the left or right ankles, respectively, using a 30-gauge needle. Mice were administered luminol (as above) and imaged immediately after LPS administration under anesthesia (isoflurane inhalation), as well as 1, 2, 3, 4 and 5 days later (exposure time, 180 sec; binning, 4; FOV, 10 cm). ROIs were manually selected over the left and right feet (LPS-treated and untreated, respectively) and over the proximal part of the tail (background). Data were expressed as (LPS—background)/ (vehicle—background)±s.e.m. Histological specimens were prepared from both left and right ankles of a similar cohort of $MPO^{-/-}$ or control $MPO^{+/+}$ mice 48 hours after intra-articular injection of LPS or vehicle (see above). Specimens were paraformaldehyde-fixed (4%), de-calcified (10 days in 14% EDTA), paraffin-embedded, sectioned (5 µm) and stained with hematoxylin and, eosin (H&E). For each condition, neutrophils were counted in 5 high-power fields (HPF, magnification ×400).

BLI of Allergic Contact Hypersensitivity

Allergic dermatitis manifested by erythema, edema and extensive infiltration of eosinophils and neutrophils was induced by passive immunization with anti-dinitrophenol (DNP) IgE and topical challenge with dinitrofluorobenzene (DNFB) (Ray, M., et al., J Immunol 131, 1096-1102, 1983). Briefly, murine anti-DNP IgE (20 µg in 100 µl, Sigma-Aldrich) was injected intravenously into 13 $MPO^{+/+}$ and 9 $MPO^{-/-}$ mice. One control mouse of each genetic MPO background was injected with vehicle (saline) only. Twenty-four hours later, all left ears were painted with DNFB (0.2% in acetone:olive oil, 1:3) and all right ears were painted with vehicle (acetone:olive oil, 1:3). On the next day, all mice were imaged following luminol administration (200 mg/kg BW, i.p.). Mice were euthanized immediately after imaging and histological specimens were prepared from both left and right ears by fixation with paraformaldehyde (4%), de-calcification (24 h in 14% EDTA), paraffin-embedding, sectioning (5

μm) and staining with H&E. For each condition, eosinophils were counted in 5 HPF (magnification ×400).

BLI of MPO Activity in Spontaneous, Tax-Induced LGL Tumors

GzB→Tax mice were monitored for tumorigenesis on ears, limbs and tails by visual examination and palpation, weekly, for 200-300 days after birth. Ten mice with visible tumors at various sizes (1-8 mm in diameter) and locations were administered luminol (200 mg/kg BW, i.p.) and imaged (exposure time, 300 sec; binning, 4; FOV, 10 cm) under anesthesia (isoflurane inhalation). Tumors were excised, fixed in paraformaldehyde (4%), paraffin-embedded, sectioned (5 μm) and stained with H&E or immuno-stained for MPO (see below).

Immunohistochemistry (MPO and Br—Y)

Sectioned specimens were re-hydrated in graded xylene and ethanol (100%, 90% and 70% sequentially) according to standard procedures. Endogenous peroxidase activity was quenched with $H_2O_2$ (3% in PBS) for 15 min. Slides were probed for MPO using rabbit polyclonal antibody cross-reactive to both human and mouse MPO (AbCam, 1:10 dilution in PBS+1% BSA, overnight, 4° C.), followed by washing (PBS, ×3) and incubation with anti-rabbit antibody conjugated to horseradish peroxidase (HRP) (Amersham Bioscience, 1:500 dilution) and diaminobenzidine (DAB). Hematoxylin was used as a counter-stain.

Bromotyrosine adducts in sectioned mouse ears were detected using anti-dibromotyrosine monoclonal antibody (Cosmo Bio, 1:10 dilution) and the Vector M.O.M. Immunodetection Kit (Vector Laboratories) according to the manufacturer's instructions with minor modifications. Briefly, re-hydrated sections were incubated for 2 hours with twice the recommended concentration of Mouse Ig Blocking Reagent before incubation with primary antibody. The HRP-conjugated secondary antibody was visualized with DAB (1 min exposure) and the tissue counter-stained with hematoxylin. No significant staining was observed in specimens of treated ears in the absence of primary antibody (data not shown).

Example 1

This Example illustrate the synthesis of Luminogenic-Optical Probe ILOG.

Figure 6:
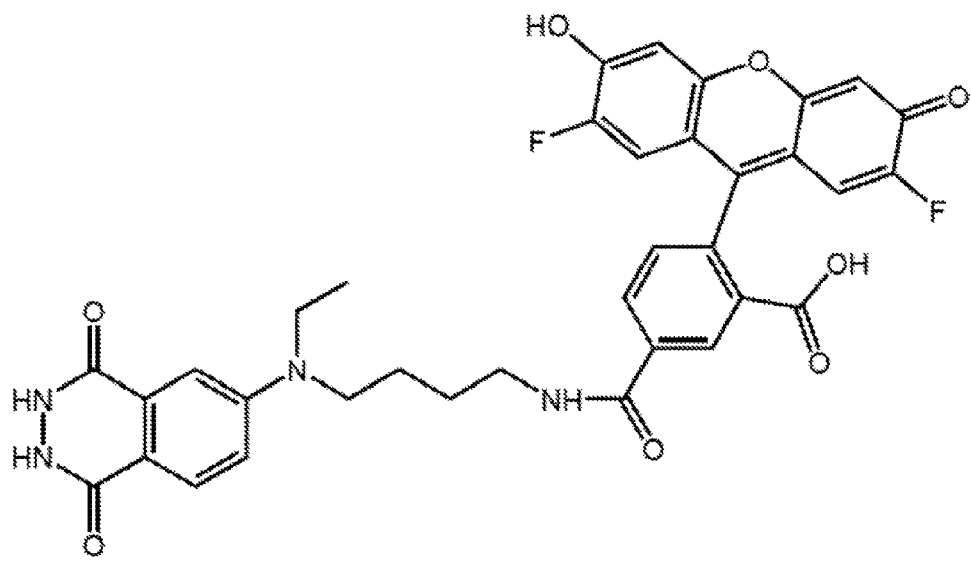
FIG. 6 illustrates chemical structure of IL-Oregon Green (ILOG).
Figure 7:
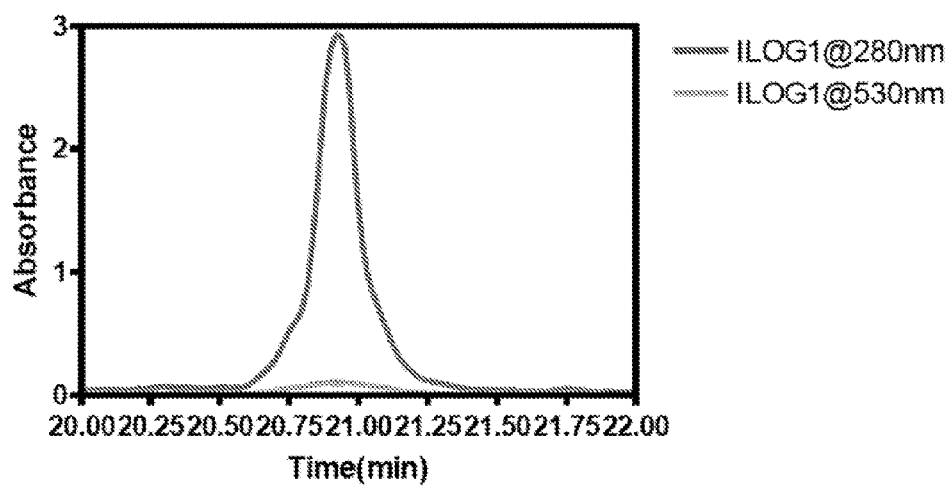
FIG. 7 illustrates HPLC data for IL-Oregon. Green (ILOG).

6-(N-(4-aminobutyl)-N-ethylamino)-2,3-dihydrophthalazine-1,4-dione (IL) dissolved in dimethylsulfoxide (0.5 ml) was treated with the succinimidylester of Oregon Green (1.1 equivalents) in the presence of trimethylamine (100 equivalents) at room temperature. Contents were stirred in an amber colored vial overnight. The product was purified on a Water's HPLC equipped with a dual wavelength detector, using an RP-C18 (Vydac) column, employing a mobile phase gradient of 2-90% acetonitrile with 0.1% TFA in water over 30 minutes. The fraction eluting at $R_f$=20.8 min was collected, lyophilized to obtain orange-red solid and identified via ESMS; Calcd for $C_{35}H_{28}F_2N_4O_8$, 670.2; Found; 670.9 (FIG. 6, FIG. 7).

Example 2

This Example illustrate the synthesis of Luminogenic-Optical Probe ILCY.

Figure 8:
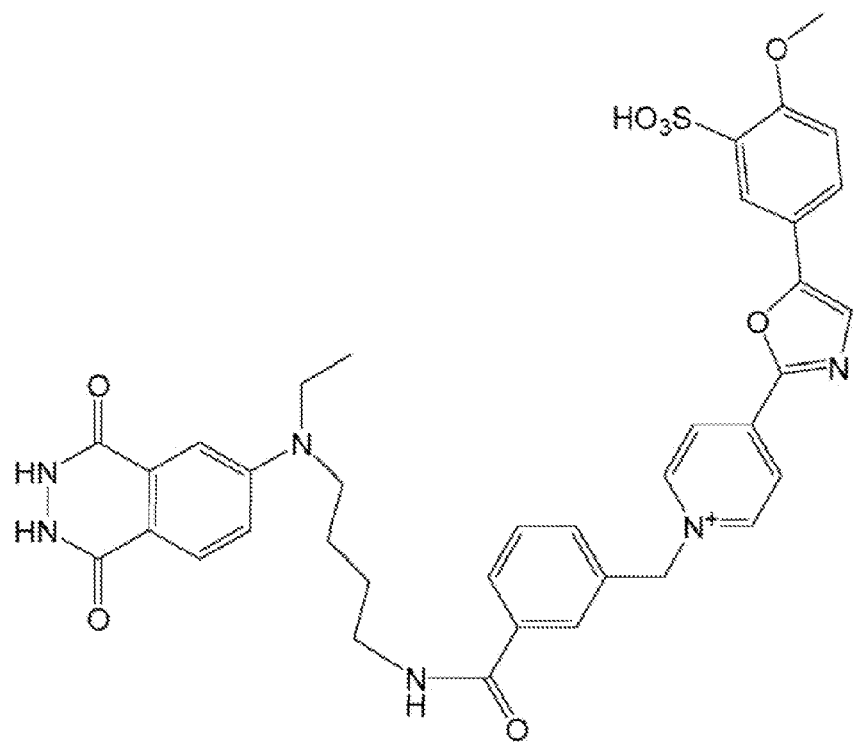
FIG. 8 illustrates chemical structure of IL-Cascade Yellow. (ILCY)
Figure 9:
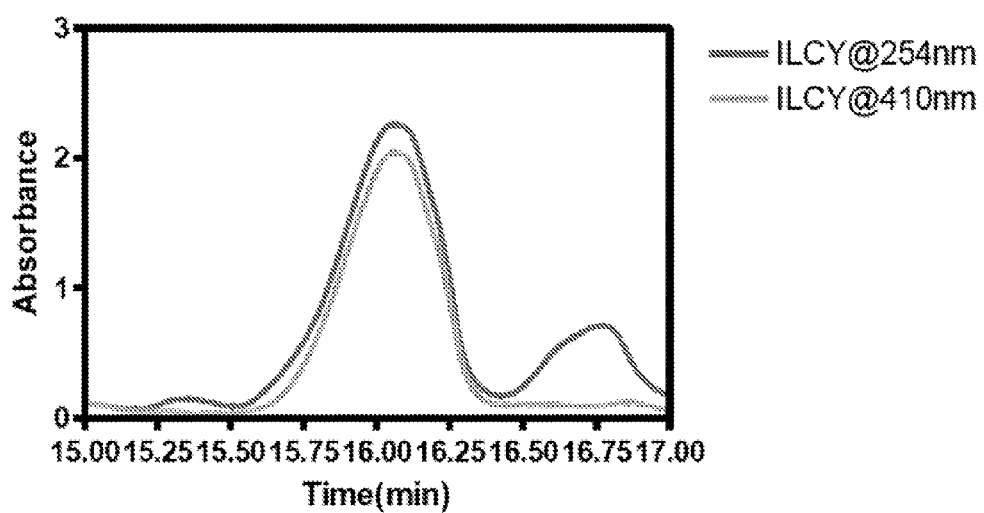
FIG. 9 illustrates HPLC data for IL-Cascade Yellow (ILCY).

6-(N-(4-aminobutyl)-N-ethylamino)-2,3-dihydrophthalazine-1,4-dione (IL) dissolved in dimethylsulfoxide (0.5 ml) was treated with the succinimidylester of Cascade Yellow (1.1 equivalents) in the presence of trimethylamine (100 equivalents) at room temperature. Contents were stirred in an amber colored vial overnight. The product was purified on a Waters HPLC equipped with a dual wavelength detector, using an RP-C18 (Vydac) column, employing a mobile phase gradient of 10-90% acetonitrile with 0.1% TFA in water over 30 minutes. The fraction eluting at $R_f$=16 min was collected, lyophilized to obtain an orange-red solid and identified via ESMS; Calcd for $C_{37}H_{37}N_6O_8S$, 725.2; Found; 724.8. (FIG. 8, FIG. 9).

Example 3

This Example illustrate the synthesis of Luminogenic-Optical Probe ILAF680.

Figure 10:
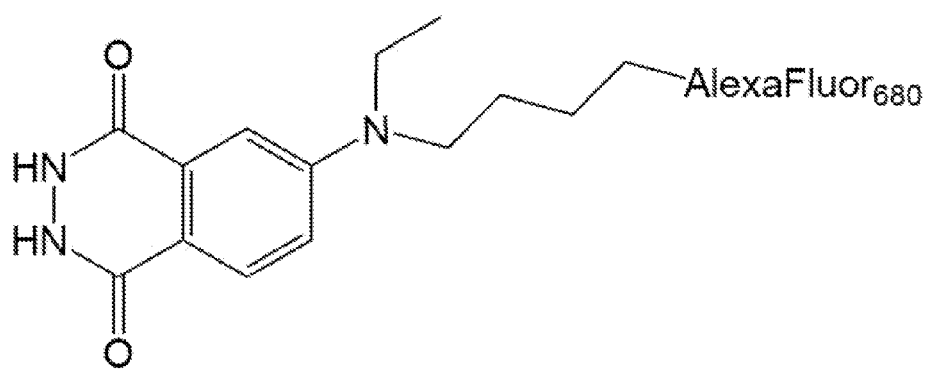
FIG. 10 illustrates chemical structure of IL-AlexaFluor680 (ILAF680).
Figure 11:
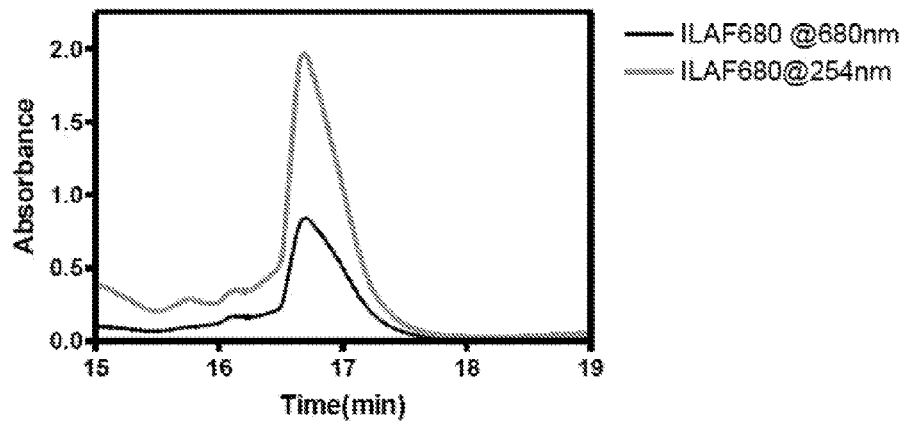
FIG. 11 illustrates HPLC data for IL-AlexaFluor680 (ILAF680).

6-(N-(4-aminobutyl)-N-ethylamino)-2,3-dihydrophthalazine-1,4-dione (IL) dissolved in dimethylsulfoxide (0.5 ml) was treated with succinimidylester of AlexaFluor 680 (1.1 equivalents) in the presence of trimethylamine (100 equivalents) at room temperature. Contents were stirred in an amber colored vial overnight. The product was purified on a Water's HPLC equipped with a dual wavelength detector, using an RP-C18 (Vydac) column, employing a mobile phase gradient of 10-70% acetonitrile with 0.1% TFA in water over 30 minutes. The fraction eluting at $R_f$=16.7 min was collected, lyophilized to obtain dark blue-purple solid and identified via ESMS; Calcd for $C_{35}H_{28}F_2N_4O_8$, 670.2; Found; 670.9. (FIG. 10, FIG. 11)

Example 4

This Example illustrate the synthesis of Luminogenic-Optical Probe ILCY5.

Figure 12:
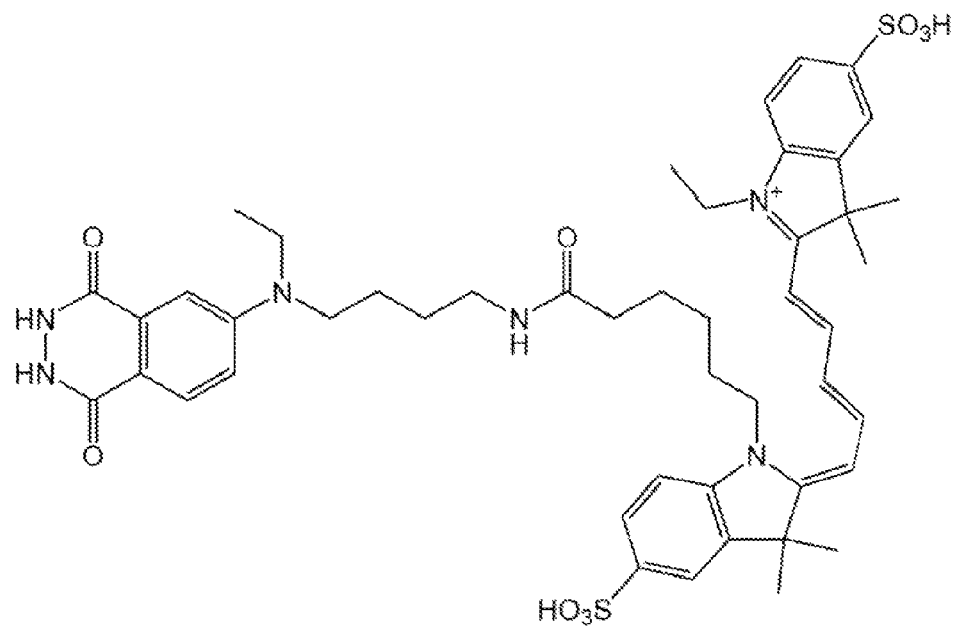
FIG. 12 illustrates chemical structure of Isoluminol-Cy5 (ILCY5).
Figure 13:
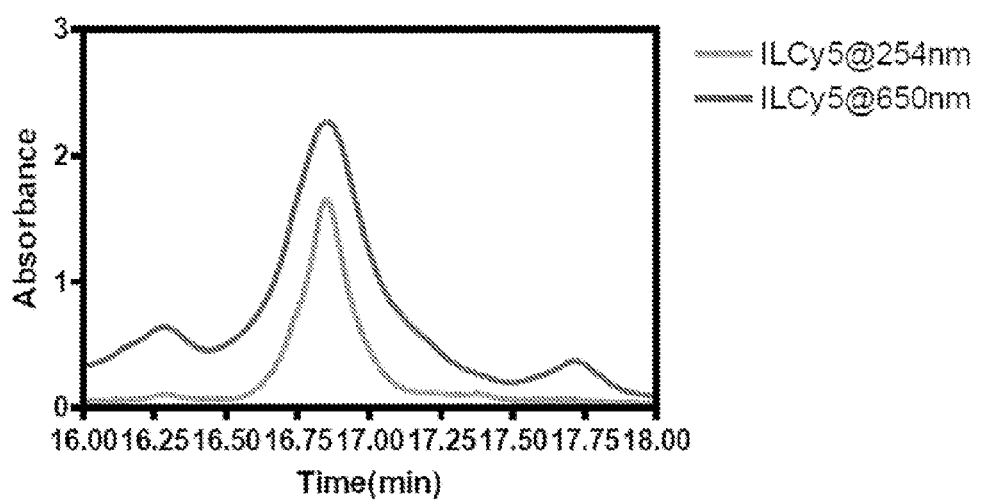
FIG. 13 illustrates HPLC data for Isoluminol-Cy5 (ILCY5).

6-(N-(4-aminobutyl)-N-ethylamino)-2,3-dihydrophthalazine-1,4-dione (IL) dissolved in dimethylsulfoxide (0.5 ml) was treated with the succinimidylester of Cy5 (1.1 equivalents) in the presence of trimethylamine (100 equivalents) at room temperature. Contents were stirred in an amber colored vial overnight. The product was purified on a Water's HPLC equipped with a dual wavelength detector, using an RP-C18 (Vydac) column, employing a mobile phase gradient of 10-90% acetonitrile with 0.1% TFA in water over 30 minutes. The fraction eluting at $R_f$=16.8 min was collected, lyophilized to obtain a blue colored solid and identified via ESMS. Calcd for $C_{47}H_{59}N_6O_9S_2$, 915.4; Found; 915. (FIG. 12, FIG. 13)

This Example illustrate the synthesis of Luminogenic-Optical Probe Luminol-Glycine-Texas Red Conjugate (LGTR) and intermediates thereof.

Synthesis of 2-Chloro-N-(1,4-dioxo-1,2,3,4-tetrahydrophthalazine-5-yl)acetamide

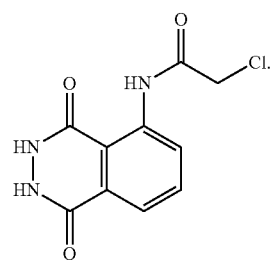 [SMILES: O=C(CCl)Nc1cccc2c(=O)[nH][nH]c(=O)c12]

Luminol (1.55 g; 8.75 mmol) was reacted with 2-chloroacetylchloride (1.24 g; 10.99 mmol), in the presence of pyridine (1.07 g, 13.6 mmol) in acetic:acid (45 ml). Contents were stirred and refluxed for 1 h, allowed to cool to RT, and transferred to a refrigerator for precipitation of the product to obtain 2-Chloro-N-(1,4-dioxo-1,2,3,4-tetrahydrophthalazine-5-yl)acetamide. Thereafter, acetic acid (20 ml) was added to the cold precipitates prior to filtration (for uniform transfer into the filtration unit). Finally, precipitates were filtered, washed with methylene chloride (three times) and dried under vacuum to yield 2-Chloro-N-(1,4-dioxo-1,2,3,4-tetrahydrophthalazine-5-yl)acetamide (1.6 g; 6324 mmol; 72.2%). $^1$H NMR (300 MHz, DMSO-$d_6$) δ: 8.82-8.87 (t, 1H), 7.71-7.89 (dd, 1H), 7.61-7.69 (dd, 1H), 4.34 (s, 2H), 2.16 (s, 3H, Methyl for Acetic Acid); ESMS: Calcd for $C_{10}H_8ClN_3O_3$: 253.0, Found, 253.8.

Synthesis of 2-Amino-N-(1,4-dioxo-1,2,3,4-tetrahydrophthalazine-5-yl)acetamide

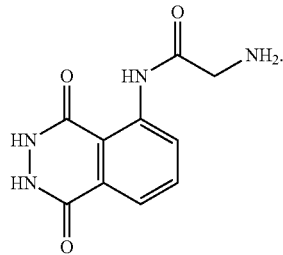

2-Chloro-N-(1,4-dioxo-1,2,3,4-tetrahydrophthalazine-5-yl)acetamide (300 mg; 1.182 mmol) was suspended in ammonium hydroxide (7 ml) and stirred slowly in a vial at 4 C for 8 days (30%). The reaction mixture was transferred into a flask and hot water (25 ml) was added to the reaction mixture, filtered, and the filtrate was collected. The initial pH (12) of the filtrate was adjusted to 5.38 by slow addition of acetic acid to obtain the intermediate. The beige colored solid was filtered, rinse with water (10 ml), washed with methanol (50 mL), and finally with ether (50 ml), and then dried under reduced pressure. The residue was suspended in hydrazine (30% in water, 22 ml) and heated to dissolve the precipitates. The contents were allowed to cool to RT, pH was adjusted to 4.8, and precipitates were obtained upon cooling. The resultant precipitates were filtered, washed with water, methanol (cold), ether, and then dried under reduced pressure to obtain 2. $^1$H NMR (300 MHz, DMSO-$d_6$) δ: 8.86 (d, 1H), 7.85 (t, 1H), 7.60 (d, 1H), 3.33 (s, 2H), 2.16 (s, 3H, Methyl for Acetic Acid); ESMS: Calcd for $C_{10}H_{10}N_4O_3$: 234.0, Found, 235.0; HPLC: Purity was further analyzed on a C-18 column (Vydac) employing a mobile phase eluent gradient of 10-90% acetonitrile in water containing 0.1% TFA over 30 minutes with a flow rate of 1 mL/min, Rt=13.2 min.

Figure 14:
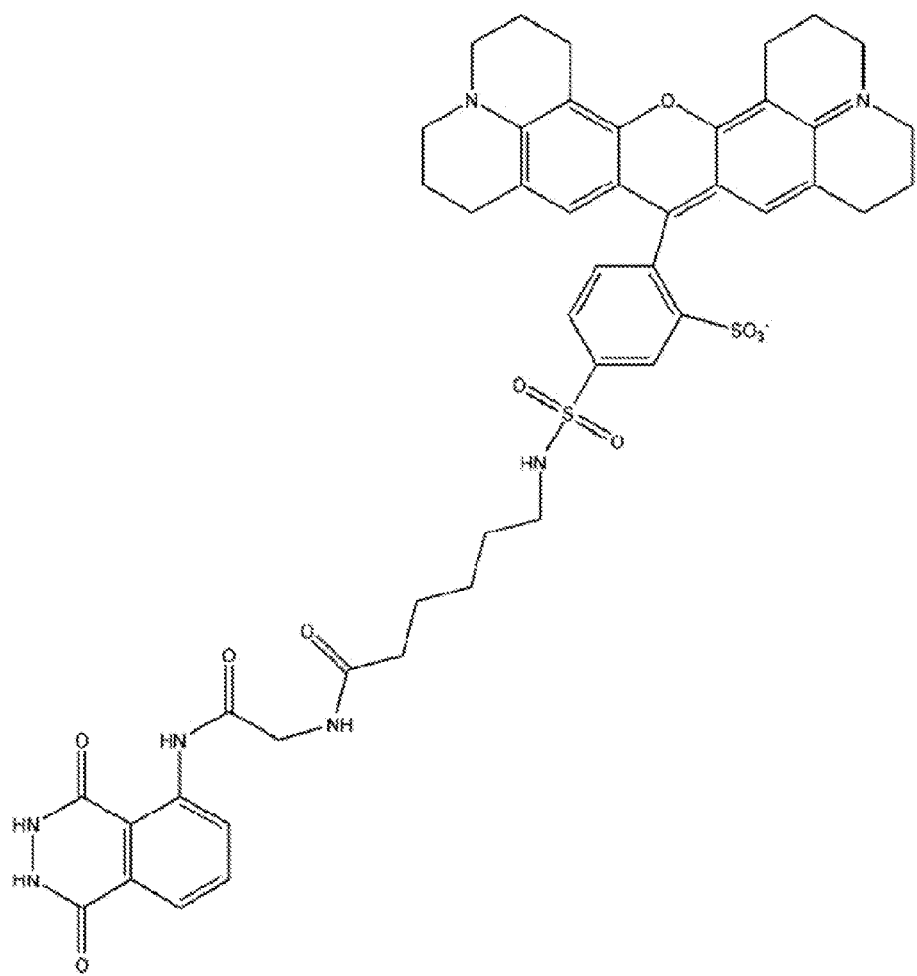
FIG. 14 illustrates chemical structure of Luminol-Glycine-Texas Red Conjugate (LGTR).

Synthesis of Luminol-Glycine-Texas Red conjugate (LGTR, FIG. 14)

2-Chloro-N-(1,4-dioxo-1,2,3,4-tetrahydrophthalazine-5-yl)acetamide (1 mg; 4.2 M) was dissolved in dry dimethylsulfoxide (DMSO; 1.5 ml) in an amber colored vial and treated with Texas Red succinimidylester (1 mg; 1.22 M) dissolved in dry DMSO and diisopropylethylamine (DIEA). Contents were stirred at room temperature overnight and analyzed on an HPLC using a C-18 column (Vydac), employing a mobile phase eluent mixture gradient of 10-90% acetonitrile in water containing 0.1% TFA over 30 minutes with a flow rate of 1 ml/min. The fraction eluting at Rt=21.6 min was collected, lyophilized to obtain 3, a dark purple colored solid (0.77 mg; 0.748 M; 61.3%, based upon TR-succinimidyl ester) and identified via ESMS; Calcd for $C_{47}H_{49}N_7O_{10}S_2$, 935.0; Found; 936.0.

Figure 15:
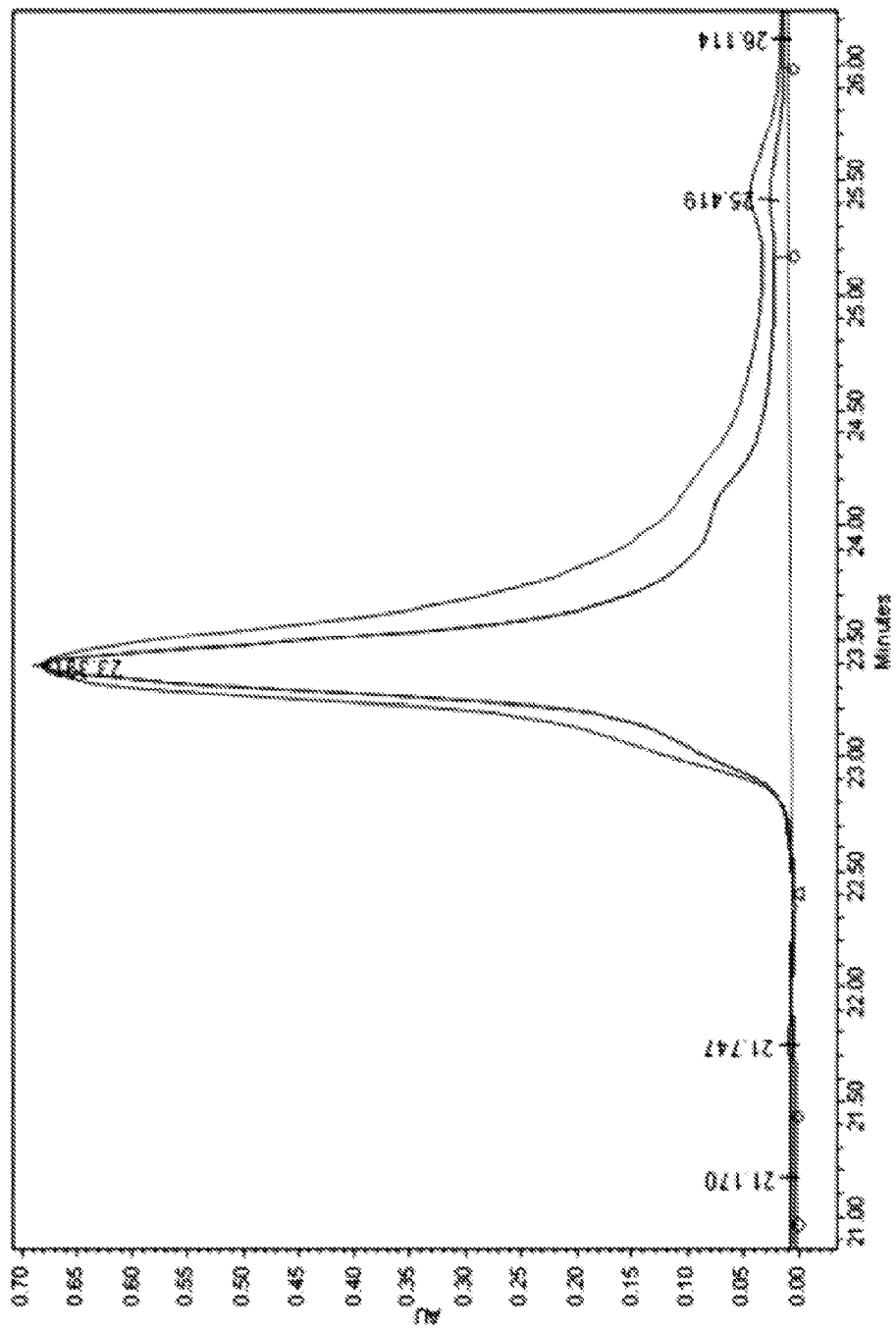
FIG. 15 illustrates HPLC data for Luminol-Glycine-Texas Red Conjugate (LGTR).

HPLC data for LGTR using an eluent gradient of 10-90% acetonitrile in water containing 0.1% TFA over 30 minutes with a flow rate of 1 ml/min on a Waters HPLC equipped with a dual wavelength detector set to 254 nm and 595 nm: the blue color represents compound at 254 nm and the red color shows compound at 595 nm (FIG. 15).

Example 5

This example illustrates that luminol-BL is dependent on MPO in vitro.

Luminol-oxidation can be visualized by bioluminescence imaging and is dependent on MPO activity in vitro. Luminol-dependent BL of stimulated phagocytes and whole blood has been extensively studied using photo-multiplier tube (PMT)-based luminometers. To determine whether BLI could be similarly used to detect oxidant production in biological material, we used a charge-coupled device (CCD)-based bioluminescence imaging system to monitor phagocyte activation in heparinized whole blood (1 μL). Fresh heparinized whole blood (1 μL) was incubated with luminol (100 μM) in MEBSS (200 μL). At t=0, the potent protein kinase C (PKC) activator PMA (5 μM) or vehicle control (DMSO) was added to a final concentration of 5 μM and BL was monitored for 90 min. Images show sequential color-coded maps of photon flux superimposed on black & white photographs of the assay plates (FIG. 1b). PMA induced a time-dependent increase in BL, peaking ~20-25 min post stimulation at ~30-40-fold over background values (FIGS. 1b and 1d (asterisk). No significant change in BL was observed in unstimulated cells (FIG. 1b). The timing and magnitude of this response were in excellent agreement with previously-documented reports of phagocytic activation performed using PMT-based luminometers, but lacking spatial resolution (DeChatelet, L. R. et al., J Immunol 129, 1589-1593, 1982); Lundqvist, H. et al., Free Radic Biol Med 20, 785-792 1996). Furthermore, while others reported using $5 \times 10^5$ to $1 \times 10^7$ purified phagocytes to achieve a detectible signal using PMT-based readouts, we found that only a few thousand phagocytes present in 1 μL of whole blood were sufficient to produce signal-to-background ratios>30. Thus, CCD-based, luminol-enhanced BLI offers both spatial resolution and 100- to 1000-fold increased sensitivity over PMT-based photon counting.

Example 6

This example illustrates that luminol-BL is dependent on MPO in vitro.

Prior studies with isolated neutrophils suggested that luminol-BL during a phagocytic oxidative burst is dependent on MPO activity (DeChatelet, L. R., et al., J Immunol 129, 1589-1593, 1982; Bender, J. G., et al., Infect Immun 41, 1062-1070, 1983; Lundqvist, H., et al., Free Radic Biol Med 20, 785-792, 1996). However, in vitro studies demonstrate that other oxidants can cause luminol-BL. For example, a recent study examining the applicability of luminol as an in vivo probe for molecular imaging of ROS production attributed luminol-BL in vivo to a direct interaction with $H_2O_2$ (Chen, W. T., et al., Mol Imaging 3, 159-162, 2004). Hypothetically, uncharged and relatively unreactive $H_2O_2$ could readily diffuse across biological membranes, generating highly reactive OH. upon catalysis by free or possibly heme-bound metals, e.g., hemoglobin and cytochromes. In such a case, OH. may react directly with luminol to produce light independent of MPO activity. Therefore, we performed a series of experiments to establish the mechanism of luminol-BL and the requirement for MPO on luminol-BL in vitro (with purified MPO), ex vivo (in whole blood) and in vivo (with animal imaging).

As a first step, we analyzed the impact of pharmacological inhibition of MPO on luminol-BL in vitro. Light production was measured in an assay system comprised of purified human MPO (5 mU), $H_2O_2$ (50 μM), luminol (10 μM) and increasing concentrations of a relatively selective MPO inhibitor (4-ABAH, 0-500 μM, FIG. 1c, Kettle, A. J., et al., Biochem J 308 (Pt 2), 559-563, 1995; Kettle, A. J., et al., Biochem J 321 (Pt 2), 503-508, 1997). BL output was inversely proportional to 4-ABAH concentration (apparent $IC_{50}=1\pm0.7$ μM), indicating that it was dependent on MPO activity.

Example 7

This example illustrates that luminol-BL is dependent on MPO ex vivo.

4-ABAH also inhibits MPO activity in cultured cells (Kettle, A. J., et al., Biochem J 308 (Pt 2), 559-563, 1995), and we therefore used this compound to analyze MPO-dependent luminol-BL in PMA-stimulated whole blood. It is important to note that metals such as iron are highly abundant in blood, but are confined to specific cellular compartments, i.e., hemoglobin in erythrocytes or cytochromes in mitochondrial membranes. Fresh heparinized whole blood (1 μL) was incubated with increasing concentrations of 4-ABAH (0-6.6 mM) and luminol (100 μM) in MEBSS (200 μL). At t=0, PMA was added to a final concentration of 5 μM and BL was monitored for 60 min at 7.5 min intervals. Luminol-BL (fold-initial) was plotted as functions of time (d) and concentration of 4-ABAH (c) as derived from the 22.5 min time point. The apparent $IC_{50}$ of 4-ABAH ex vivo was determined to be $50\pm15$ μM. Surprisingly, although $H_2O_2$ generated in response to PMA stimulation could theoretically diffuse and react with hemoglobin, cytochromes or free iron, production of BL by luminol (FIG. 1d, e) was almost completely inhibited by 4-ABAH (apparent $IC_{50}$ $50\pm15$ μM; FIG. 1e). These observations indicate that even in the presence of other physiologic redox catalysts, luminol-BL requires MPO.

Example 8

This example illustrates that luminol-BL is dependent on MPO ex vivo.

To validate the role of MPO, whole blood from wild-type MPO+/+ or MPO−/− mice was similarly analyzed for luminol-BL upon stimulation with PMA (FIG. 10. Fresh heparinized whole blood from $MPO^{+/+}$ or $MPO^{-/-}$ mice was incubated with luminol (100 μM) in MEBSS (200 μL). BLI (0-55 min) was initiated instantly upon stimulation with PMA (5 μM). Luminol-BL was plotted as a function of time post PMA. As previously demonstrated with neutrophils isolated from MPO-deficient patients (Gerber, C. E., et al., Eur. J. Clin. Chem. Clin. Biochem. 34, 901-908, 1996), luminol-BL was undetectable with whole blood of MPO−/− mice. Collectively, these data indicated that in whole blood ex vivo, luminol-BL depended both on enzymatically active MPO and phagocyte activation. Moreover, we now demonstrate that the concurrent presence of intact erythrocytes, a rich source of heme iron, did not affect MPO-specific luminol-BL activity.

Example 9

This example illustrates that ex vivo, luminol-BL-responsive MPO is generated by the Phox complex.

To determine the relative contribution of other ROS to the BL signal induced by luminol in stimulated blood ex vivo, we focused on two enzymatically-catalyzed ROS products, O2.- and NO., generated by the Phox complex and nitric oxide synthase (NOS), respectively, as well as their reaction product, peroxynitrite ($ONOO^-$). Freshly-drawn blood (1 μL) from an $MPO^{+/+}$ mouse was incubated with the NOS inhibitor L-NMMA (1 mM) or the Phox inhibitor DPI (10 μM), respectively, and imaged 20 min after stimulation with PMA (5 μM). As expected, pretreatment of whole blood ex vivo with the potent Phox inhibitor DPI (10 iM) culminated in complete abrogation of PMA-induced BL (FIG. 1g). This is not surprising since Phox is directly upstream of MPO (FIG. 1a). On the other hand, and in agreement to a previous report (Bednar, M. et al., J Leukoc Biol 60, 619-624, 1996), inhibition of NOS by L-NMMA (1 mM) did not cause a significant reduction in luminol-dependent BL (FIG. 1g). These data indicate that $ONOO^-$-dependent BL, a result of NO. oxidation by O2.-, did not contribute significantly to luminol-BL ex vivo.

Example 10

This example illustrates immobilized GOX can be used to generate MPO in vivo.

We next determined the biochemical requirements and pharmacokinetics of luminol-BL in an intact animal and whether MPO activity could be imaged in vivo. Glucose oxidase (GOX) catalyzes the oxidation of β-D-glucose with the concomitant production of peroxide, releasing 1 mole of $H_2O_2$ for each mole of glucose consumed. Thus, one can use immobilized GOX in vivo as an $H_2O_2$ generator (Chen, J. W., et al., Radiology 240, 473-481, 2006). We embedded GOX (30 U), MPO (20 U); MPO+GOX (same concentrations) or vehicle (PBS) in Matrigel solution and established subcutaneous implants of these mixtures on the backs of NCR nu/nu mice (n=3, FIG. 2a). Shown is a BL image taken at t=0 (before luminol administration).

Upon systemic luminol administration (200 mg/kg BW, i.p.), intense BL was emitted only from the MPO+GOX implant (FIG. 2b). FIG. 2b shows that BLI (5-60 min at 5 min intervals) was initiated after i.p. bolus injection of luminol (200 mg/kg BW). Photon fluxes were determined from ROI's, manually drawn over the different implants and plotted as a function of time. Vehicle (○), GOX (□), MPO(▲) or MPO+GOX (●). Shown are representative time-course plots from one mouse. BL reached maximum values 10 min after injection of luminol and then decayed to baseline between 65 and 90 min in a biphasic manner (FIG. 2c). BL levels from all other implants were essentially equal to background values. Taken together, these data indicate that, (a) BLI of MPO activity is achievable using luminol as a molecular probe, (b) MPO is indeed indispensable for generation of BL by luminol in vivo, and (c) luminol is rapidly absorbed upon i.p. injection, becoming readily available systemically for MPO-catalyzed oxidation.

Example 11

This example illustrates imaging MPO activity in inflammatory foci in vivo.

Having shown that luminol could be used as a selective probe for MPO activity in whole blood ex vivo and in MPO/GOX implants in vivo, we next sought to analyze whether luminol could noninvasively and quantitatively monitor physiological levels of MPO activity in two animal models of acute inflammation.

Topical application of PMA onto the earlobes of mice induces acute dermatitis, manifested by local swelling, erythema and infiltration of neutrophils. Here, the inflammatory process is traditionally monitored by caliper measurements of ear thickness, histological examination and destructive assessment of inflammatory proteins (e.g., metalloproteinases, MPO and neurophil elastase) (Fretland, D. J. et al. Inflammation 19, 333-346, 1995). We therefore used this model for assessment of MPO activity by luminol-BLI in both MPO$^{+/+}$ and MPO$^{-/-}$ mice. Acute dermatitis was generated by topical application of PMA on the left ear lobe of MPO$^{+/+}$ or MPO$^{-/-}$ mice (shown are three representative mice for each genetic background, n=5 for each). Twenty-four hours after topical application of PMA, mice were imaged (FIG. 3a) following the administration of luminol (200 mg/kg BW, i.p.). BL was locally emitted from PMA-treated earlobes (left ears) of MPO$^{+/+}$ mice, reaching background-normalized levels of 13.1±0.2 (s.e.m.) fold over vehicle-treated ears (right ears). Serial. BLI post-luminol injection showed a gradual decay to background levels within 4 days post PMA application (data not shown). BL from PMA-treated ears of MPO$^{-/-}$ mice was 1.9±0.5 (s.e.m.) fold over vehicle-treated ears, i.e., essentially background (FIG. 3a).

Example 12

This example illustrates that luminol-BL was dependent on MPO in an acute focal arthritis model.

We next imaged MPO activity in a focal arthritis model. Acute arthritis can be chemically generated by intra-articular injection of LPS (Chen, W. T., et al., Mol Imaging 3, 159-162, 2004). This model is well-suited for imaging studies since it allows for generation of unilateral arthritis, thus allowing each animal to serve as its own control. LPS was injected to the joints of the left lower limbs of wild type MPO$^{+/+}$ (FIG. 3b, left panel, n=5) or MPO$^{-/-}$ mice (FIG. 3b, right panel, n=5). Vehicle (PBS) was injected into the joints of the right lower limbs. At t=0 (before LPS injection), 24, 48, 72, 96 and 120 h, luminol was administered (200 mg/kg BW, i.p.) and mice were imaged. Representative images taken at t=48 h are shown in (FIG. 3b). BL emission was readily detected from the LPS-treated joints of MPO$^{+/+}$ mice, as shown in FIG. 3b. BL emission peaked 48 h after administration of LPS at ~25 to 30-fold over background-normalized LPS-induced luminol BL (±s.e.m., quantified as fold over vehicle-treated foot for each MPO genotype at the indicated time point, FIG. 3c). Serial BLI showed a gradual decay in emissions, but signal was still evident 5 days post treatment (~10 to 15-fold over background; data not shown). No BL was observed in vehicle-treated joints at all times. In good agreement with the dermatitis model, negligible luminol-BL could be detected from either LPS- or vehicle-treated joints of MPO$^{-/-}$ mice (FIG. 3b, c) at all times.

Example 13

This example illustrates that

MPO affects vascular tone and permeability at sites of inflammation through oxidation of NO. in a rodent model of LPS-induced acute endotoxemia (Eiserich, J. P. et al., Science 296, 2391-2394, 2002). MPO also inhibits migration and recruitment of neutrophils in a UVB-induced sunburn model (Komatsu, J., et al., Inflamm. Res. 55, 200-206, 2006). The latter has been attributed to ROS-induced autocrine modification of secreted cytokines (i.e., KC and MIP2). To exclude the possibility that the lack of detectable signal in the LPS-treated joints of MPO$^{-/-}$ mice was attributable to a decrease in migration, recruitment or extravasation of neutrophils, histological analysis of tissue specimens (FIG. 3d) was undertaken 48 h post treatment, the point at which we observed maximal luminol-BL. In response to LPS, similar numbers of neutrophils were recruited to the intra-articular space of MPO$^{+/+}$ and MPO$^{-/-}$ mice (FIG. 3d, lower panels, magnification: ×100, insets; ×630; and FIG. 3e). In both genotypes, vehicle treatment failed to induce neutrophil infiltration (FIG. 3d, upper panels). In FIG. 3e, for both genetic backgrounds, neutrophils were counted in 5 fields (magnification ×400). Results are expressed as the average number of neutrophils per high power field (HPF±s.e.m.).

Taken together, these data indicate that BLI with luminol provides methods for monitoring phagocytic activation at sites of inflammation in vivo, even in the presence of other potential redox catalysts. In addition, these data indicate that BLI with luminol provides methods for monitoring MPO activity at sites of inflammation in vivo, even in the presence of other potential redox catalyst.

Example 14

This example illustrates that EPO in activated eosinophils does not contribute to luminol-BLI in vivo.

Eosinophil peroxidase (EPO) is known to produce bioluminescence in vitro when luminol is utilized as a substrate (Haqqani, A., et al., Anal. Biochem. 273, 126-132, 1999). Thus far, our models in vivo characterized leukocyte activation by PMA (FIG. 3a) or neutrophil recruitment and activation by LPS (FIG. 3b-e). However, in principle, neither of these models necessarily recruited a significant population of locally activated eosinophils. Therefore, to determine the contribution of EPO to the luminol BLI signal in vivo, we characterized a model of allergic contact hypersensitivity.

Eosinophil-dominant recruitment and activation was induced by passive immunization against DNP followed by topical challenge with DNFB (Ray, M., et al., J. Immunol. 131, 1096-1102, 1983) in both MPO+/+ control as well as MPO$^{-/-}$ mice. Because the only peroxidase present at the site of allergic inflammation in MPO$^{-/-}$ mice would be EPO, comparing the two MPO genetic backgrounds should reveal the fraction of the BL signal originating from EPO in vivo. Acute allergic dermatitis was induced by passive immunization with anti-DNP IgE and topical challenge with DNFB on the left ear lobes of MPO$^{+/+}$ (n=14) and MPO$^{-/-}$ (n=10) mice. Right ears served as vehicle controls and mice challenged with DNFB, but not anti-DNP IgE, served as negative controls. Twenty-four hours after application of DNFB, luminol was administered (200 mg/kg BW, i.p.) and mice were imaged. Importantly, induction of acute contact hypersensitivity in MPO$^{-/-}$ mice resulted in no significant luminol-BL signal from the inflamed ears, while in MPO$^{+/+}$ mice, substantial luminol-BL was observed (FIG. 4a, b). In control mice that were not immunized with anti-DNP IgE, and in vehicle-treated ears of both MPO genetic backgrounds, no significant luminol-BLI signal was observed (FIG. 4a, b). In FIG. 4a, one MPO$^{+/+}$ and one MPO$^{-/-}$ representative mouse are shown. In FIG. 4b, background (vehicle on right ear)-normalized DNFB-induced luminol-BL (±s.e.m.) is shown for each MPO genotype.

Example 15

This example illustrates that eosinophils are present in BL-positive tissues.

To confirm that indeed eosinophils had infiltrated the inflamed ears, histological analysis of tissue specimens was undertaken 24 h post DNFB treatment (FIG. 4c). Histological analysis of proximal ear lobes revealed massive edema and eosinophilia within a mixed cell infiltrate 24 h after DNFB treatment of both MPO$^{+/+}$ and MPO$^{-/-}$ mice, but not vehicle-treated mice (magnification: ×200); lower right panel shows eosinophils in a treated MPO$^{-/-}$ mouse (magnification: ×630). Insets: Immunostaining with anti-dibromotyrosine mAb of the same specimens documenting the presence of bromotyrosine adducts in treated ears of both MPO$^{+/+}$ and MPO$^{-/-}$ mice (brown staining), but not vehicle-treated controls (magnification: 100×). A prominent eosinophilia within a mixed cell infiltrate was observed. Similar numbers of eosinophils were recruited to the inflamed ears of both MPO$^{+/+}$ and MPO$^{-/-}$ mice, while in both genotypes, vehicle treatment failed to induce eosinophilic infiltration (FIG. 4c, d). For both genetic backgrounds, eosinophils were counted in 5 fields (magnification ×400). Results are expressed as the average number of eosinophils per HPF±s.e.m (FIG. 4d). Furthermore, immunohistochemical analysis with an antidibromotyrosine mAb directly identified the presence of bromotyrosine adducts in the inflamed ears of both MPO$^{+/+}$ and MPO$^{-/-}$ mice, but not vehicle-treated ears (FIG. 4c, insets). These data directly confirmed the presence of active EPO in MPO$^{-/-}$ mice, despite the absence of luminol-BLI signals. Thus, we conclude that the contribution of EPO to luminol-BLI in vivo is negligible.

Example 16

This example illustrates that luminol-BLI detects MPO activity in spontaneously-generated tumors of GzB→Tax mice.

In GzB→Tax mice, the HTLV-1-associated oncogene Tax is expressed under control of the granzyme B promoter in activated T- and NK-cells. We have previously shown that GzB→Tax mice spontaneously develop large granular lymphocytic (LGL) tumors at 200-300 days of age (Grossman, et al., Proc. Nat'l. Acad. Sci. USA 92, 1057-1061, 1995), and that these tumors are massively infiltrated with neutrophils (Gao, L. et al., Blood 106, 4294-4302, 2005) (FIG. 5a). FIG. 5a shows H&E staining of a large (~1 cm) tumor from the tail of a GzB→Tax mouse revealed that the majority of the cell mass was comprised of neutrophils (polymorphic nuclei; magnification ×630).

To investigate noninvasively whether these tumor-residing neutrophils might be constitutively stimulated, thus activating MPO and its oxidizing substrate $H_2O_2$, tumor specimens were first analyzed for the presence of MPO by immunohistochemical staining. FIG. 5b shows MPO immunostaining of the same specimen as in FIG. 5a, showing co-localization of MPO within neutrophils (brown staining). Negative immunostaining was observed in the absence of primary or secondary antibodies (data not shown). Immunoreactive MPO colocalized with neutrophils, while tumor LGL cells (T- and NK-cells, rounded nuclei) were unreactive with the MPO antibody.

We next used BLI to examine tumor-bearing GzB→Tax mice after intraperitoneal administration of luminol (200 mg/kg BW, i.p., FIG. 5 c-g). FIG. 5c shows H&E staining of a very small (~200 μm) tumor from the earlobe of a GzB→Tax mouse (arrow). FIG. 5 d-g show luminol-BLI of tumor-bearing GzB→Tax mice showing co-localization of luminol-BL with tumor foci (yellow arrows). Note that luminol-BLI detected sub-millimeter tumors (as shown in c, g) before these tumors could be visualized or palpated. In all cases, luminol-BL colocalized with foci of tumorigenesis, although some heterogeneity was observed (e.g., note the lack of luminol-BL emitted from the second tail tumor in FIG. 5d or BL emitted from only a part of the ear tumor in FIG. 5e). This variability was expected because these spontaneously-generated tumors are heterogeneous histologically and exhibit areas with low infiltration of neutrophils and "hot spots" with neutrophil content≥90% (data not shown).

Surprisingly, imaging revealed confined foci of BL at regions where no evident tumors could be visualized or palpated (e.g., the two foci in FIG. 5g). Strikingly, serial sectioning followed by histological examination of such regions revealed pre-vascularized, early tumor foci (~200 μm diameter) comprising only a few hundred cells (FIG. 5c). These foci displayed neutrophil infiltration located at the center of the tumor, and not a mixed population with LGL cells as seen with larger tumors (FIG. 5a, b), indicating an unexpected role for MPO in early tumorigenesis.

Taken together, luminol-enhanced BLI provides highly sensitive monitoring of MPO activity within neutrophil-infiltrated tumors, allowing detection of tumorigenic foci significantly sooner than by conventional visual inspection or palpation. The observation that tumor-residing neutrophils exhibited high MPO-dependent oxidative activity offers opportunities to study the role of MPO and neutrophil activation in the initiation, progression and dissemination of tumors. Moreover, we observed luminol-BL for many days in our animal tumor model, indicating that oxidant production occurred continuously in vivo.

Importantly, EPO did not contribute to luminol-BLI in vivo. These data do not contradict decades of careful in vitro EPO biochemistry, but rather, the demonstrated mechanisms of luminol oxidation by neutrophils and eosinophils in vitro are consistent with our observations in vivo. In particular, stimulated neutrophils canonically discharge granular contents into the phagosome wherein $H_2O_2$ and $Cl^-$ react in the presence of MPO to produce concentrated HOCl (Klebanoff, S. J., J. Leukoc. Biol. 77, 598-625, 2005; Nathan, C., Nat Rev Immunol 6, 173-82, 2006). By contrast, upon eosinophil activation, EPO is secreted into extracellular spaces (Giembycz, M. A., et al., Pharmacol. Rev. 51, 213-340, 1999). Critically, in purified cells in vitro, luminol-BL has been observed within the intracellular compartment of neutrophils versus the surrounding extracellular compartment of eosinophils (Freiburghaus, et al., J Biolumin. Chemilumin. 6, 115-121, 1991). However, tissues dynamics are more complex in vivo. As systemic luminol is delivered to sites of inflammation and diffuses into phagocytic compartments of activated neutrophils, a stable highly concentrated reservoir of MPO-generated HOCl and other oxidative species will persist throughout the oxidative burst for reaction with luminol. By contrast, once EPO has been secreted in vivo, the enzyme, reactants and products will be diluted by diffusion and bulk flow or consumed by endogenous catalase, thereby reducing local concentrations of oxidizing species necessary for BL in the presence of luminol. Furthermore, in most extra-vascular tissues, the extracellular milieu will contain not only $Cl^-$, but also thiocyanate ($SCN^-$). $SCN^-$, the preferred substrate for EPO (Slungaard, A., et al., J. Biol. Chem. 266, 4903-4910, 1991), and the product, HOSCN, a much weaker oxidant than HOCl, would presumably oxidize luminol less rapidly, if at all. Without being limited by theory, we propose that the surprising selectivity of luminol-BLI for activated MPO in vivo arises from differences in physiological compartmentation and local concentration of activated MPO versus EPO and their oxidative products. In vivo, only the phagocytic respiratory burst provides simultaneously an enzyme (MPO), a compartment accessible to luminol (phagosome), and sufficiently concentrated oxidative products for productive BLI.

Example 17

This example illustrates compounds for imaging MPO activity in vitro and in vivo.

We have had great interest in "red-shifting" the emission spectra of luminol for applications in vivo. This arises from the optical absorption properties of biological tissues. For wavelengths in the blue-green range, little light will travel through tissues as most tissues suffer from high light attenuation below a wavelength of 600 nm. Absorption of light at 489 nm (maximal excitation of enhanced Green Fluorescence Protein, a commonly used fluorescent protein in bioassays) is approximately 500-fold greater than absorption at 630 nm (red). Secondly, from any photonic excitation source in the green-blue range of the visual spectrum (<500 nm), there tends to be significant amounts of background fluorescence in tissues and cells causing autofluorescence. This significantly reduces signal-to-noise ratios which degrades the sensitivity of the assay in vivo. Thus, a red-shifted luminol analogue is desirable for imaging applications in vivo.

Toward this goal, we have synthesized novel red-shifted luminol and isoluminol analogues and tested their capacity to report MPO activity in vitro and in vivo. Detailed synthesis and chemical characterization of conjugates of isoluminol-Oregon Green, isoluminol-Cascade Yellow, isoluminol-Alexa Fluor 680, and isoluminol-Cy5 are described herein. These methods provide proof-of-principle synthetic strategies for these types of compounds. In addition, many other fluorophores can be conjugated to isoluminol using our general strategy. Fluorophores are well known to those skilled in the art and many are sold commercially by commercial suppliers such as Invitrogen Molecular Probes. Detailed synthesis and chemical characterization of a conjugate of luminol-glycine-Texas Red (LGTR) is also described. LGTR is an example of a red-shifted luminol conjugate that can be used with in vitro and in vivo assays such as those disclosed herein. Furthermore, synthesis of LGTR is representative of any fluorophore, such as red-shifted fluorophores and near-infrared fluorophores, that can be conjugated to luminol using this general procedure. A general structure of isoluminol conjugates that can be used in imaging applications is provided herein. In addition a general structure of luminol conjugates that can be used in MPO imaging applications is also provided.

For optical characterization of compounds, a NanoDrop UV-Vis spectrometer (ND-1000) was utilized for collecting spectra. UV-Vis absorption spectra were collected by diluting 1 mM stocks dissolved in DMSO to 100 M in Milli-Q $H_OW$ (18 M resistance). The spectrometer was blanked using the appropriate vehicle solution containing 10% (v/v) DMSO in water. A Cary Fluorescence Spectrometer was used for collecting fluorescence emission spectra. Samples were diluted from 1 mM stocks dissolved in DMSO to 1 µM in Milli-Q $H_2O$ (18 MΩ). Fluorescence emission spectra were collected and background was subtracted based upon a 0.1% DMSO in water sample. Spectra were normalized to peak fluorescence intensity.

Figure 20:
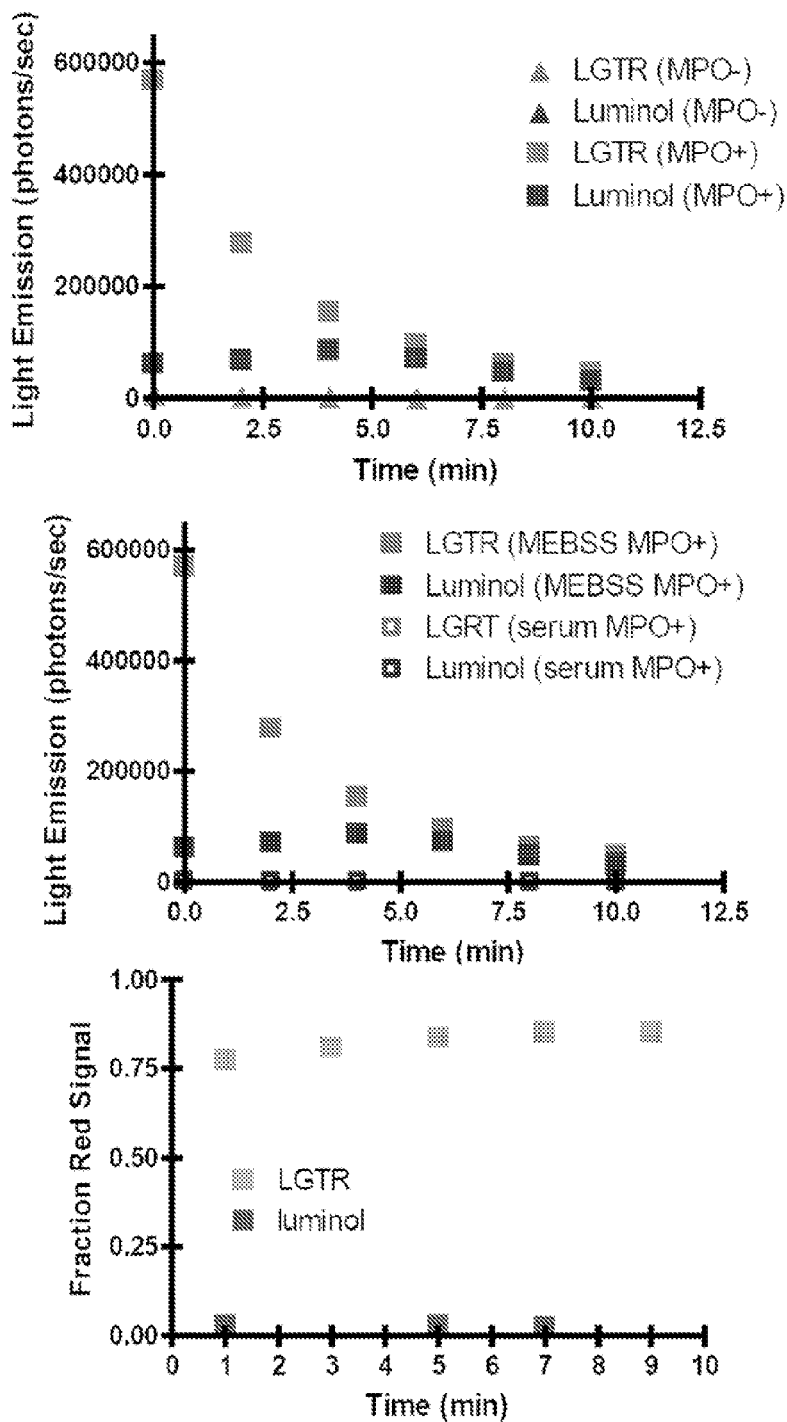
FIG. 20 illustrates an analysis of the output of LGTR and luminol in vitro.

For proof-of-principle studies and analysis in vitro, assays were performed in colorless MEBSS buffer (mM: 4.0 HEPES, 5.4 KCl, 144 NaCl, 0.8 $Na_2HPO_4$, 1.2 $CaCl_2$, 0.8 $MgSO_4$, and 5.6 D-glucose, pH 7.4) in black-coated 96-well plates. To analyze the output of LGTR and luminol in vitro, 10 M of each were mixed with purified MPO (5 mU) and vehicle (MEBSS). $H_2O_2$ was then added to a final concentration of 50 µM, and ten seconds later, the plate was imaged in an IVIS instrument, alternating between the open filter and >590 nm filter (exposure time, 60 sec; binning, 4; FOV, 10 cm). Photon flux (photons/sec) mean values±s.e.m. were plotted as a function of time for 10 min. In purified MPO in MEBSS buffer, our LGTR conjugate was brighter than luminol and the percent of the signal greater than 590 nm (red spectrum) for LGTR was ~75% (FIG. 20). As a control, we synthesized a non-fluorogenic compound (luminol-glycine), which as expected, generated no signal. Of note, analysis in vitro using purified MPO mixed with 100% serum rather than MEBSS showed no light output for both LGTR and luminol.

Example 18

This example illustrates spectrally unmixing chemiluminescence emitted from a substrate of horseradish peroxidase (HRP) from the chemiluminescence output of a substrate of alkaline phosphatase (AP) in in vitro assays. This approach can apply to analysis of a variety of plate assays, protein-on-chip formats, lysates and biochemical techniques such as simultaneous multiplex imaging of two proteins labeled with HRP and AP, for example, by Western blot or ELISA assays. Herein, to demonstrate the proof-of-principle, in black-walled 96-well plates, a 100:1 dilution of a solution containing HRP (2000 U/mL) at various concentrations was aliquoted in triplicate as a gradient across the plate, while another 100:1 dilution of a solution containing AP (2 U/mL) was aliquoted in triplicate in the same wells as an opposing gradient across the plate. Enzyme solutions were mixed and then a developing solution comprising: Tris buffer (100 mM), $H_2O_2$ (0.00003%), beta-methyl cyclodextrane (0.5 mM), disodium 2-chloro-5-[4-methoxyspiro (1,2-dioxetane-3,2'-[5-chlorotricyclo[3.3.1.1 3.7]decan])-4-yl]-1-phenyl phosphate (CDP-Star chemiluminescent substrate; 200:1 dilution of a 100× stock), and ILTR (10 µM) was added to each well. Images of the plate were obtained in an IVIS 50 (FOV 10 cm; binning 8; 120 sec acquisition; filter, open, <510 nm short pass, 540AF20 nm band pass, >590 nm long pass, or >650 nm long pass in rapid secession) at 10 min, 20 min and 30 min post addition of developing solution. The images were quantified with LivingImage (Igor) software, and then analyzed with the Bioluminunmixing v.1.0 ImageJ software (Gammon, S. T., et al., Anal. Chem. 78, 1520-1527, 2006) to spectrally deconvolute (optically unmix) the HRP enzyme reaction with ILTR (>650 nm; far red) from the AP enzyme reaction with CDP-Star (<510 nm; blue-green). As shown by data presented in FIG. 16, while the open filter demonstrated uniform bioluminescence output across the plate, it was possible to resolve by spectral unmixing the HRP/ILTR enzyme gradient (right panel) from the AP/CDP-Star enzyme gradient (left panel) within the cluster of wells across the plate. Thus, our novel ILTR and other red or near-infrared isoluminol and luminol analogues will enable any peroxidase activity to be spectrally resolved from another bioluminescence or chemiluminescence enzyme activity reacting with substrates possessing spectrally resolvable emission characteristics, such as blue-green emissions, in vitro, in cellulo and in vivo.

Example 18

This example illustrates use of in vitro NIR bioluminescence to study dye and fluorophore stability under various experimental conditions.

Figure 17:
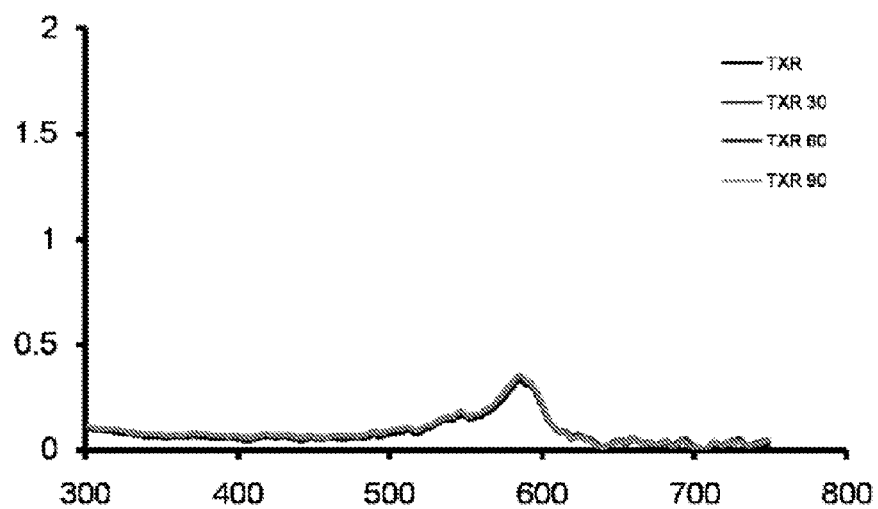
FIG. 17 illustrates absorption spectra (RLU vs nm wavelength) of Texas Red (TXR) and Infrared Dye 820 (IRD) treated with $H_2O_2$ and MPO.
Figure 18:
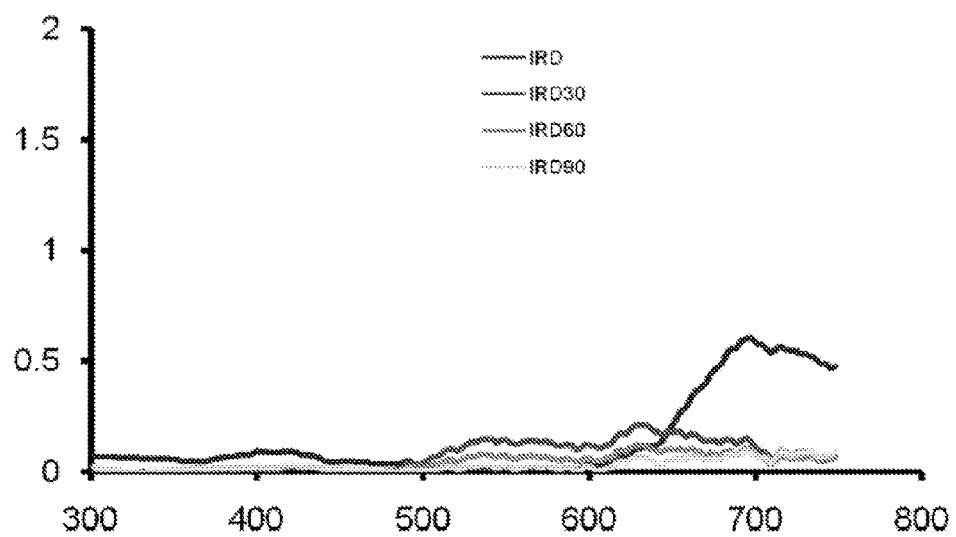
FIG. 18 illustrates time course of TXR exposure to MPO.

In these experiments, absorption spectra were collected for Texas Red (TXR) and Infrared Dye 820 (IRD) treated with $H_2O_2$ and MPO (5 mU) in Tris buffer solution for 30 min, 60 min and 90 min as indicated. The time course of TXR exposure to MPO showed the stability of the dye over time (FIG. 17, FIG. 18). In these experiments, absorption spectra were collected (RLU vs nm wavelength) of Texas Red (TXR) and Infrared Dye 820 (IRD) treated with $H_2O_2$ and MPO (5 U) in Tris buffer solution for 30 min, 60 min and 90 min as indicated. (FIG. 17). Time course of TXR exposure to MPO shows stability of the dye over time. (FIG. 18). The time course of IRD exposure to MPO shows loss of IRD molecular integrity over time. Thus, in vitro NIR bioluminescence can be used to study dye and fluorophore stability under various experimental conditions. However, the time course of IRD exposure to MPO showed the loss of IRD molecular integrity over time. Thus, in vitro NIR bioluminescence can be used in the study of dye and fluorophore stability under various experimental conditions.

Figure 19:
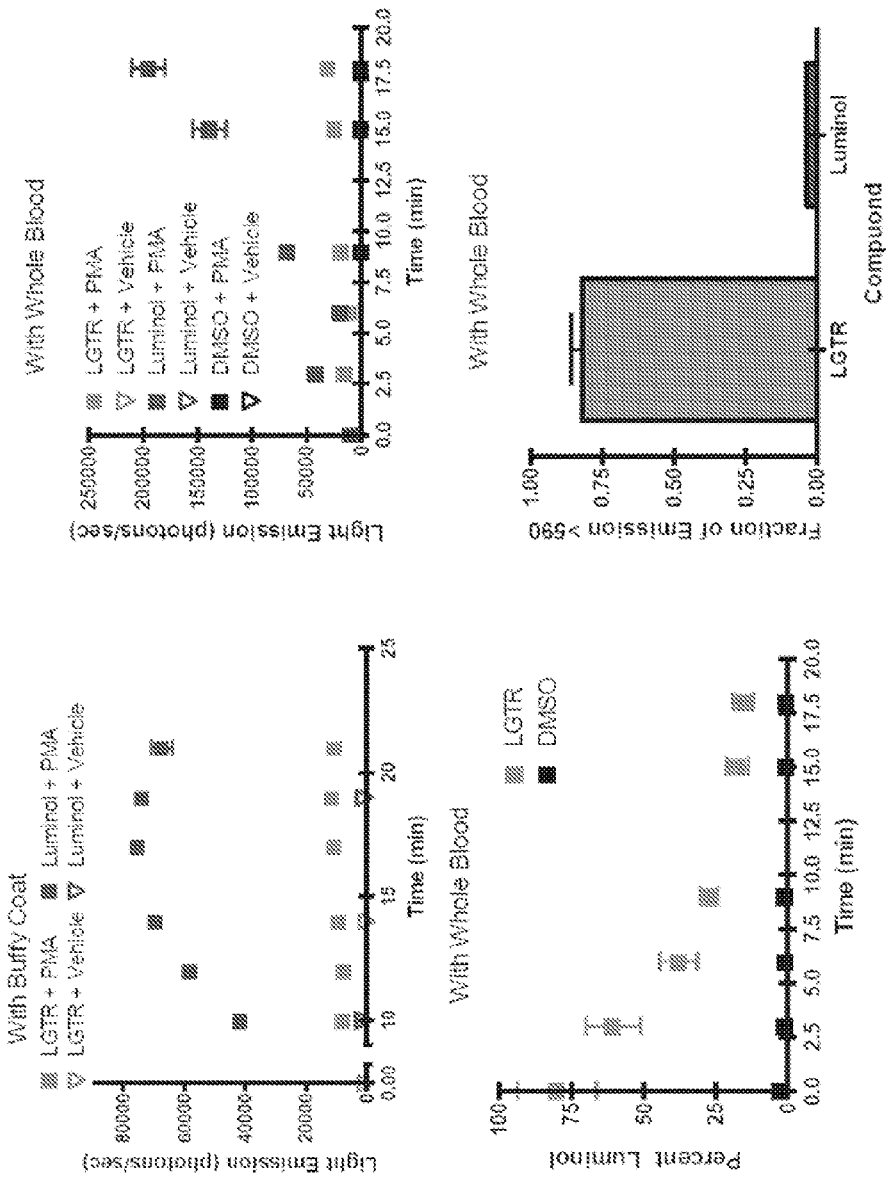
FIG. 19 illustrates ex vivo BLI experiments using whole, blood.

For analysis of LGTR in whole blood, human blood was freshly drawn from a volunteer (by venous puncture). Blood was stored for up to 6 h in heparinized tubes at room temperature. Ex vivo BLI experiments using whole blood were performed in black-coated 96-well plates. Briefly, 200 µL of blood was added to the wells. LGTR, luminol, or DMSO (10 M of each) were added to the wells. Samples were imaged (exposure time, 160 sec; binning, 8; FOV, 10 cm; open filter or >590 nm) before (t=0) and at the indicated time points after stimulation with PMA (5 µM) or vehicle (ethanol, 1 µL). Photon fluxes±s.e.m. were plotted as a function of time post PMA (min) (FIG. 19). In whole blood following PMA stimulation, the photon output of luminol exceeded LGTR; however, at 12 min post PMA stimulation, greater than 75% of the LGTR signal was red (>590 nm), far exceeding the red spectral output of luminol, and favorable for utility in vivo. Also, at early time points in whole blood, LGTR signals were greater than 75% over the luminol signals. In addition, to isolate the buffy coat (white cells), whole blood was centrifuged at 700 rpm for 8 min, and subjected to the same analysis. Similar imaging results with LGTR and luminol were observed with buffy coat as with whole blood.

Example 19

This example illustrates specific imaging of MPO activity in vivo.

Eosinophil peroxidase (EPO) is known to produce bioluminescence in vitro when luminol is utilized as a substrate (Haqqani, A., et al., Anal Biochem 273, 126-132, 1999). Therefore, to determine the contribution of EPO to the luminolBLI signal in vivo, we characterized a model of allergic contact hypersensitivity. A contact hypersensitivity model of allergic dermatitis manifested by erythema, edema and extensive infiltration of eosinophils and neutrophils was induced by passive immunization with antidinitrophenol (DNP) IgE and topical challenge with dinitrofluorobenzene (DNFB). Briefly, murine anti-DNP IgE (20 µg in 100 Sigma-Aldrich) was injected intravenously into 13 $MPO^{+/-}$ and 9 $MPO^{-/-}$ mice. One control mouse of each genetic MPO background was injected with vehicle (saline) only. Twenty-four hours later, all left ears were painted with DNFB (0.2% in acetone: olive oil, 1:3) and all right ears were painted with vehicle (acetone:olive oil, 1:3). On the next day, all mice were imaged following luminol administration (200 mg/kg BW, i.p.). Mice were euthanized immediately after imaging and histological specimens were prepared from both left and right ears by fixation with paraformaldehyde (4%), de-calcification (24 h in 14% EDTA), paraffin-embedding, sectioning (5 m) and staining with H&E. For each condition, eosinophils were counted in 5 HPF (magnification ×400).

Thus, eosinophil-dominant recruitment and activation was induced by passive immunization against DNP followed by topical challenge with DNFB (Ray, M., et al., J Immunol 131, 1096-1102, 1983) in both $MPO^{+/+}$ control as well as $MPO^{-/-}$ mice. Because the only peroxidase present at the site of allergic inflammation in $MPO^{-/-}$ mice would be EPO, comparing the two MPO genetic backgrounds should reveal the fraction of the BL signal originating from EPO in vivo. Importantly, induction of acute contact hypersensitivity in $MPO^{-/-}$ mice resulted in no significant luminol-BL signal from the inflamed ears, while in $MPO^{+/+}$ mice, substantial luminol-BL was observed (FIG. 21a,b). In control mice that were not immunized with anti-DNP IgE, and in vehicle-treated ears of both MPO genetic backgrounds, no significant luminol-BLI signal was observed (FIG. 21a,b). To confirm that indeed eosinophils had infiltrated the inflamed ears, histological analysis of tissue specimens was undertaken 24 h post DNFB treatment (FIG. 21c). A prominent eosinophilia within a mixed cell infiltrate was observed. Similar numbers of eosinophils were recruited to the inflamed ears of both $MPO^{+/+}$ and $MPO^{-/-}$ mice, while in both genotypes, vehicle treatment failed to induce eosinophilic infiltration (FIG. 21c, d). Furthermore, immunohistochemical analysis with an anti-dibromotyrosine mAb directly identified the presence of bromotyrosine adducts in the inflamed ears of both $MPO^{+/+}$ and $MPO^{-/-}$ mice, but not vehicle-treated ears (FIG. 21c, insets). These data directly confirmed the presence of active EPO in $MPO^{-/-}$ mice, despite the absence of luminol-BLI signals. Thus, we conclude that the contribution of EPO to luminol-BLI in vivo is negligible (also see FIG. 4).

Figure 22:
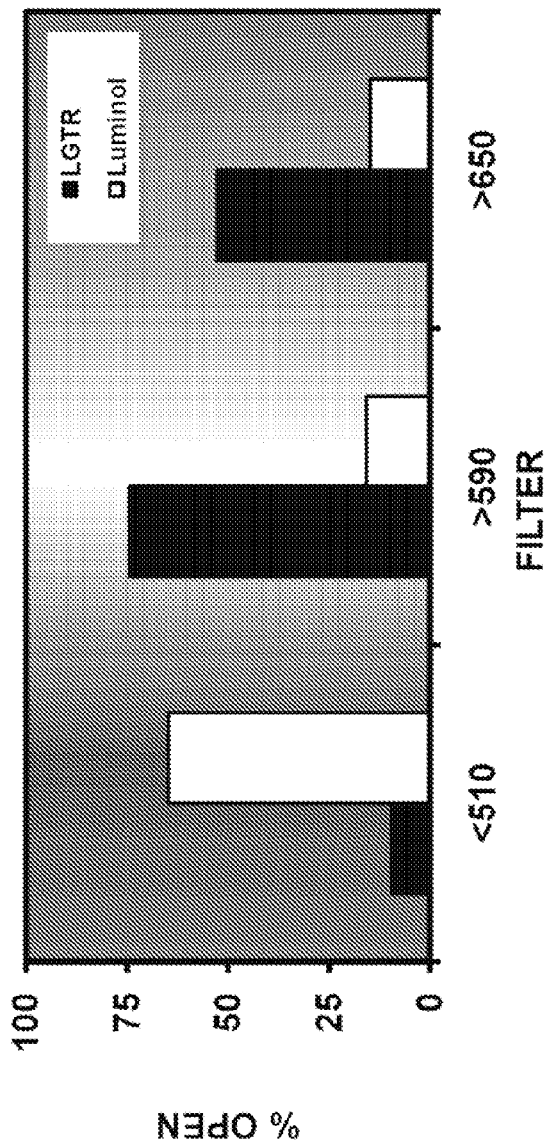
FIG. 22 illustrates monitoring of MPO activity in vivo with luminol- and LGTR-bioluminescence imaging.
Figure 23:
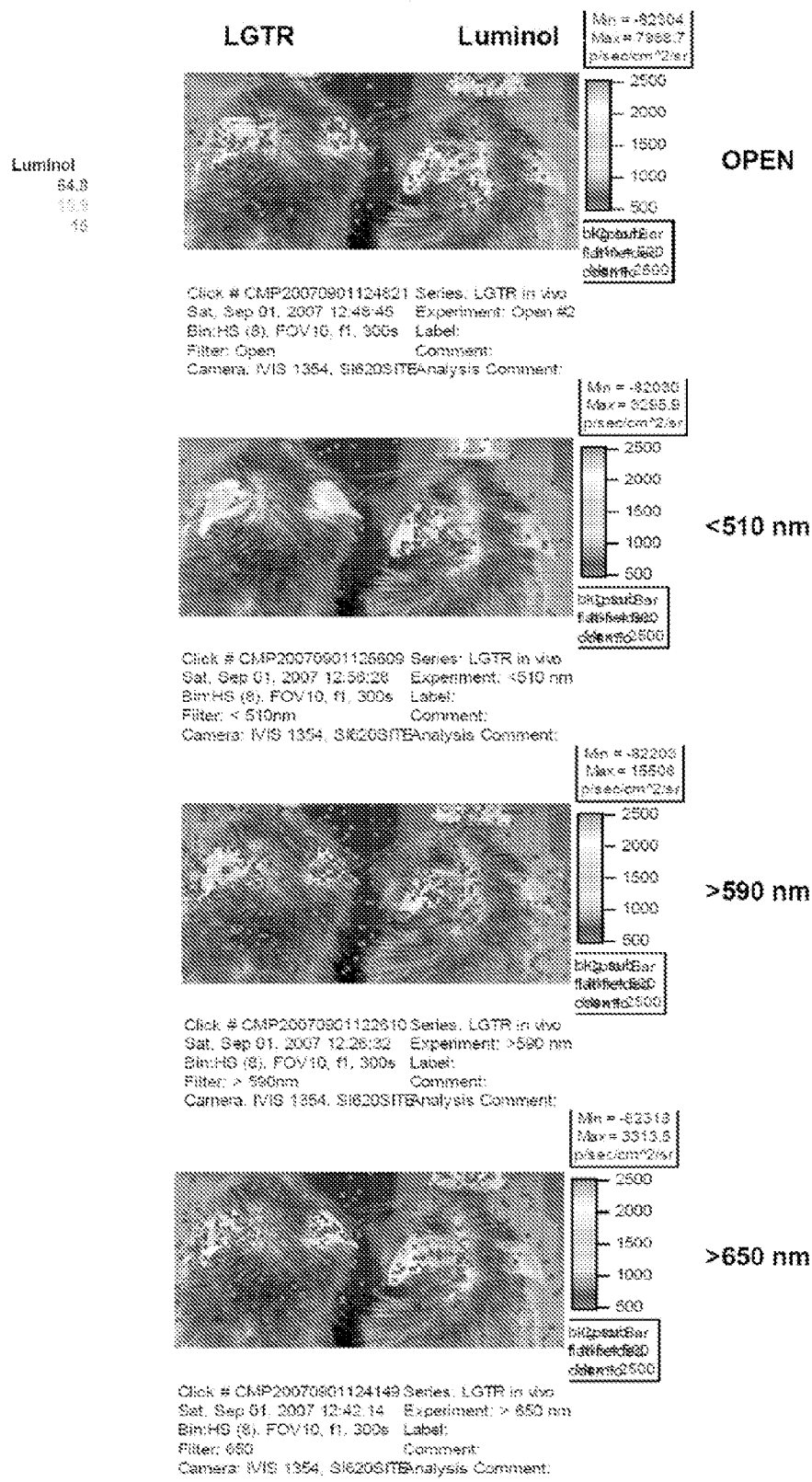
FIG. 23 illustrates monitoring of MPO activity in vivo with luminol- and LGTR-bioluminescence imaging.

In another experiment characterizing the properties of a NIR luminol derivative, forty-eight hrs post passive immunization with anti-dinitrophenol (DNP) IgE and topical challenge with DNFB as above, luminol-glycine-Texas Red (LGTR; 1 mM in DMSO, left mouse) or luminol (1 mM in DMSO, right mouse) were applied topically (45 µl per ear) on both the left and right ears. Thirty min later, mice were simultaneously imaged in the IVIS 100 imaging system (FOV, 10 cm; binning, 8; acquisition time, 300 sec; f/stop, 1) using four different optical filter sets in rapid sequence: 1) no filter, 2) <510 nm filter, 3) >590 nm filter, and 4) >650 nm filter (FIG. 22, FIG. 23). The photon flux as a percentage of an open filter was compared for both compounds (FIG. 23). Importantly, following induction of acute contact hypersensitivity in MPO+/+ mice, substantial LGTR-BL was observed. These studies demonstrate that MPO activity can be directly monitored in vivo with luminol- and LGTR-bioluminescence imaging.

Contact hypersensitivity model: We induced allergic dermatitis, manifested by erythema, edema and extensive infiltration of neutrophils and eosinophils by passive immunization. Briefly, murine anti-DNP IgE (20 µg, 100 µl) was intravenously injected to two C57/B mice. Twenty-four hours later, their left ears were painted with dinitrofluorobenzene (DNFB, 0.2% in acetone: olive oil 1:3) and their right ears were painted with vehicle (acetone: olive oil 1:3).

Administration of luminol derivatives and imaging: Forty-eight hours post DNFB treatment, luminol-glycine Texas Red (LGTR, 1 mM in DMSO, left mouse) or luminol (1 mM In DMSO, right mouse) were applied topically (45 µl per ear) on both left and right ears. Thirty minutes later, mice were simultaneously imaged using the IVIS 100 imaging system (FOV 10 cm; binning, 8; acquisition time. 300 sec; f/stop, 1) using four different optical filler sets: (1) no filter, (2)<510 nm filler, (3)>590 nm filter and (4)>650 nm filter.

LGTR demonstrates a 3-4 fold higher photon flux using filters>590 and 650 nm compared with luminal, indicating its ability to serve as an in vivo NIR probe for bioluminescence imaging of allergic dermatitis.

Figure 24:
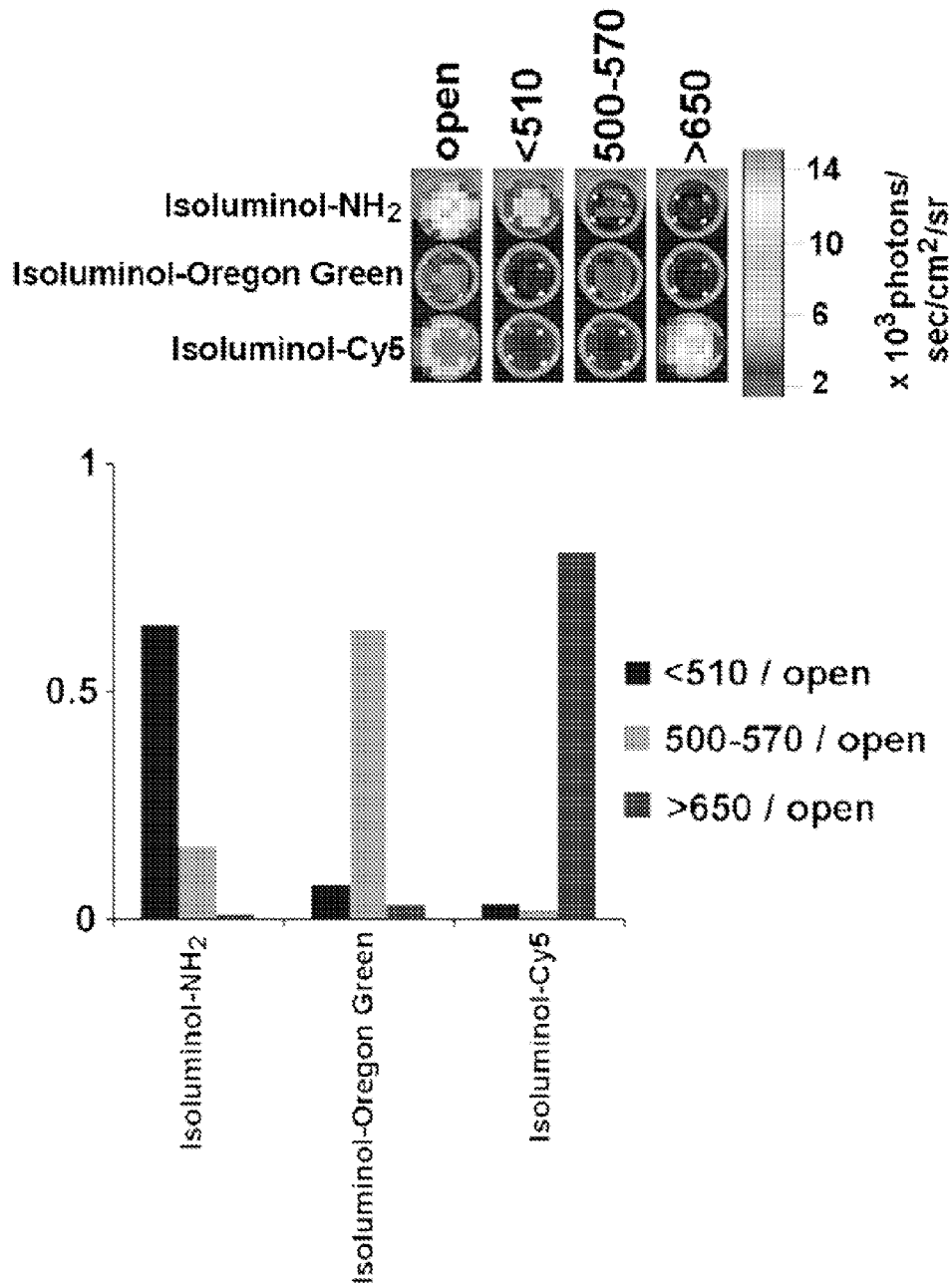
FIG. 24 illustrates bioluminescence of Isoluminol-NH2, Isoluminol-Oregon Green, and Isoluminol-Cy5 as observed under different light filter conditions.

Bioluminescence was measured for Isoluminol-NH$_2$, Isoluminol-Oregon Green, and Isoluminol-Cy5 under different light filter conditions, i.e., <510 nm/open; 500-570 nm/open; >650 nm/open (FIG. 24).

All publications, patents, patent application publications cited herein are incorporated by reference, each in its entirety.

What is claimed is:

1. A compound or salt thereof of structure

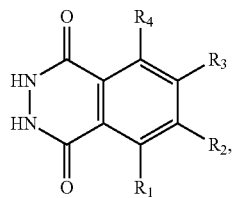

wherein $R_2$ and $R_3$ are each selected from the group consisting of H, $C_1$-$C_{20}$ alkyl, $C_1$-$C_{20}$ alkenyl, $C_1$-$C_{20}$ alkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, a nitro, a nitrite, a sulfate, a sulfide, a sulfonamide, a phosphate, a borate, and a halogen; at least one of $R_1$ or $R_4$ is

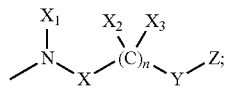

wherein $X_1$ is selected from the group consisting of H, $C_1$-$C_{20}$ alkyl, $C_1$-$C_{20}$ alkenyl, $C_1$-$C_{20}$ alkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, a nitro, a nitrile, a sulfate, a sulfide, a sulfonamide, a phosphate, a borate, and a halogen; X is selected from the group consisting of a $C_1$-$C_{20}$ alkyl, $C_1$-$C_{20}$ heteroalkyl $C_1$-$C_{20}$ alkenyl, $C_1$-$C_{20}$ heteroalkenyl, $C_1$-$C_{20}$ alkynyl, $C_1$-$C_{20}$ heteroalkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, and a sulfonamide; Y is selected from the group consisting of an amide, a sulfonamide, an acetyl, a ketone, an ester, and an ether; n is an integer from 0 to 20; $X_2$ and $X_3$ are each selected from the group consisting of H, $C_1$-$C_{20}$ alkyl, $C_1$-$C_{20}$ alkenyl, $C_1$-$C_{20}$ alkynyl, $C_1$-$C_{20}$ aryl, $C_1$-$C_{20}$ heteroaryl, $C_1$-$C_{20}$ carboxyl, $C_1$-$C_{20}$ carbonyl, an ester, an ether, an amine, an amide, a nitro, a nitrile, a sulfate, a sulfide, a sulfonamide, a phosphate, a borate and a halogen; and wherein Z is a light emitting moiety.

2. A compound or salt thereof in accordance with claim 1, wherein an $X_2$ and an $X_3$ together comprise an aliphatic or aromatic cyclic moiety.

3. A compound or salt thereof in accordance with claim 1, wherein $R_2$ and $R_3$ together comprise an aliphatic or aromatic cyclic moiety.

4. A compound or salt thereof in accordance with claim 1, wherein Z is a fluorescent moiety selected from the group consisting of a fluorescein, a squaraine, a rotaxane, a rhodamine, a Texas Red, an Oregon Green, a Cascade Yellow, a Lucifer Yellow, an AlexaFluor, a CY5, a CY3, and a quantum dot.

5. A compound or salt thereof in accordance with claim 1, having the following formula:

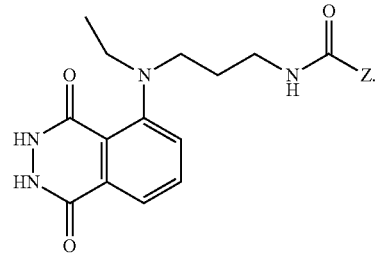

6. A compound or salt thereof of structure

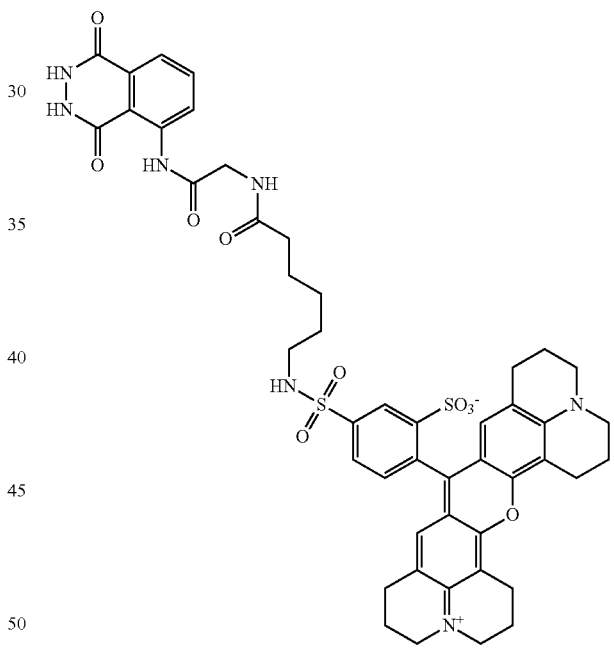

(Lumino)-Glycine-Texas Red).

* * * * *